(12) United States Patent
Simpson et al.

(10) Patent No.: US 9,131,885 B2
(45) Date of Patent: Sep. 15, 2015

(54) ANALYTE SENSORS AND METHODS OF MANUFACTURING SAME

(75) Inventors: Peter C. Simpson, Encinitas, CA (US); Robert Boock, Carlsbad, CA (US); Paul V. Neale, San Diego, CA (US); Sebastian Bohm, Carlsbad, CA (US); Matthew Wightlin, San Diego, CA (US); Jack Pryor, San Diego, CA (US); Jason Mitchell, San Diego, CA (US); Jeff Jackson, Poway, CA (US); Kaushik Patel, Poway, CA (US); Antonio C. Llevares, Chula Vista, CA (US)

(73) Assignee: DexCom, Inc., San Diego, CA (US)

( * ) Notice: Subject to any disclaimer, the term of this patent is extended or adjusted under 35 U.S.C. 154(b) by 1384 days.

(21) Appl. No.: 12/829,318

(22) Filed: Jul. 1, 2010

(65) Prior Publication Data
US 2011/0028816 A1   Feb. 3, 2011

Related U.S. Application Data

(60) Provisional application No. 61/222,716, filed on Jul. 2, 2009, provisional application No. 61/222,815, filed on Jul. 2, 2009, provisional application No. 61/222,751, filed on Jul. 2, 2009.

(51) Int. Cl.
*A61B 5/05* (2006.01)
*A61B 5/1473* (2006.01)
(Continued)

(52) U.S. Cl.
CPC .............. *A61B 5/1473* (2013.01); *A61B 5/1451* (2013.01); *A61B 5/14517* (2013.01);
(Continued)

(58) Field of Classification Search
CPC ............. A61B 5/1486; A61B 5/14865; A61B 5/1473; A61B 5/14532; A61B 5/1451; A61B 5/14517; G01N 27/327; G01N 27/3271; B05C 3/10

USPC .................. 600/345–361, 365, 316, 309; 427/2.1–2.13; 156/345.15, 345.2; 118/400–429, 56
See application file for complete search history.

(56) References Cited

U.S. PATENT DOCUMENTS

| | | |
|---|---|---|
| 3,957,613 A | 5/1976 | Macur |
| 4,442,841 A | 4/1984 | Uehara et al. |

(Continued)

FOREIGN PATENT DOCUMENTS

| | | |
|---|---|---|
| EP | 0 098 592 | 1/1984 |
| EP | 0 127 958 | 12/1984 |

(Continued)

OTHER PUBLICATIONS

Technical Bulletin, Fort Wayne Metals, 2007. Retrieved from the internet <http://web.archive.org/web/20070719033448/http://www.fwmetals.com/resources_pdf/FWW%20Technical%20Binder.pdf>.*

(Continued)

*Primary Examiner* — Patricia Mallari
*Assistant Examiner* — Eric Messersmith
(74) *Attorney, Agent, or Firm* — Knobbe Martens Olson & Bear LLP

(57) ABSTRACT

Analyte sensors and methods of manufacturing same are provided, including analyte sensors comprising multi-axis flexibility. For example, a multi-electrode sensor system 800 comprising two working electrodes and at least one reference/counter electrode is provided. The sensor system 800 comprises first and second elongated bodies E1, E2, each formed of a conductive core or of a core with a conductive layer deposited thereon, insulating layer 810 that separates the conductive layer 820 from the elongated body, a membrane layer deposited on top of the elongated bodies E1, E2, and working electrodes 802', 802" formed by removing portions of the conductive layer 820 and the insulating layer 810, thereby exposing electroactive surface of the elongated bodies E1, E2.

24 Claims, 23 Drawing Sheets

(51) Int. Cl.
  *A61B 5/145* (2006.01)
  *A61B 5/1486* (2006.01)
  *B05C 3/10* (2006.01)

(52) U.S. Cl.
  CPC ......... *A61B5/14532* (2013.01); *A61B 5/14865* (2013.01); *B05C 3/10* (2013.01); *A61B 2560/0223* (2013.01); *A61B 2562/0209* (2013.01); *A61B 2562/043* (2013.01); *A61B 2562/125* (2013.01)

(56) References Cited

U.S. PATENT DOCUMENTS

| | | |
|---|---|---|
| 4,534,355 A | 8/1985 | Potter |
| 4,614,514 A | 9/1986 | Carr et al. |
| 4,671,288 A | 6/1987 | Gough |
| 4,672,970 A | 6/1987 | Uchida et al. |
| 4,680,268 A | 7/1987 | Clark, Jr. |
| 4,685,463 A | 8/1987 | Williams |
| 4,721,677 A | 1/1988 | Clark, Jr. |
| 4,736,748 A | 4/1988 | Nakamura et al. |
| 4,759,828 A | 7/1988 | Young et al. |
| 4,908,115 A | 3/1990 | Morita et al. |
| 4,935,345 A | 6/1990 | Guilbeau et al. |
| 4,974,592 A | 12/1990 | Branco |
| 5,063,081 A | 11/1991 | Cozzette et al. |
| 5,067,491 A | 11/1991 | Taylor, II et al. |
| 5,101,814 A | 4/1992 | Palti |
| 5,130,009 A | 7/1992 | Marsoner et al. |
| 5,165,407 A | 11/1992 | Wilson et al. |
| 5,190,040 A | 3/1993 | Aoyagi |
| 5,200,051 A | 4/1993 | Cozzette et al. |
| 5,212,050 A | 5/1993 | Mier et al. |
| 5,286,364 A | 2/1994 | Yacynych et al. |
| 5,310,469 A | 5/1994 | Cunningham |
| 5,368,028 A | 11/1994 | Palti |
| 5,380,422 A | 1/1995 | Negishi et al. |
| 5,431,160 A | 7/1995 | Wilkins |
| 5,466,575 A | 11/1995 | Cozzette et al. |
| 5,476,776 A | 12/1995 | Wilkins |
| 5,494,562 A | 2/1996 | Maley et al. |
| 5,509,888 A | 4/1996 | Miller |
| 5,554,339 A | 9/1996 | Cozzette |
| 5,593,852 A | 1/1997 | Heller et al. |
| 5,611,900 A | 3/1997 | Worden |
| 5,624,537 A | 4/1997 | Turner et al. |
| 5,676,651 A | 10/1997 | Larson et al. |
| 5,676,820 A | 10/1997 | Wang et al. |
| 5,682,884 A | 11/1997 | Hill et al. |
| 5,707,502 A | 1/1998 | McCaffrey et al. |
| 5,711,861 A | 1/1998 | Ward et al. |
| 5,773,270 A | 6/1998 | D'Orazio et al. |
| 5,837,454 A | 11/1998 | Cozzette et al. |
| 5,863,460 A | 1/1999 | Slovacek et al. |
| 5,964,993 A | 10/1999 | Blubaugh et al. |
| 5,965,380 A | 10/1999 | Heller et al. |
| 5,972,199 A | 10/1999 | Heller et al. |
| 5,985,129 A | 11/1999 | Gough et al. |
| 6,032,059 A | 2/2000 | Henning et al. |
| 6,081,736 A | 6/2000 | Colvin et al. |
| 6,083,710 A | 7/2000 | Heller et al. |
| 6,121,009 A | 9/2000 | Heller et al. |
| 6,162,611 A | 12/2000 | Heller et al. |
| 6,175,752 B1 | 1/2001 | Say et al. |
| 6,201,980 B1 | 3/2001 | Darrow et al. |
| 6,212,416 B1 | 4/2001 | Ward et al. |
| 6,254,586 B1 | 7/2001 | Mann et al. |
| 6,280,408 B1 | 8/2001 | Sipin |
| 6,284,478 B1 | 9/2001 | Heller et al. |
| 6,306,594 B1 | 10/2001 | Cozzette |
| 6,329,161 B1 | 12/2001 | Heller et al. |
| 6,360,888 B1 | 3/2002 | McIvor et al. |
| 6,407,195 B2 | 6/2002 | Sherman et al. |
| 6,413,393 B1 | 7/2002 | Van Antwerp et al. |
| 6,461,496 B1 | 10/2002 | Feldman et al. |
| 6,466,810 B1 | 10/2002 | Ward et al. |
| 6,501,976 B1 | 12/2002 | Sohrab |
| 6,512,939 B1 | 1/2003 | Colvin, Jr. et al. |
| 6,514,718 B2 | 2/2003 | Heller et al. |
| 6,520,326 B2 | 2/2003 | McIvor et al. |
| 6,542,765 B1 | 4/2003 | Guy et al. |
| 6,558,321 B1 | 5/2003 | Burd et al. |
| 6,560,471 B1 | 5/2003 | Heller et al. |
| 6,561,978 B1 | 5/2003 | Conn et al. |
| 6,565,509 B1 | 5/2003 | Plante et al. |
| 6,579,690 B1 | 6/2003 | Bonnecaze et al. |
| 6,592,745 B1 | 7/2003 | Feldman et al. |
| 6,618,934 B1 | 9/2003 | Feldman et al. |
| 6,648,821 B2 | 11/2003 | Lebel et al. |
| 6,654,625 B1 | 11/2003 | Say et al. |
| 6,689,265 B2 | 2/2004 | Heller et al. |
| 6,740,075 B2 | 5/2004 | Lebel et al. |
| 6,809,653 B1 | 10/2004 | Mann et al. |
| 6,810,290 B2 | 10/2004 | Lebel et al. |
| 6,814,845 B2 | 11/2004 | Wilson et al. |
| 6,881,551 B2 | 4/2005 | Heller et al. |
| 6,892,085 B2 | 5/2005 | McIvor et al. |
| 6,965,791 B1 | 11/2005 | Hitchcock et al. |
| 6,975,893 B2 | 12/2005 | Say et al. |
| 6,989,891 B2 | 1/2006 | Braig et al. |
| 6,990,366 B2 | 1/2006 | Say et al. |
| 7,003,341 B2 | 2/2006 | Say et al. |
| 7,006,871 B1 | 2/2006 | Darvish et al. |
| 7,061,593 B2 | 6/2006 | Braig et al. |
| 7,098,803 B2 | 8/2006 | Mann et al. |
| 7,163,511 B2 | 1/2007 | Conn et al. |
| 7,190,988 B2 | 3/2007 | Say et al. |
| 7,310,544 B2 | 12/2007 | Brister et al. |
| 7,364,592 B2 | 4/2008 | Carr-Brendel et al. |
| 7,399,277 B2 | 7/2008 | Saidara et al. |
| 7,422,585 B1 | 9/2008 | Eggers et al. |
| 7,424,318 B2 | 9/2008 | Brister et al. |
| 7,460,898 B2 | 12/2008 | Brister et al. |
| 7,467,003 B2 | 12/2008 | Brister et al. |
| 7,494,465 B2 | 2/2009 | Brister et al. |
| 7,497,827 B2 | 3/2009 | Brister et al. |
| 7,519,408 B2 | 4/2009 | Rasdal et al. |
| 7,519,433 B2 | 4/2009 | Foley |
| 8,244,371 B2 | 8/2012 | Spehr et al. |
| 2002/0023852 A1 | 2/2002 | McIvor et al. |
| 2002/0042090 A1 | 4/2002 | Heller et al. |
| 2002/0084196 A1 | 7/2002 | Liamos et al. |
| 2002/0151816 A1 | 10/2002 | Rich et al. |
| 2002/0169369 A1* | 11/2002 | Ward et al. .................. 600/347 |
| 2003/0050546 A1 | 3/2003 | Desai et al. |
| 2003/0078481 A1 | 4/2003 | McIvor et al. |
| 2003/0100040 A1 | 5/2003 | Bonnecaze et al. |
| 2003/0100821 A1 | 5/2003 | Heller et al. |
| 2003/0104119 A1 | 6/2003 | Wilson et al. |
| 2003/0125612 A1 | 7/2003 | Fox et al. |
| 2003/0134347 A1 | 7/2003 | Heller et al. |
| 2003/0187338 A1 | 10/2003 | Say et al. |
| 2003/0199744 A1 | 10/2003 | Buse et al. |
| 2003/0235817 A1 | 12/2003 | Bartkowiak et al. |
| 2004/0039298 A1 | 2/2004 | Abreu |
| 2004/0074785 A1 | 4/2004 | Holker |
| 2004/0078219 A1 | 4/2004 | Kaylor |
| 2004/0106859 A1 | 6/2004 | Say et al. |
| 2004/0111017 A1 | 6/2004 | Say et al. |
| 2004/0138543 A1* | 7/2004 | Russell et al. ............... 600/345 |
| 2004/0167801 A1 | 8/2004 | Say et al. |
| 2004/0180391 A1 | 9/2004 | Gratzl et al. |
| 2004/0236200 A1 | 11/2004 | Say et al. |
| 2004/0253365 A1 | 12/2004 | Warren et al. |
| 2005/0016325 A1 | 1/2005 | Enokido |
| 2005/0027182 A1 | 2/2005 | Siddiqui et al. |
| 2005/0038330 A1* | 2/2005 | Jansen et al. ............... 600/345 |
| 2005/0038332 A1 | 2/2005 | Saidara et al. |
| 2005/0051427 A1 | 3/2005 | Brauker et al. |
| 2005/0113653 A1 | 5/2005 | Fox et al. |
| 2005/0121322 A1 | 6/2005 | Say et al. |
| 2005/0143635 A1 | 6/2005 | Kamath et al. |
| 2005/0154271 A1 | 7/2005 | Rasdal et al. |
| 2005/0176136 A1 | 8/2005 | Burd et al. |

(56) References Cited

U.S. PATENT DOCUMENTS

| | | |
|---|---|---|
| 2005/0181012 A1 | 8/2005 | Saint et al. |
| 2005/0182451 A1 | 8/2005 | Griffin et al. |
| 2005/0183954 A1 | 8/2005 | Hitchcock et al. |
| 2005/0209665 A1 | 9/2005 | Hunter et al. |
| 2005/0233407 A1 | 10/2005 | Pamidi et al. |
| 2005/0251083 A1 | 11/2005 | Carr-Brendel et al. |
| 2005/0272989 A1 | 12/2005 | Shah et al. |
| 2005/0288596 A1 | 12/2005 | Eigler et al. |
| 2006/0001550 A1 | 1/2006 | Mann et al. |
| 2006/0003398 A1 | 1/2006 | Heller et al. |
| 2006/0015024 A1 | 1/2006 | Brister et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0052745 A1 | 3/2006 | Van Antwerp et al. |
| 2006/0142651 A1 | 6/2006 | Brister et al. |
| 2006/0155180 A1 | 7/2006 | Brister et al. |
| 2006/0173444 A1 | 8/2006 | Choy et al. |
| 2006/0183984 A1 | 8/2006 | Dobbles et al. |
| 2006/0183985 A1 | 8/2006 | Brister et al. |
| 2006/0189863 A1 | 8/2006 | Peyser et al. |
| 2006/0195029 A1 | 8/2006 | Shults et al. |
| 2006/0200020 A1 | 9/2006 | Brister et al. |
| 2006/0200970 A1 | 9/2006 | Brister et al. |
| 2006/0222566 A1 | 10/2006 | Brauker et al. |
| 2006/0229512 A1 | 10/2006 | Petisce et al. |
| 2006/0235285 A1 | 10/2006 | Brister et al. |
| 2006/0249381 A1 | 11/2006 | Petisce et al. |
| 2006/0253012 A1 | 11/2006 | Petisce et al. |
| 2006/0257995 A1 | 11/2006 | Simpson et al. |
| 2006/0257996 A1 | 11/2006 | Simpson et al. |
| 2006/0258761 A1 | 11/2006 | Boock et al. |
| 2006/0258929 A1 | 11/2006 | Goode et al. |
| 2006/0263763 A1 | 11/2006 | Simpson et al. |
| 2006/0263839 A1 | 11/2006 | Ward et al. |
| 2006/0270922 A1 | 11/2006 | Brauker et al. |
| 2006/0270923 A1 | 11/2006 | Brauker et al. |
| 2006/0289307 A1 | 12/2006 | Yu et al. |
| 2006/0293576 A1 | 12/2006 | Van Antwerp et al. |
| 2007/0016381 A1 | 1/2007 | Kamath et al. |
| 2007/0027370 A1 | 2/2007 | Brauker et al. |
| 2007/0027385 A1 | 2/2007 | Brister et al. |
| 2007/0032706 A1 | 2/2007 | Kamath et al. |
| 2007/0032717 A1 | 2/2007 | Brister et al. |
| 2007/0038044 A1 | 2/2007 | Dobbles et al. |
| 2007/0045902 A1 | 3/2007 | Brauker et al. |
| 2007/0059196 A1 | 3/2007 | Brister et al. |
| 2007/0066873 A1 | 3/2007 | Kamath et al. |
| 2007/0093704 A1 | 4/2007 | Brister et al. |
| 2007/0129619 A1 | 6/2007 | Ward et al. |
| 2007/0135698 A1 | 6/2007 | Shah et al. |
| 2007/0135699 A1 | 6/2007 | Ward et al. |
| 2007/0151869 A1 | 7/2007 | Heller et al. |
| 2007/0163880 A1 | 7/2007 | Woo et al. |
| 2007/0173709 A1 | 7/2007 | Petisce et al. |
| 2007/0173710 A1 | 7/2007 | Petisce et al. |
| 2007/0197889 A1 | 8/2007 | Brister et al. |
| 2007/0197890 A1 | 8/2007 | Boock et al. |
| 2007/0202562 A1 | 8/2007 | Curry |
| 2007/0203966 A1 | 8/2007 | Brauker et al. |
| 2007/0208244 A1 | 9/2007 | Brauker et al. |
| 2007/0208245 A1 | 9/2007 | Brauker et al. |
| 2007/0208246 A1 | 9/2007 | Brauker et al. |
| 2007/0213610 A1 | 9/2007 | Say et al. |
| 2007/0213611 A1 | 9/2007 | Simpson et al. |
| 2007/0215491 A1 | 9/2007 | Heller et al. |
| 2007/0218097 A1 | 9/2007 | Heller et al. |
| 2007/0227907 A1 | 10/2007 | Shah et al. |
| 2007/0232879 A1 | 10/2007 | Brister et al. |
| 2007/0235331 A1 | 10/2007 | Simpson et al. |
| 2007/0244379 A1 | 10/2007 | Boock et al. |
| 2008/0033269 A1 | 2/2008 | Zhang |
| 2008/0086040 A1 | 4/2008 | Heller et al. |
| 2008/0086041 A1 | 4/2008 | Heller et al. |
| 2008/0086042 A1 | 4/2008 | Brister et al. |
| 2008/0086043 A1 | 4/2008 | Heller et al. |
| 2008/0086044 A1 | 4/2008 | Brister et al. |
| 2008/0086273 A1 | 4/2008 | Shults et al. |
| 2008/0091094 A1 | 4/2008 | Heller et al. |
| 2008/0091095 A1 | 4/2008 | Heller et al. |
| 2008/0108942 A1 | 5/2008 | Brister et al. |
| 2008/0119703 A1 | 5/2008 | Brister et al. |
| 2008/0119704 A1 | 5/2008 | Brister et al. |
| 2008/0119706 A1 | 5/2008 | Brister et al. |
| 2008/0188731 A1 | 8/2008 | Brister et al. |
| 2008/0194935 A1 | 8/2008 | Brister et al. |
| 2008/0194938 A1 | 8/2008 | Brister et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0208025 A1 | 8/2008 | Shults et al. |
| 2008/0214915 A1 | 9/2008 | Brister et al. |
| 2008/0214918 A1 | 9/2008 | Brister et al. |
| 2008/0242961 A1 | 10/2008 | Brister et al. |
| 2008/0275313 A1 | 11/2008 | Brister et al. |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0296155 A1 | 12/2008 | Shults et al. |
| 2008/0313896 A1 | 12/2008 | Shah et al. |
| 2009/0018424 A1 | 1/2009 | Kamath et al. |
| 2009/0036763 A1 | 2/2009 | Brauker et al. |
| 2009/0076356 A1 | 3/2009 | Simpson |
| 2009/0076360 A1 | 3/2009 | Brister et al. |
| 2009/0076361 A1 | 3/2009 | Kamath et al. |
| 2009/0099436 A1 | 4/2009 | Brister et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0156924 A1 | 6/2009 | Shariati et al. |
| 2011/0027127 A1 | 2/2011 | Simpson et al. |
| 2011/0028815 A1 | 2/2011 | Simpson et al. |

FOREIGN PATENT DOCUMENTS

| | | |
|---|---|---|
| EP | 0 286 118 A2 | 10/1988 |
| EP | 0 320 109 | 6/1989 |
| EP | 0 351 892 | 1/1990 |
| EP | 0 390 390 | 10/1990 |
| EP | 0 535 898 | 4/1993 |
| EP | 0 351 891 B1 | 9/1993 |
| EP | 0 561 966 B1 | 10/1994 |
| EP | 1 413 245 A2 | 4/2004 |
| WO | WO 89/05977 | 6/1989 |
| WO | WO 90/05910 | 5/1990 |
| WO | WO 90/13021 | 11/1990 |
| WO | WO 91/09302 | 6/1991 |
| WO | WO 92/10584 | 6/1992 |
| WO | WO 94/24262 | 10/1994 |
| WO | WO 95/11454 | 4/1995 |
| WO | WO 96/06947 | 3/1996 |
| WO | WO 98/30891 | 7/1998 |
| WO | WO 99/56613 | 4/1999 |

(56) References Cited

FOREIGN PATENT DOCUMENTS

| | | |
|---|---|---|
| WO | WO 00/13003 | 3/2000 |
| WO | WO 00/19887 | 4/2000 |
| WO | WO 00/20626 | 4/2000 |
| WO | WO 00/49940 | 8/2000 |
| WO | WO 00/78992 | 12/2000 |
| WO | WO 01/33216 | 5/2001 |
| WO | WO 01/54753 | 8/2001 |
| WO | WO 01/58348 A2 | 8/2001 |
| WO | WO 01/88524 A1 | 11/2001 |
| WO | WO 01/88534 | 11/2001 |
| WO | WO 02/058537 | 8/2002 |
| WO | WO 02/095355 | 11/2002 |
| WO | WO 02/097414 | 12/2002 |
| WO | WO 03/008014 | 1/2003 |
| WO | WO 03/022128 | 3/2003 |
| WO | WO 03/057027 | 7/2003 |
| WO | WO 03/076937 | 9/2003 |
| WO | WO 03/088832 | 10/2003 |
| WO | WO 03/106966 | 12/2003 |
| WO | WO 2004/036183 | 4/2004 |
| WO | WO 2005/020797 | 3/2005 |
| WO | WO 2005/026689 | 3/2005 |
| WO | WO 2005/026690 | 3/2005 |
| WO | WO 2005/048834 | 6/2005 |
| WO | WO 2005/057168 | 6/2005 |
| WO | WO 2005/065538 | 7/2005 |
| WO | WO 2005/121355 | 12/2005 |
| WO | WO 2005/121785 | 12/2005 |
| WO | WO 2006/017358 | 2/2006 |
| WO | WO 2006/018425 | 2/2006 |
| WO | WO 2006/029293 | 3/2006 |
| WO | WO 2006/076412 | 7/2006 |
| WO | WO 2006/124759 | 11/2006 |
| WO | WO 2007/011587 | 1/2007 |
| WO | WO 2007/053832 | 5/2007 |
| WO | WO 2007/070486 | 6/2007 |
| WO | WO 2007/079015 | 7/2007 |
| WO | WO 2007/079025 | 7/2007 |
| WO | WO 2007/081811 | 7/2007 |
| WO | WO 2007/097754 | 8/2007 |
| WO | WO 2007/114943 | 10/2007 |
| WO | WO 2008/013849 | 1/2008 |

OTHER PUBLICATIONS

Poncin and Proft, "Stent Tubing: Understanding the Desired Attributes," presented at Materials and Processes for Medical Devices Conference (Anaheim, CA), ASM International, Sep. 8-10 2003.*

Lewandowski et al. "Tension and fatigue behavior of 316LVM 1×7 multi-strand cables used as implantable electrodes," Mater Sci Eng A Struct Mater. Jul. 15, 2008;486(1-2):447-454.*

Lewandwoski et al., "Tension and fatigue behavior of silver-cored composite multi-strand cables used as implantable cables and electrodes," Materials Science and Engineering A 492 (2008) 191-198.*

Clark et al. 1988. Long-term stability of electroenzymatic glucose sensors implanted in mice. Trans Am Soc Artif Intern Organs 34:259-265.

Csoregi et al., 1994. Design, characterization, and one-point in vivo calibration of a subcutaneously implanted glucose electrode. Anal Chem. 66(19):3131-3138.

Feldman et al. 2003. A continuous glucose sensor based on wired enzyme technology—results from a 3-day trial in patients with type 1 diabetes. Diabetes Technol Ther 5(5):769-779.

Heller, "Electrical wiring of redox enzymes," Acc. Chem. Res., 23:128-134 (1990).

Heller, A. 1992. Electrical Connection of Enzyme Redox Centers to Electrodes. J. Phys. Chem. 96:3579-3587.

Hunter et al. Mar. 31, 2000. Minimally Invasive Glucose Sensor and Insulin Delivery System. MIT Home Automation and Healthcare Consortium. Progress Report No. 2-5. 17 pages.

Mancy et al. 1962. A galvanic cell oxygen analyzer. Journal of Electroanalytical Chemistry 4:65-92.

Mosbach et al. 1975. Determination of heat changes in the proximity of immobilized enzymes with an enzyme thermistor and its use for the assay of metabolites, Biochim. Biophys. Acta. 403:256-265.

Murphy, et al. 1992. Polymer membranes in clinical sensor applications. II. The design and fabrication of permselective hydrogels for electrochemical devices, Biomaterials, 13(14):979-990.

Quinn et al. 1995. Kinetics of glucose delivery to subcutaneous tissue in rats measured with 0.3-mm amperometric microsensors. The American Physiological Society E155-E161.

Quinn et al. 1997. Biocompatible, glucose-permeable hydrogel for in situ coating of implantable biosensors. Biomaterials 18:1665-1670.

Turner, A.P.F. 1988. Amperometric biosensor based on mediator-modified electrodes. Methods in Enzymology 137:90-103.

Wilkins et al. 1996. Glucose monitoring: state of the art and future possibilities. Med Eng Phys 18:273-288.

Yang et al (1996). "A glucose biosensor based on an oxygen electrode: In-vitro performances in a model buffer solution and in blood plasma," Biomedical Instrumentation & Technology, 30:55-61.

Yang et al. 1998. Development of needle-type glucose sensor with high selectivity. Science and Actuators B 46:249-256.

Zhu et al. 2002. Planar amperometric glucose sensor based on glucose oxidase immobilized by chitosan film on prussian blue layer. Sensors, 2:127-136.

ISR dated Feb. 10, 2011 for PCT/US2010/040842, filed Jul. 1, 2010.

IPRP and WO dated Jan. 4, 2012 for PCT/US2010/040842, filed Jul. 1, 2010.

PGM Database—Platinum—5.00% Iridium downloaded from http://pgmdatabase.com/jmpgm/index.jsp?record=1064 on Dec. 13, 2012, 1 page.

Altman et al., (1998) J. Biomedical Materials Research 43(1):21-37. Rotary bending fatigue of coils and wires used in cardiac lead design.

Ashby, Michael F. (2005), Chapter 13: Designing Hybrid Materials, pp. 339-357 in Materials Selection in Mechanical Design (3rd Edition), Elsevier.

Scheiner & Mortimer (1991) J. Biomedical Materials Research 25:589-608. A study of the fatigue properties of small diameter wires used in intramuscular electrodes.

Naoun et al. "Electrochemical study of the influence of $H_2O_2$ on 316L stainless steel implants in Hank's solution at body temperatures" *Matériaux & Techniques* 102, 102 (2014).

US 7,530,950, 05/2009, Brister et al. (withdrawn)

* cited by examiner

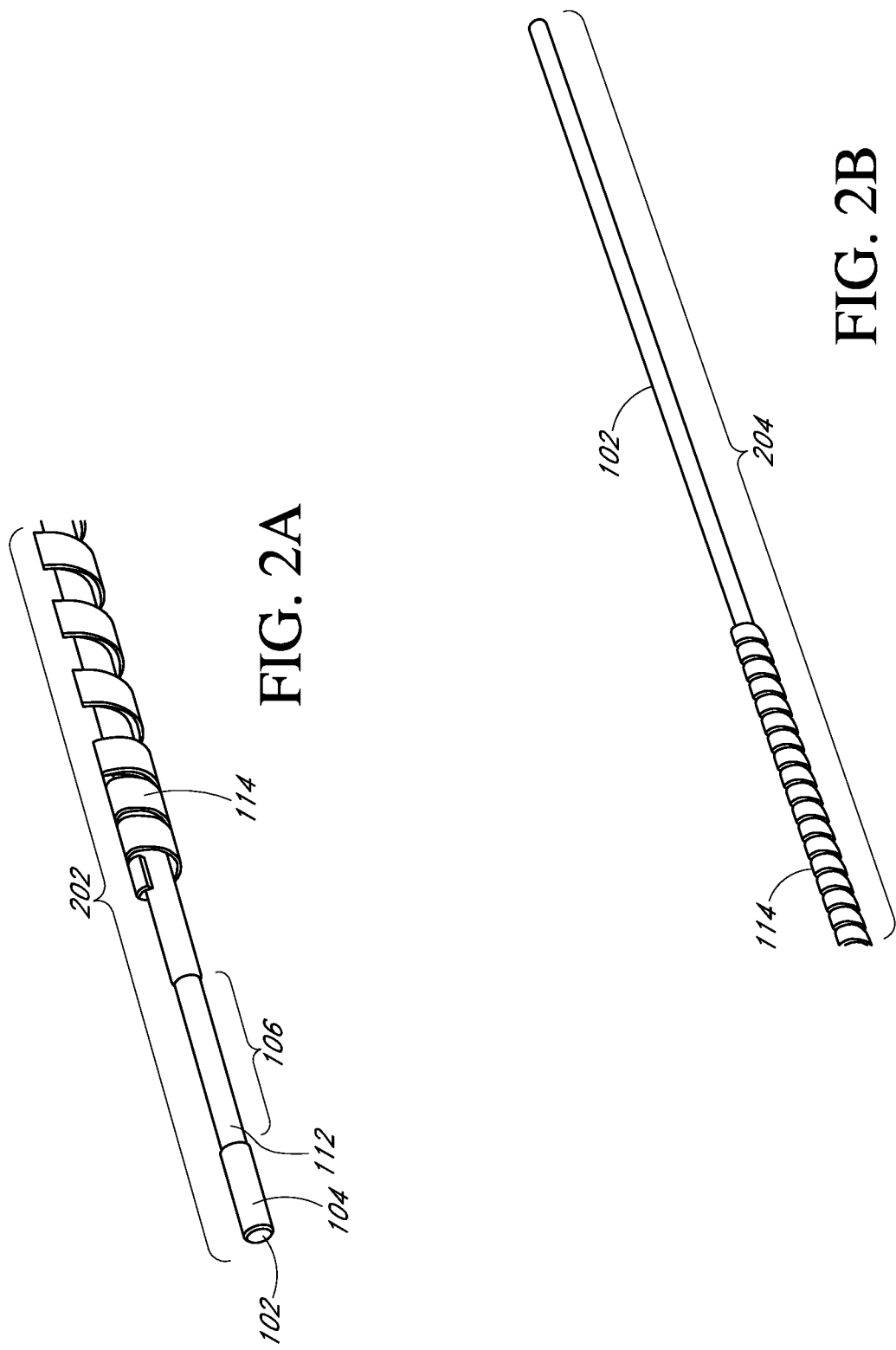

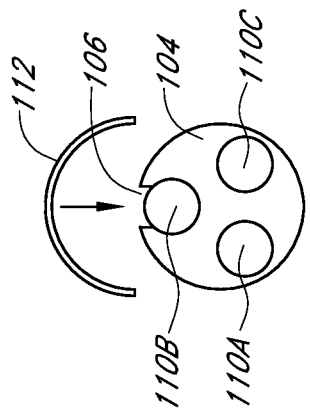
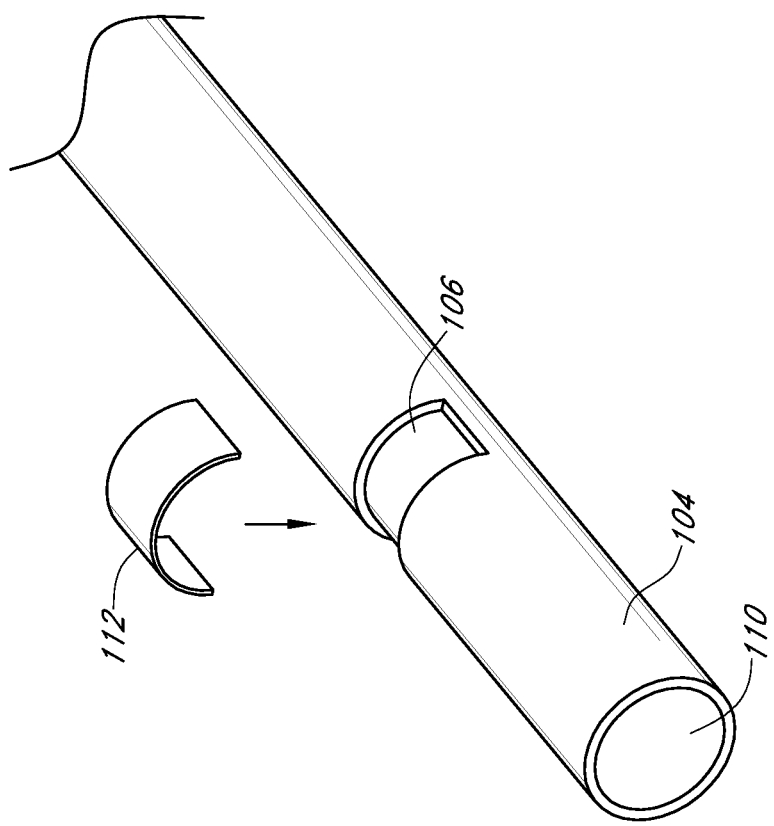

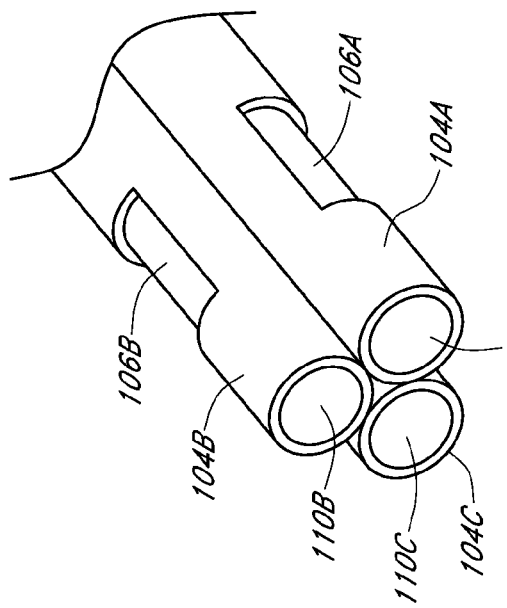
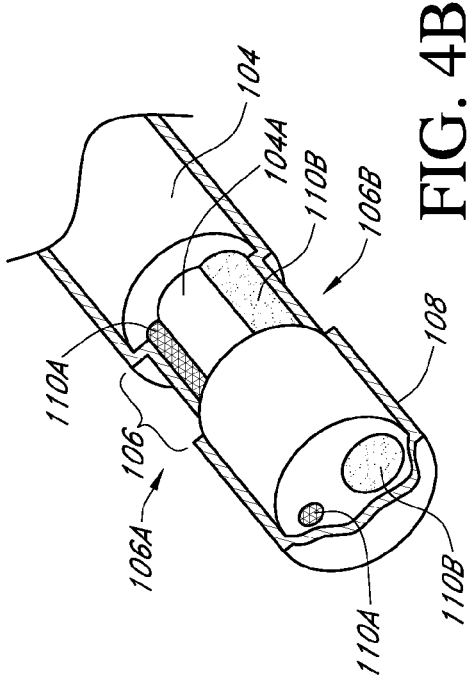
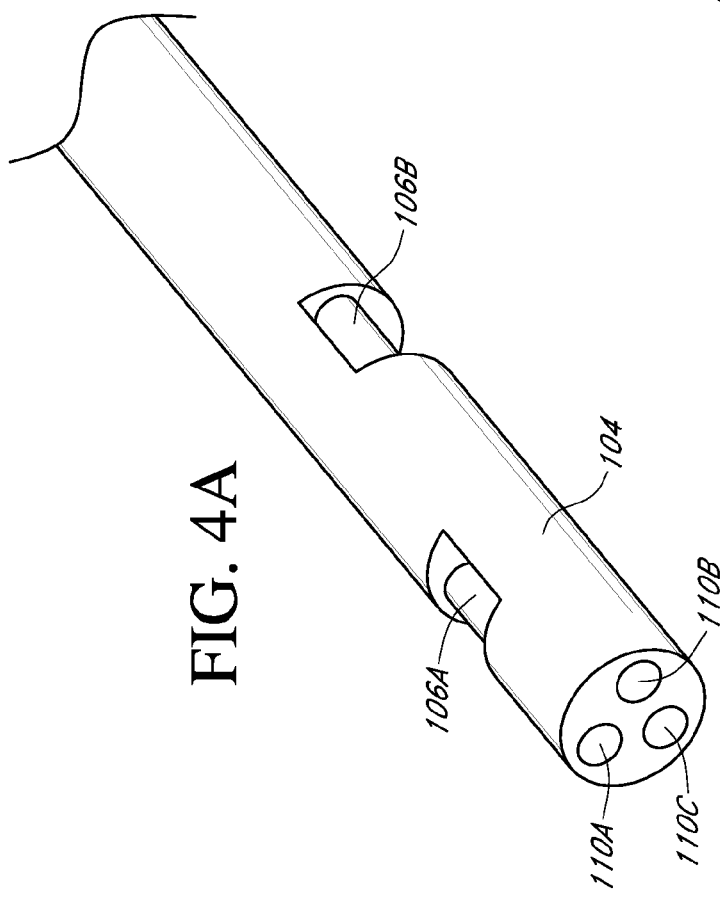
FIG. 4A
FIG. 4B
FIG. 4C

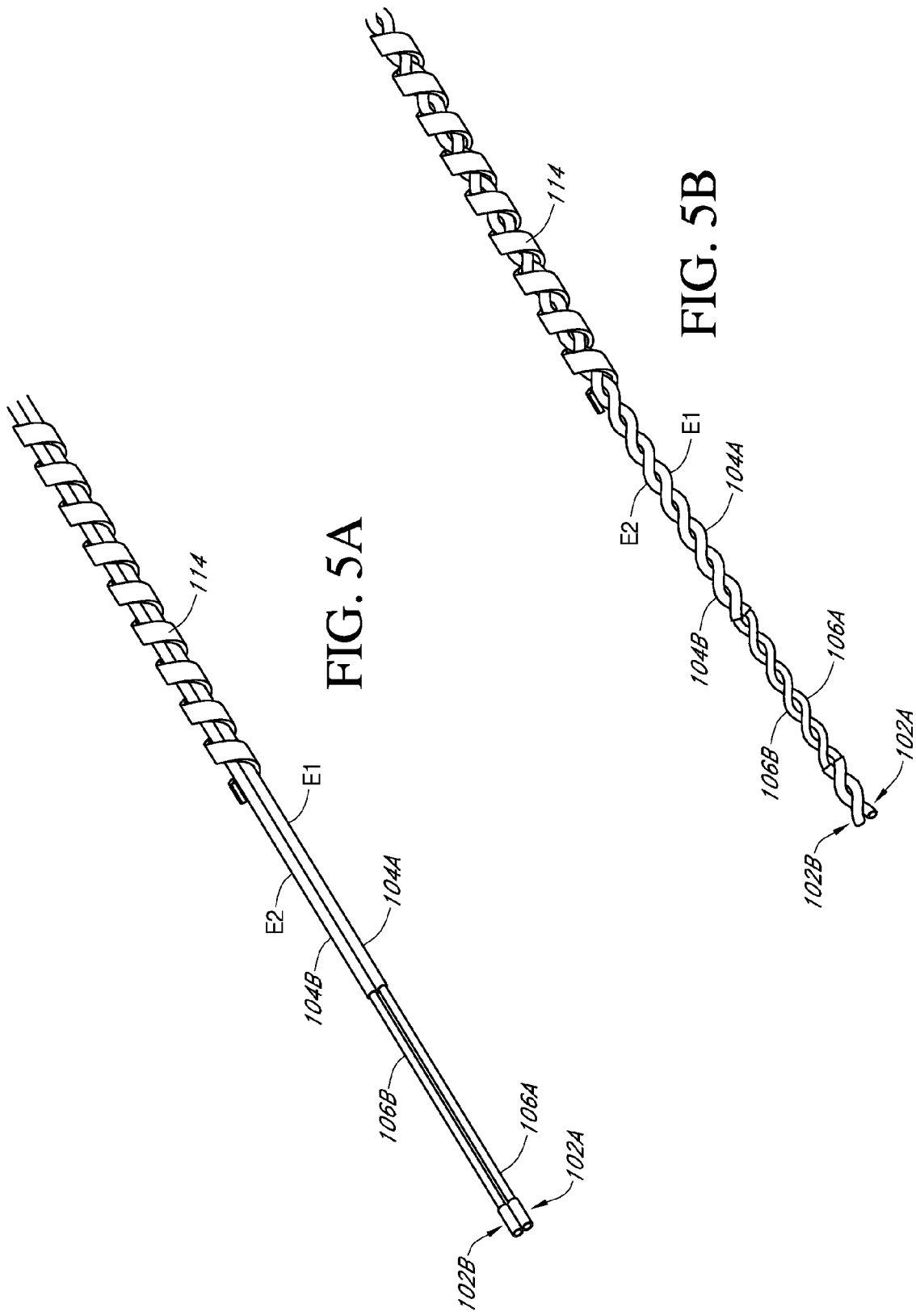

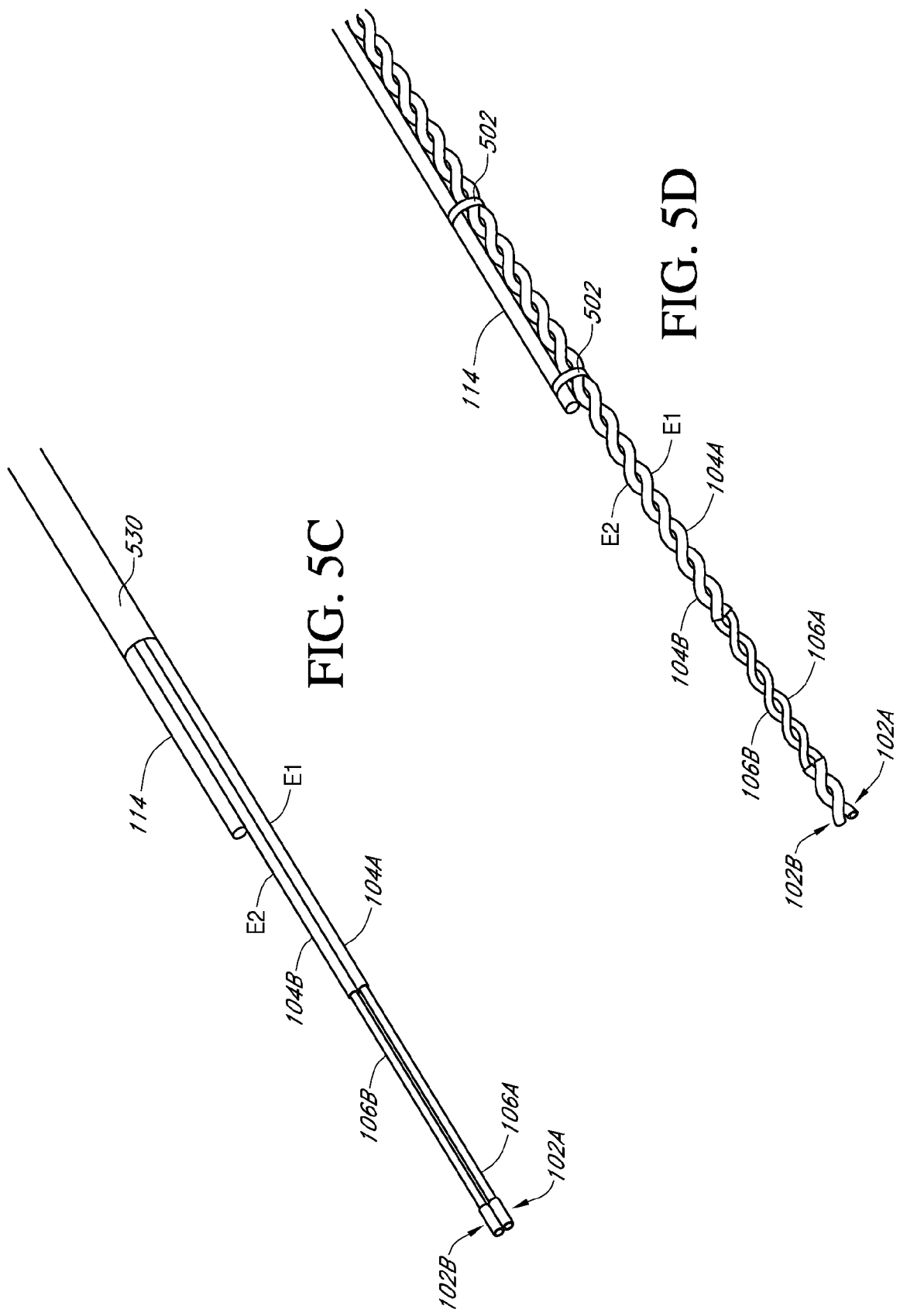

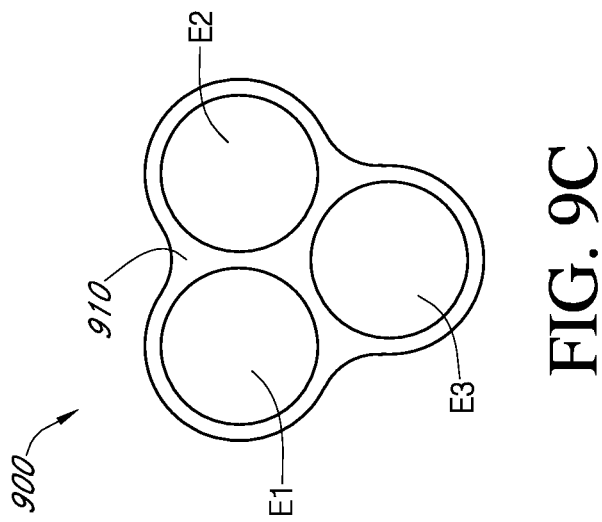
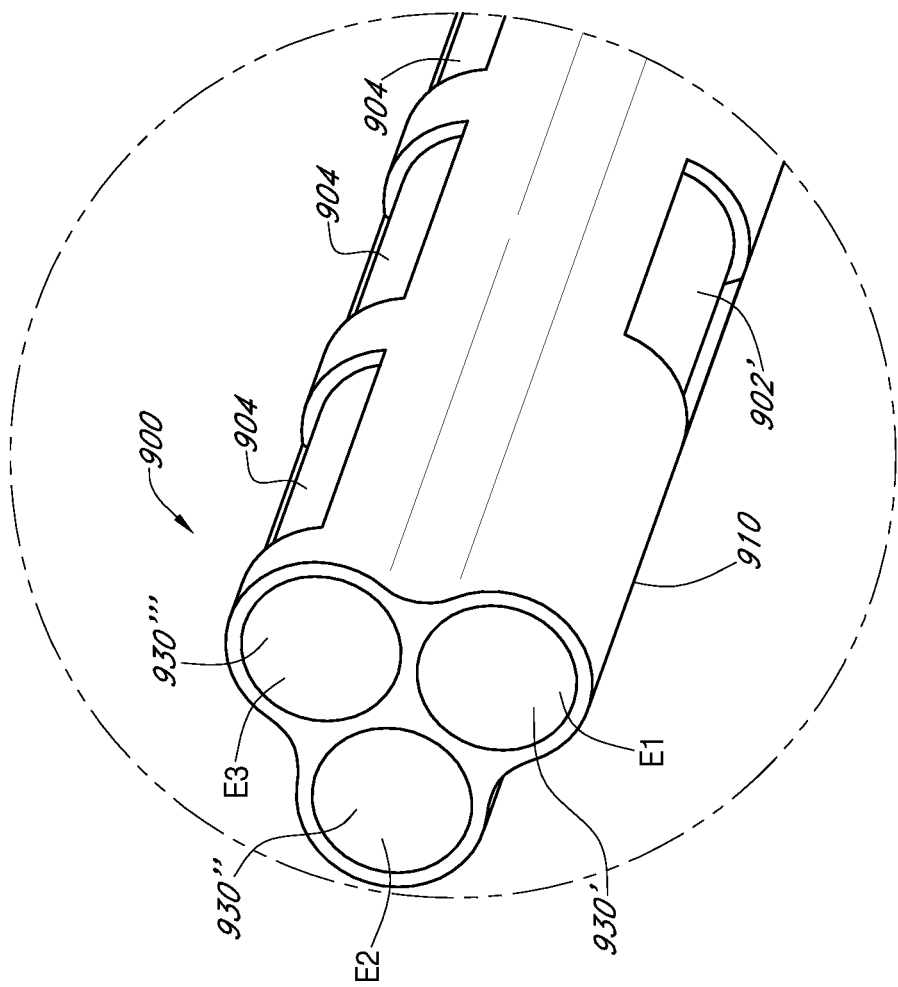
FIG. 9C
FIG. 9B

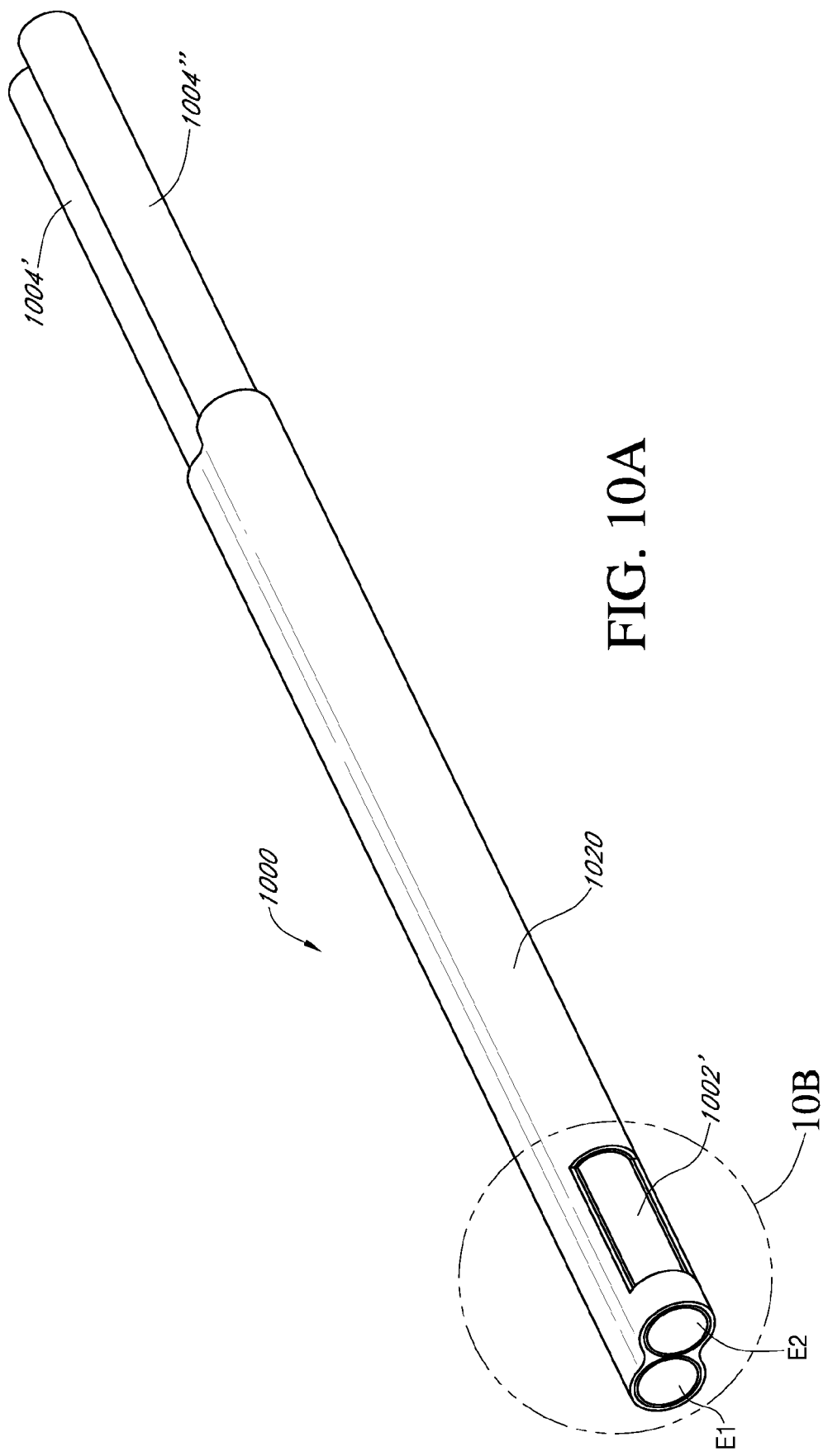

| Sensor No. | Test Sensors | Sensor No. | Conventional Sensors |
|---|---|---|---|
| | No. of Cycles | | No. of Cycles |
| 1 | 59 | 16 | 14 |
| 2 | 69 | 17 | 14 |
| 3 | 57 | 18 | 15 |
| 4 | 63 | 19 | 12 |
| 5 | 53 | 20 | 15 |
| 6 | 54 | 21 | 12 |
| 7 | 68 | 22 | 10 |
| 8 | 63 | 23 | 12 |
| 9 | 64 | 24 | 14 |
| 10 | 61 | 25 | 12 |
| 11 | 66 | 26 | 15 |
| 12 | 57 | 27 | 17 |
| 13 | 60 | 28 | 11 |
| 14 | 65 | 29 | 17 |
| 15 | 56 | 30 | 18 |

Comparison of Fatigue Life of Test Sensors and Conventional Sensors

FIG. 15

ANALYTE SENSORS AND METHODS OF MANUFACTURING SAME

CROSS-REFERENCE TO RELATED APPLICATIONS

This application claims the benefit of priority under 35 U.S.C. §119(e) of U.S. Provisional Application No. 61/222,716 filed Jul. 2, 2009, U.S. Provisional Application No. 61/222,815 filed Jul. 2, 2009, and U.S. Provisional Application No. 61/222,751 filed Jul. 2, 2009, the disclosures of which are hereby expressly incorporated by reference in their entirety and are hereby expressly made a portion of this application.

FIELD OF THE INVENTION

The embodiments described herein relate generally to continuous analyte sensors and methods of manufacturing the sensors.

BACKGROUND OF THE INVENTION

Electrochemical sensors are useful in chemistry and medicine to determine the presence or concentration of a biological analyte. Such sensors are useful, for example, to monitor glucose in diabetic patients and lactate during critical care events.

Diabetes mellitus is a disorder in which the pancreas cannot create sufficient insulin (Type I or insulin dependent) or in which insulin is not effective (Type 2 or non-insulin dependent). In the diabetic state, the victim suffers from high blood sugar, which causes an array of physiological derangements (e.g., kidney failure, skin ulcers, or bleeding into the vitreous of the eye) associated with the deterioration of small blood vessels. A hypoglycemic reaction (i.e., low blood sugar) can be induced by an inadvertent overdose of insulin, or after a normal dose of insulin or glucose-lowering agent, accompanied by extraordinary exercise or insufficient food intake.

The standard of care for a diabetic person involves measuring with a self-monitoring blood glucose (SMBG) monitor, which typically entails uncomfortable finger pricks. Due to the lack of comfort and convenience, a person with diabetes will often only measure his or her glucose level only two to four times per day when using a conventional SMBG monitor. Unfortunately, these time intervals may be spread so far apart such that the diabetic may find out too late of a hyperglycemic or hypoglycemic event, thereby potentially incurring dangerous side effects. Even if a diabetic manages to take a timely SMBG value, the diabetic may still not know whether his or her blood glucose value is increasing or decreasing based on conventional methods.

Heretofore, many implantable glucose sensors often suffer from complications within the body and provide only short-term or less-than-accurate measurement of blood glucose. Similarly, conventional transdermal sensors can have problems in accurately measuring and reporting back glucose values continuously over extended periods of time.

SUMMARY OF THE INVENTION

Accordingly, in a first aspect a continuous analyte sensor is provided, comprising: an elongated conductive body comprising a core and a first layer at least partially surrounding the core, wherein the first layer comprises a working electrode, and wherein the elongated conductive body is configured for multi-axis bending; and a membrane located over the working electrode.

In an embodiment of the first aspect, the core comprises at least one material selected from the group consisting of stainless steel, titanium, tantalum, and a polymer.

In an embodiment of the first aspect, the first layer comprises a conductive material selected from the group consisting of platinum, platinum-iridium, gold, palladium, iridium, alloys thereof, graphite, carbon, and a conductive polymer.

In an embodiment of the first aspect, the elongated conductive body further comprises a second layer at least partially surrounding the first layer.

In an embodiment of the first aspect, the second layer is an insulator.

In an embodiment of the first aspect, the sensor further comprises a third layer comprising a conductive material.

In an embodiment of the first aspect, the third layer is a reference electrode.

In an embodiment of the first aspect, the elongated conductive body further comprises an intermediate layer located between the core and the first layer.

In an embodiment of the first aspect, the intermediate layer comprises at least one component selected from the group consisting of an insulator, a conductor, a polymer, an adhesive, and combinations thereof.

In an embodiment of the first aspect, the core is a non-conductive polymer and the first layer is a conductive material.

In an embodiment of the first aspect, the conductive material is selected from the group consisting of platinum, platinum-iridium, gold, palladium, iridium, alloys thereof, graphite, carbon, and a conductive polymer.

In an embodiment of the first aspect, the membrane comprises a polymer having a Shore hardness of from about 70 A to about 55 D.

In an embodiment of the first aspect, the membrane comprises a resistance domain comprising a polymer having a Shore hardness of from about 70 A to about 55 D.

In an embodiment of the first aspect, the membrane further comprises an enzyme, and wherein the membrane is configured for detection or measurement of an analyte.

In an embodiment of the first aspect, the membrane comprises an outer layer comprising a polymer having a Shore hardness of from about 70 A to about 55 D.

In an embodiment of the first aspect, a thickness of the outer layer is at least about 25% of a thickness of the membrane.

In an embodiment of the first aspect, a fatigue life of the sensor is at least 1,000 cycles of flexing of from about 28° to about 110° at a bend radius of about 0.125-inches.

In an embodiment of the first aspect, an ultimate tensile strength of the elongated conductive body is from about 80 kPsi to about 500 kPsi.

In an embodiment of the first aspect, a Young's modulus of the elongated conductive body is from about 160 GPa to about 220 GPa.

In an embodiment of the first aspect, a yield strength of the elongated conductive body is at least 60 kPsi.

In an embodiment of the first aspect, a smallest dimension of the elongated conductive body is less than about 0.01 inches.

In an embodiment of the first aspect, the sensor is configured for in vivo implantation.

In an embodiment of the first aspect, the analyte is selected from the group consisting of albumin, alkaline phosphatase, alanine transaminase, aspartate aminotransferase, bilirubin, blood urea nitrogen, calcium, $CO_2$, chloride, creatinine, glucose, gamma-glutamyl transpeptidase, hematocrit, lactate, lactate dehydrogenase, magnesium, oxygen, pH, phosphorus, potassium, sodium, total protein, uric acid, a drug, a metabolic marker, and combinations thereof.

In an embodiment of the first aspect, the multi-axis bending comprises flexing in at least three directions.

In a second aspect, a continuous analyte sensor is provided, comprising: an elongated body comprising a conductive core and an insulating layer at least partially surrounding the conductive core, wherein the elongated body is configured for multi-axis bending; a working electrode body in electrical contact with the conductive core; and a membrane covering the working electrode body.

In an embodiment of the second aspect, the conductive core comprises an inner core and an outer core.

In an embodiment of the second aspect, the inner core is an insulating material, and wherein the outer core is a conductive material.

In an embodiment of the second aspect, the inner core is a first conductive material, and wherein the outer core is a second conductive material.

In an embodiment of the second aspect, the insulating layer comprises at least one polymer selected from the group consisting of polyurethane and polyimide.

In an embodiment of the second aspect, at least a portion of the working electrode body penetrates the insulating layer to provide the electrical contact between the working electrode body and the conductive core.

In an embodiment of the second aspect, the insulating layer comprises a window, and wherein at least a portion of the working electrode body is located in the window.

In an embodiment of the second aspect, the working electrode body comprises at least one material selected from the group consisting of platinum, platinum-iridium, gold, palladium, iridium, alloys thereof, graphite, carbon, and a conductive polymer.

In an embodiment of the second aspect, the membrane comprises a polymer having a Shore hardness of from about 70 A to about 55 D.

In an embodiment of the second aspect, the membrane comprises a resistance domain comprising a polymer having a Shore hardness of from about 70 A to about 55 D.

In an embodiment of the second aspect, the membrane further comprises an enzyme, and wherein the membrane is configured for detection or measurement of an analyte.

In an embodiment of the second aspect, the membrane comprises an outer layer comprising a polymer having a Shore hardness of from about 70 A to about 55 D.

In an embodiment of the second aspect, a thickness of the outer layer is at least about 25% of a thickness of the membrane.

In an embodiment of the second aspect, the sensor further comprises a reference electrode located on the elongated body.

In an embodiment of the second aspect, the reference electrode comprises a silver-containing polymer.

In an embodiment of the second aspect, a fatigue life of the sensor is at least 1,000 cycles of flexing of from about 28° to about 110° at a bend radius of about 0.125-inches.

In an embodiment of the second aspect, an ultimate tensile strength of the elongated body is from about 80 kPsi to about 500 kPsi.

In an embodiment of the second aspect, a Young's modulus of the elongated body is from about 160 GPa to about 220 GPa.

In an embodiment of the second aspect, a yield strength of the elongated body is at least about 60 kPsi.

In an embodiment of the second aspect, the smallest dimension of the elongated body is less than about 0.01 inches.

In an embodiment of the second aspect, the sensor is configured for in vivo implantation.

In an embodiment of the second aspect, the analyte is selected from the group consisting of albumin, alkaline phosphatase, alanine transaminase, aspartate aminotransferase, bilirubin, blood urea nitrogen, calcium, $CO_2$, chloride, creatinine, glucose, gamma-glutamyl transpeptidase, hematocrit, lactate, lactate dehydrogenase, magnesium, oxygen, pH, phosphorus, potassium, sodium, total protein, uric acid, a drug, a metabolic marker, and combinations thereof.

In an embodiment of the second aspect, the multi-axis bending comprises flexing in at least three directions.

In a third aspect, an analyte sensor is provided, comprising: an elongated body comprising an insulator, a first conductive core embedded in the insulator, and a second conductive core embedded in the insulator, wherein the insulator comprises a first window configured to expose an electroactive portion of the first conductive core, wherein the insulator further comprises a second window configured to expose an electroactive portion of the second conductive core, and wherein the elongated body is configured for multi-axis bending; and a membrane covering the exposed electroactive portion of the first conductive core.

In an embodiment of the third aspect, the first conductive core comprises at least one material selected from the group consisting of platinum, platinum-iridium, gold, palladium, iridium, graphite, carbon, a conductive polymer and alloys thereof.

In an embodiment of the third aspect, the first conductive core comprises an inner core and an outer core.

In an embodiment of the third aspect, the inner core comprises a material selected from the group consisting of stainless steel, titanium, tantalum and/or a polymer and wherein the outer core comprises platinum, platinum-iridium, gold, palladium, iridium, alloys thereof, graphite, carbon, and a conductive polymer.

In an embodiment of the third aspect, the second conductive core comprises a silver-containing material.

In an embodiment of the third aspect, the sensor further comprises a third conductive core embedded in the insulator.

In an embodiment of the third aspect, the membrane comprises a polymer having a Shore hardness of from about 70 A to about 55 D.

In an embodiment of the third aspect, the membrane comprises a resistance domain comprising a polymer having a Shore hardness of from about 70 A to about 55 D.

In an embodiment of the third aspect, the membrane further comprises an enzyme, and wherein the membrane is configured for detection or measurement of an analyte.

In an embodiment of the third aspect, the membrane comprises an outer layer comprising a polymer having a Shore hardness of from about 70 A to about 55 D.

In an embodiment of the third aspect, a thickness of the outer layer is at least about 25% of a thickness of the membrane.

In an embodiment of the third aspect, a fatigue life of the sensor is at least 1,000 cycles of flexing of from about 28° to about 110° at a bend radius of about 0.125-inches.

In an embodiment of the third aspect, an ultimate tensile strength of the elongated body is from about 80 kPsi to about 500 kPsi.

In an embodiment of the third aspect, a Young's modulus of the elongated body is from about 160 GPa to about 220 GPa.

In an embodiment of the third aspect, a yield strength of the elongated body is at least about 60 kPsi.

In an embodiment of the third aspect, a smallest dimension of the elongated body is less than about 0.01 inches.

In an embodiment of the third aspect, the insulator comprises at least one polymer selected from the group consisting of polyurethane and polyimide.

In an embodiment of the third aspect, the sensor is configured for in vivo implantation.

In an embodiment of the third aspect, the analyte is selected from the group consisting of albumin, alkaline phosphatase, alanine transaminase, aspartate aminotransferase, bilirubin, blood urea nitrogen, calcium, $CO_2$, chloride, creatinine, glucose, gamma-glutamyl transpeptidase, hematocrit, lactate, lactate dehydrogenase, magnesium, oxygen, pH, phosphorus, potassium, sodium, total protein, uric acid, a drug, a metabolic marker, and combinations thereof.

In an embodiment of the third aspect, the multi-axis bending comprises flexing in at least three directions.

In a fourth aspect, a continuous analyte sensor is provided, comprising: an elongated body comprising a nonconductive material, wherein the elongated body is configured for multi-axis bending; a working electrode located on the elongated body; a reference electrode located on the elongated body; and a membrane covering the working electrode.

In an embodiment of the fourth aspect, the elongated body is non-planar.

In an embodiment of the fourth aspect, the nonconductive material comprises a polymer.

In an embodiment of the fourth aspect, a fatigue life of the sensor is at least 1,000 cycles of flexing of from about 28° to about 110° at a bend radius of about 0.125-inches.

In an embodiment of the fourth aspect, an ultimate tensile strength of the elongated body is from about 80 kPsi to about 500 kPsi.

In an embodiment of the fourth aspect, a Young's modulus of the elongated body is from about 160 GPa to about 220 GPa.

In an embodiment of the fourth aspect, a yield strength of the elongated body is at least about 60 kPsi.

In an embodiment of the fourth aspect, a smallest dimension of the elongated body is less than about 0.01 inches.

In an embodiment of the fourth aspect, the working electrode comprises at least one material selected from the group consisting of platinum, platinum-iridium, gold, palladium, iridium, alloys thereof, graphite, carbon, and a conductive polymer.

In an embodiment of the fourth aspect, the reference electrode comprises a silver-containing polymer.

In an embodiment of the fourth aspect, the membrane comprises a polymer having a Shore hardness of from about 70 A to about 55 D.

In an embodiment of the fourth aspect, the membrane comprises a resistance domain comprising a polymer having a Shore hardness of from about 70 A to about 55 D.

In an embodiment of the fourth aspect, the membrane further comprises an enzyme, and wherein the membrane is configured for detection or measurement of an analyte.

In an embodiment of the fourth aspect, the membrane comprises an outer layer comprising a polymer having a Shore hardness of from about 70 A to about 55 D.

In an embodiment of the fourth aspect, a thickness of the outer layer is at least about 25% of a thickness of the membrane.

In an embodiment of the fourth aspect, the sensor is configured for in vivo implantation.

In an embodiment of the fourth aspect, the analyte is selected from the group consisting of at least one of albumin, alkaline phosphatase, alanine transaminase, aspartate aminotransferase, bilirubin, blood urea nitrogen, calcium, $CO_2$, chloride, creatinine, glucose, gamma-glutamyl transpeptidase, hematocrit, lactate, lactate dehydrogenase, magnesium, oxygen, pH, phosphorus, potassium, sodium, total protein, uric acid, a drug, a metabolic marker, and combinations thereof.

In an embodiment of the fourth aspect, the multi-axis bending comprises flexing in at least three directions.

In a fifth aspect, a method for making a flexible continuous analyte sensor adapted for in vivo use is provided, the method comprising: providing an elongated conductive body comprising a core, a conductive first layer and an insulating second layer, wherein the elongated conductive body is configured for multi-axis bending; exposing a working electrode on the conductive first layer; and applying a membrane on the working electrode, whereby a flexible continuous analyte sensor configured for multi-axis bending is obtained.

In an embodiment of the fifth aspect, the step of exposing the working electrode comprises removing a portion of the insulating second layer.

In an embodiment of the fifth aspect, the step of removing a portion of the insulating second layer comprises ablating the portion of the insulating second layer.

In an embodiment of the fifth aspect, the method further comprises forming a reference electrode on the elongated conductive body.

In an embodiment of the fifth aspect, the step of forming the reference electrode comprises applying at least one of a silver-containing ink, a silver-containing paint, and a silver-containing paste.

In an embodiment of the fifth aspect, applying comprises using a thin film technique or a thick film technique.

In an embodiment of the fifth aspect, applying comprises pad printing.

In an embodiment of the fifth aspect, the method further comprises applying an ex vivo insulator on a portion of the reference electrode.

In an embodiment of the fifth aspect, the step of applying an ex vivo insulator comprises pad printing a dielectric material.

In an embodiment of the fifth aspect, the step of applying the membrane comprises applying a polymer having a Shore hardness of from about 70 A to about 55 D.

In an embodiment of the fifth aspect, the step of applying the membrane comprises forming a resistance domain from a polymer having a Shore hardness of from about 70 A to about 55 D.

In an embodiment of the fifth aspect, the step of applying the membrane further comprises applying an enzyme, wherein the membrane is configured for detection or measurement of an analyte.

In an embodiment of the fifth aspect, the step of applying the membrane comprises forming an outer layer comprising a polymer having a Shore hardness of from about 70 A to about 55 D.

In an embodiment of the fifth aspect, a thickness of the outer layer is at least about 25% of a thickness of the membrane.

In an embodiment of the fifth aspect, at least one step is semi-automated.

In an embodiment of the fifth aspect, at least one step is fully-automated.

In an embodiment of the fifth aspect, a fatigue life of the sensor is at least 1,000 cycles of flexing of from about 28° to about 110° at a bend radius of about 0.125-inches.

In an embodiment of the fifth aspect, an ultimate tensile strength of the elongated conductive body is from about 80 kPsi to about 500 kPsi.

In an embodiment of the fifth aspect, a Young's modulus of the elongated conductive body is from about 160 GPa to about 220 GPa.

In an embodiment of the fifth aspect, a yield strength of the elongated conductive body is at least about 60 kPsi.

In an embodiment of the fifth aspect, a smallest dimension of the elongated conductive body is less than about 0.01 inches.

In an embodiment of the fifth aspect, the insulating layer comprises at least one polymer selected from the group consisting of polyurethane and polyimide.

In a sixth aspect, a method for making a flexible continuous analyte sensor adapted for in vivo use is provided, the method comprising: providing an elongated conductive body comprising a core, a first conductive layer, an insulating layer, and a second conductive layer comprising a silver-containing material, wherein the elongated conductive body is configured for multi-axis bending; exposing a working electrode on the first conductive layer; and applying a membrane over the working electrode, whereby a flexible continuous analyte sensor configured for multi-axis bending is obtained.

In an embodiment of the sixth aspect, the step of exposing the working electrode comprises removing a portion of the insulating layer and a portion of the second conductive layer.

In an embodiment of the sixth aspect, the step of removing a portion of the insulating layer and a portion of the second conductive layer comprises laser ablating the portion of the insulating layer and the portion of the second conductive layer.

In an embodiment of the sixth aspect, the method further comprises applying an ex vivo insulator on a portion of the second conductive layer.

In an embodiment of the sixth aspect, the step of applying an ex vivo insulator comprises pad printing a dielectric material.

In an embodiment of the sixth aspect, the step of forming the membrane comprises applying a polymer having a Shore hardness of from about 70 A to about 55 D.

In an embodiment of the sixth aspect, the step of applying the membrane comprises applying a polymer having a Shore hardness of from about 70 A to about 55 D.

In an embodiment of the sixth aspect, the step of applying the membrane comprises forming a resistance domain from a polymer having a Shore hardness of from about 70 A to about 55 D.

In an embodiment of the sixth aspect, the step of applying the membrane further comprises applying an enzyme, wherein the membrane is configured for detection or measurement of an analyte.

In an embodiment of the sixth aspect, the step of applying the membrane comprises forming an outer layer comprising a polymer having a Shore hardness of from about 70 A to about 55 D.

In an embodiment of the sixth aspect, a thickness of the outer layer is at least about 25% of a thickness of the membrane.

In an embodiment of the sixth aspect, at least one step is semi-automated.

In an embodiment of the sixth aspect, at least one step is fully-automated.

In an embodiment of the sixth aspect, a fatigue life of sensor is at least 1,000 cycles of flexing of from about 28° to about 110° at a bend radius of about 0.125-inches.

In an embodiment of the sixth aspect, an ultimate tensile strength of the elongated conductive body is from about 80 kPsi to about 500 kPsi.

In an embodiment of the sixth aspect, a Young's modulus of the elongated conductive body is from about 160 GPa to about 220 GPa.

In an embodiment of the sixth aspect, a yield strength of the elongated conductive body is at least about 60 kPsi.

In an embodiment of the sixth aspect, a smallest dimension of the elongated conductive body is less than about 0.01 inches.

In an embodiment of the sixth aspect, the insulating layer comprises at least one polymer selected from the group consisting of polyurethane and polyimide.

In a seventh aspect, a method for making a flexible continuous analyte sensor adapted for in vivo use is provided, the method comprising: applying a working electrode to an insulated conductive body comprising a conductive core and an insulating layer located on the conductive core, wherein the working electrode is electrically connected to the conductive core; and applying a membrane on the working electrode, whereby a flexible continuous analyte sensor configured for multi-axis bending is obtained.

In an embodiment of the seventh aspect, the step of applying the working electrode comprises exposing a portion of the conductive core.

In an embodiment of the seventh aspect, the step of exposing a portion of the conductive core comprises removing a portion of the insulating layer.

In an embodiment of the seventh aspect, the step of removing a portion of the insulating layer comprises ablating the portion of the insulating layer.

In an embodiment of the seventh aspect, the step of applying the working electrode further comprises applying the working electrode on the exposed portion of the conductive core.

In an embodiment of the seventh aspect, the step of applying the working electrode further comprises intersecting the insulating layer with a portion of the working electrode.

In an embodiment of the seventh aspect, the method further comprises disposing a reference electrode on the insulated conductive body.

In an embodiment of the seventh aspect, the step of disposing the reference electrode comprises applying at least one of a silver-containing ink, a silver-containing paint, and a silver-containing paste.

In an embodiment of the seventh aspect, the step of applying comprises a thin film technique or a thick film technique.

In an embodiment of the seventh aspect, the step of applying comprises pad printing.

In an embodiment of the seventh aspect, the method further comprises applying an ex vivo insulator on a portion of the reference electrode.

In an embodiment of the seventh aspect, the step of applying an ex vivo insulator comprises pad printing a dielectric material.

In an embodiment of the seventh aspect, the step of applying the membrane comprises applying a polymer having a Shore hardness of from about 70 A to about 55 D.

In an embodiment of the seventh aspect, the step of applying the membrane comprises forming a resistance domain from a polymer having a Shore hardness of from about 70 A to about 55 D.

In an embodiment of the seventh aspect, the step of applying the membrane further comprises applying an enzyme, wherein the membrane is configured for detection or measurement of an analyte.

In an embodiment of the seventh aspect, the step of applying the membrane comprises forming an outer layer comprising a polymer having a Shore hardness of from about 70 A to about 55 D.

In an embodiment of the seventh aspect, a thickness of the outer layer is at least about 25% of a thickness of the membrane.

In an embodiment of the seventh aspect, at least one step is semi-automated.

In an embodiment of the seventh aspect, at least one step is fully-automated.

In an eighth aspect, a method for making a flexible continuous analyte sensor adapted for in vivo use is provided, the method comprising: providing an elongated body comprising an insulator, a first conductive core embedded in the insulator, and a second conductive core embedded in the insulator; removing a portion of the insulator to expose a working electrode located on the first conductive core; removing a portion of the insulator to expose a reference electrode on the second conductive core; and applying a membrane on the working electrode, whereby a flexible continuous analyte sensor configured for multi-axis bending is obtained.

In an embodiment of the eighth aspect, at least one step of removing comprises ablating.

In an embodiment of the eighth aspect, the step of applying a membrane comprises applying a polymer having a Shore hardness of from about 70 A to about 55 D.

In an embodiment of the eighth aspect, the step of applying a membrane comprises forming a resistance domain from a polymer having a Shore hardness of from about 70 A to about 55 D.

In an embodiment of the eighth aspect, the step of forming a membrane comprises forming an enzyme domain comprising an enzyme, wherein the membrane is configured for detection or measurement of an analyte.

In an embodiment of the eighth aspect, at least one step is semi-automated.

In an embodiment of the eighth aspect, at least one step is fully-automated.

In an embodiment of the eighth aspect, a fatigue life of the sensor is at least 1,000 cycles of flexing of from about 28° to about 110° at a bend radius of about 0.125-inches.

In an embodiment of the eighth aspect, an ultimate tensile strength of the elongated body is from about 80 kPsi to about 500 kPsi.

In an embodiment of the eighth aspect, a Young's modulus of the elongated body is from about 160 GPa to about 220 GPa.

In an embodiment of the eighth aspect, a yield strength of the elongated body is at least about 60 kPsi.

In an embodiment of the eighth aspect, a smallest dimension of the elongated body is less than about 0.01 inches.

In an embodiment of the eighth aspect, the insulator comprises at least one polymer selected from the group consisting of polyurethane and polyimide.

In a ninth aspect, a method for making a flexible continuous analyte sensor adapted for in vivo use is provided, the method comprising: providing an elongated body comprising a nonconductive material; applying a working electrode on the elongated body; applying a reference electrode on the elongated body; and covering the working electrode with a membrane, whereby a flexible continuous analyte sensor configured for multi-axis bending is obtained.

In an embodiment of the ninth aspect, the elongated body is non-planar.

In an embodiment of the ninth aspect, the step of applying a working electrode comprises depositing a conductive material on the elongated body.

In an embodiment of the ninth aspect, the step of depositing the conductive material comprises depositing the conductive material using at least one of a thick film deposition technique and a thin film deposition technique.

In an embodiment of the ninth aspect, the step of depositing the conductive material comprises printing the conductive material.

In an embodiment of the ninth aspect, the step of depositing the conductive material comprises plating the conductive material.

In an embodiment of the ninth aspect, the step of applying a reference electrode comprises depositing a silver-containing material on the elongated body.

In an embodiment of the ninth aspect, the step of depositing the silver-containing material uses at least one of a thick film deposition technique and a thin film deposition technique.

In an embodiment of the ninth aspect, the step of depositing the silver-containing material comprises depositing a silver-containing polymer.

In an embodiment of the ninth aspect, the step of depositing the silver-containing material comprises printing the silver-containing material.

In an embodiment of the ninth aspect, the step of depositing the silver-containing material comprises plating the silver-containing material.

In an embodiment of the ninth aspect, the step of applying a membrane comprises applying a polymer having a Shore hardness of from about 70 A to about 55 D.

In an embodiment of the ninth aspect, the step of applying a membrane comprises forming a resistance domain from a polymer having a Shore hardness of from about 70 A to about 55 D.

In an embodiment of the ninth aspect, the step of forming a membrane comprises forming an enzyme domain comprising an enzyme, wherein the membrane is configured for detection or measurement of an analyte.

In an embodiment of the ninth aspect, at least one step is semi-automated.

In an embodiment of the ninth aspect, at least one step is fully-automated.

In an embodiment of the ninth aspect, a fatigue life of the sensor is at least 1,000 cycles of flexing of from about 28° to about 110° at a bend radius of about 0.125-inches.

In an embodiment of the ninth aspect, an ultimate tensile strength of the non-planar elongated body is from about 80 kPsi to about 500 kPsi.

In an embodiment of the ninth aspect, a Young's modulus of the non-planar, elongated body is from about 160 GPa to about 220 GPa.

In an embodiment of the ninth aspect, a yield strength of the elongated body is at least about 60 kPsi.

In an embodiment of the ninth aspect, the smallest dimension of the elongated body is less than about 0.01 inches.

In a tenth aspect, a continuous analyte sensor is provided, comprising: an elongated conductive body comprising a conductive core and a stepped surface comprising a base portion and at least one stepped portion, the elongated conductive body configured for multi-axis bending; and a membrane located over the elongated conductive body.

In an embodiment of the tenth aspect, the base portion comprises a conductive core surface.

In an embodiment of the tenth aspect, the at least one stepped portion comprises a first stepped portion having a first thickness.

In an embodiment of the tenth aspect, wherein the first stepped portion comprises an insulating layer.

In an embodiment of the tenth aspect, wherein the at least one stepped portion further comprises a second stepped portion having a second thickness.

In an embodiment of the tenth aspect, the second thickness is greater than the first thickness.

In an embodiment of the tenth aspect, wherein the second stepped portion comprises the insulating layer and a conducting layer.

In an embodiment of the tenth aspect, wherein the at least one stepped portion further comprises a third stepped portion having a third thickness.

In an embodiment of the tenth aspect, the third thickness is greater than the second thickness.

In an embodiment of the tenth aspect, wherein the third stepped portion comprises the insulating layer and the conducting layer.

In an eleventh embodiment, a sensor system configured for measurement of an analyte in a host is provided, the sensor system comprising: a catheter; and a sensor comprising an elongated conductive body and a supporting member configured to support the elongated conductive body when the elongated conductive body is subject to bending forces, wherein the sensor is configured to reside in the catheter when the catheter is inserted in a host's blood vessel.

In an embodiment of the eleventh aspect, the catheter and sensor are configured such that when inserted in the host, a first portion of the supporting member extends outside of the host's body from where the catheter exits the host's body, wherein the first portion has a length of up to about 1 cm.

In an embodiment of the eleventh aspect, the catheter and sensor are configured such that when inserted in the host, a second portion of the supporting member extends into the host's body from where the catheter enters the host's body, wherein the second portion has a length of up to about 1 cm.

In an embodiment of the eleventh aspect, the catheter and sensor are configured such that when inserted in the host, a first portion of the supporting member extends outside of the host's body from where the catheter exits the host's body, wherein the first portion has a length of from about 1 mm to about 1 cm.

In an embodiment of the eleventh aspect, the catheter and sensor are configured such that when inserted in the host, a second portion of the supporting member extends into the host's body from where the catheter enters the host's body, wherein the second portion has a length of from about 1 mm to about 1 cm.

In an embodiment of the eleventh aspect, the supporting member supports at least about 50% of a length of the elongated conductive body.

In an embodiment of the eleventh aspect, the catheter further comprises a hub, and wherein at least a portion of the supporting member extends beyond the hub.

In an embodiment of the eleventh aspect, the catheter further comprises a connector, and wherein at least a portion of the supporting member extends beyond the connector.

In an embodiment of the eleventh aspect, the catheter and sensor are configured such that when inserted in the host, the supporting member extends from an exit site of the catheter from the host's body by a distance sufficient to provide support to the elongated conductive body at the exit site.

In an embodiment of the eleventh aspect, the supporting member supports at least about 50% of a length of the elongated conductive body, wherein a first end of the elongated conductive body is left exposed to permit electrochemical reaction when inserted in a host's blood vessel, and wherein a second end of the elongated conductive body is exposed to permit electrical connection to sensor electronics.

In an embodiment of the eleventh aspect, the sensor system is configured for insertion near a joint of the host, and wherein the supporting member extends sufficiently from an exit site of the catheter to protect the elongated conductive body at a point of articulation of the joint.

In an embodiment of the eleventh aspect, the sensor system is configured for insertion near a joint of the host, and wherein the supporting member extends sufficiently from an exit site of the catheter to protect the elongated conductive body at a point of bending of the catheter.

In a twelfth aspect, a sensor configured for measurement of an analyte in a host is provided, the sensor comprising: an elongated conductive body; and a supporting member configured to support the elongated conductive body when the elongated conductive body is subject to bending forces when inserted in a host's skin.

In an embodiment of the twelfth aspect, the sensor is configured such that when inserted in the host's skin, a first portion of the supporting member extends out of the host's skin, the first portion having a length of up to about 1 cm.

In an embodiment of the twelfth aspect, the sensor is configured such that when inserted in the host's skin, a second portion of the supporting member extends into the host's tissue, the second portion having a length of up to about 1 cm.

In an embodiment of the twelfth aspect, the sensor is configured such that when inserted in the host's skin, a first portion of the supporting member extends out of the host's skin, the first portion having a length of from about 1 mm to about 1 cm.

In an embodiment of the twelfth aspect, the sensor is configured such that when inserted in the host's skin, a second portion of the supporting member extends into the host's tissue, the second portion having a length of from about 1 mm to about 1 cm.

In an embodiment of the twelfth aspect, the supporting member supports at least about 50% of a length of the elongated conductive body.

In an embodiment of the twelfth aspect, the sensor is configured such that when inserted in the host's skin, the supporting member extends from an exit site in the host's skin by a distance sufficient to provide support to the elongated conductive body at the exit site.

In an embodiment of the twelfth aspect, the supporting member supports at least about 50% of a length of the elongated conductive body, wherein a first end of the elongated conductive body is left exposed to permit electrochemical reaction when inserted in the host's tissue, and wherein a second end of the elongated conductive body is exposed to permit electrical connection to sensor electronics.

In an embodiment of the twelfth aspect, the sensor is configured for insertion in the host's skin near a joint of the host, and wherein the supporting member extends sufficiently from an exit site in the host's skin to protect the elongated conductive body at a point of articulation of the joint.

In a thirteenth aspect, a continuous analyte sensor is provided, the continuous analyte sensor comprising: an elongated core comprising a working electrode; an insulating layer covering at least a portion of the elongated core; a conductive layer comprising a reference electrode or a counter electrode, wherein the conductive layer covers at least a portion of the insulating layer; and a membrane covering at least a portion the working electrode.

In an embodiment of the thirteenth aspect, the elongated core comprises an elongated body and a layer of conductive material covering at least a portion of the elongated body.

In an embodiment of the thirteenth aspect, the membrane comprises a polymer having a Shore hardness of from about 70 A to about 55 D.

In an embodiment of the thirteenth aspect, the continuous analyte sensor has an ultimate tensile strength of from about 80 kPsi to about 500 kPsi.

In an embodiment of the thirteenth aspect, the continuous analyte sensor has an ultimate tensile strength of from about 150 kPsi to about 280 kPsi.

In an embodiment of the thirteenth aspect, the continuous analyte sensor has a Young's modulus of from about 160 GPa to about 220 GPa.

In an embodiment of the thirteenth aspect, the continuous analyte sensor has a yield strength of at least 60 kPsi.

In an embodiment of the thirteenth aspect, the continuous analyte sensor has a fatigue life of at least 1,000 cycles of flexing of from about 28° to about 110° at a bend radius of about 0.125-inches.

In an embodiment of the thirteenth aspect, the continuous analyte sensor is configured for multi-axis bending.

In an embodiment of the thirteenth aspect, the multi-axis bending is associated with flexing in at least three directions.

In an embodiment of the thirteenth aspect, the conductive layer comprises a silver-containing material.

In an embodiment of the thirteenth aspect, the silver-containing material has a particle size associated with a maximum particle dimension that is less than about 100 microns.

In an embodiment of the thirteenth aspect, the silver-containing material has a particle shape that is substantially spherical.

In an embodiment of the thirteenth aspect, the continuous analyte sensor has a cross-sectional radius of from about 5 microns to about 200 microns.

In an embodiment of the thirteenth aspect, the continuous analyte sensor has a fatigue life of at least 20 cycles of flexing of from about 45° to about −45° at a bend radius of about 0.031-inches.

In an embodiment of the thirteenth aspect, the continuous analyte sensor has a fatigue life of at least 40 cycles of flexing of from about 45° to about −45° at a bend radius of about 0.031-inches.

In an embodiment of the thirteenth aspect, the continuous analyte sensor has a fatigue life of at least 50 cycles of flexing of from about 45° to about −45° at a bend radius of about 0.031-inches.

In an embodiment of the thirteenth aspect, the continuous analyte sensor has a fatigue life of at least 60 cycles of flexing of from about 45° to about −45° at a bend radius of about 0.031-inches.

In an embodiment of the thirteenth aspect, the continuous analyte sensor has a fatigue life of at least 65 cycles of flexing of from about 45° to about −45° at a bend radius of about 0.031-inches.

In a fourteenth aspect, a continuous analyte sensor is provided configured for in vivo use, the continuous analyte sensor comprising: an elongated conductive body comprising a working electrode, wherein the elongated conductive body has a Young's modulus of from about 160 GPa to about 220 GPa and a yield strength of at least 60 kPsi; and a membrane covering at least a portion of the working electrode.

In an embodiment of the fourteenth aspect, the elongated conductive body comprises an elongated core, an insulating layer covering at least a portion of the elongated core, a conductive layer comprising a reference electrode or a counter electrode and covering at least a portion of the insulating layer, and a membrane covering at least a portion the working electrode.

In an embodiment of the fourteenth aspect, the elongated core comprises an elongated body and a layer of conductive material covering at least a portion of the elongated body.

In an embodiment of the fourteenth aspect, the elongated body comprises at least one material selected from the group consisting of stainless steel, titanium, tantalum, and a polymer.

In an embodiment of the fourteenth aspect, the layer of conductive material covering at least a portion of the elongated body comprises a conductive material selected from the group consisting of platinum, platinum-iridium, gold, palladium, iridium, alloys thereof, graphite, carbon, and a conductive polymer.

In an embodiment of the fourteenth aspect, the conductive layer comprising the reference electrode or the counter electrode comprises a silver-containing material.

In an embodiment of the fourteenth aspect, the silver-containing material has a particle size associated with a maximum particle dimension that is less than about 100 microns.

In an embodiment of the fourteenth aspect, the silver-containing material has a particle shape that is substantially spherical.

In an embodiment of the fourteenth aspect, the insulating layer comprises at least one polymer selected from the group consisting of polyurethane and polyimide.

In an embodiment of the fourteenth aspect, a ratio of a thickness of the conductive layer to a thickness of insulating layer is from about 1:5 to about 1:1.

In an embodiment of the fourteenth aspect, the conductive material is a silver-containing material.

In an embodiment of the fourteenth aspect, the membrane comprises a polymer having a Shore hardness of from about 70 A to about 55 D.

In an embodiment of the fourteenth aspect, the continuous analyte sensor has an ultimate tensile strength of from about 80 kPsi to about 500 kPsi.

In an embodiment of the fourteenth aspect, the continuous analyte sensor has an ultimate tensile strength of from about 150 kPsi to about 280 kPsi.

In an embodiment of the fourteenth aspect, the continuous analyte sensor has a fatigue life of at least 1,000 cycles of flexing of from about 28° to about 110° at a bend radius of about 0.125-inches.

In an embodiment of the fourteenth aspect, the continuous analyte sensor is configured for multi-axis bending.

In an embodiment of the fourteenth aspect, the multi-axis bending is associated with flexing in at least three directions.

In an embodiment of the fourteenth aspect, the elongated conductive body has a diameter of from about 50 microns to about 250 microns.

In an embodiment of the fourteenth aspect, the sensor has a cross-sectional radius of from about 5 microns to about 200 microns.

In an embodiment of the fourteenth aspect, the continuous analyte sensor has a fatigue life of at least 20 cycles of flexing of from about 45° to about −45° at a bend radius of about 0.031-inches.

In an embodiment of the fourteenth aspect, the continuous analyte sensor has a fatigue life of at least 40 cycles of flexing of from about 45° to about −45° at a bend radius of about 0.031-inches.

In an embodiment of the fourteenth aspect, the continuous analyte sensor has a fatigue life of at least 50 cycles of flexing of from about 45° to about −45° at a bend radius of about 0.031-inches.

In an embodiment of the fourteenth aspect, the continuous analyte sensor has a fatigue life of at least 60 cycles of flexing of from about 45° to about −45° at a bend radius of about 0.031-inches.

In an embodiment of the fourteenth aspect, the continuous analyte sensor has a fatigue life of at least 65 cycles of flexing of from about 45° to about −45° at a bend radius of about 0.031-inches.

In a fifteenth embodiment, a continuous analyte sensor is provided configured for in vivo use, the continuous analyte sensor comprising: an elongated conductive body comprising a working electrode; and a membrane covering at least a portion of the working electrode; wherein the continuous analyte sensor has a fatigue life of at least 20 cycles of flexing of from about 45° to about −45° at a bend radius of about 0.031-inches.

In an embodiment of the fifteenth aspect, the elongated conductive body comprises an elongated core, an insulating layer covering at least a portion of the elongated core, a conductive layer comprising a reference electrode or a counter electrode and covering at least a portion of the insulating layer, and a membrane covering at least a portion the working electrode.

In an embodiment of the fifteenth aspect, the elongated core comprises an elongated body and a layer of conductive material covering at least a portion of the elongated body.

In an embodiment of the fifteenth aspect, the elongated body comprises at least one material selected from the group consisting of stainless steel, titanium, tantalum, and a polymer.

In an embodiment of the fifteenth aspect, the layer of conductive material covering at least a portion of the elongated body comprises a conductive material selected from the group consisting of platinum, platinum-iridium, gold, palladium, iridium, alloys thereof, graphite, carbon, and a conductive polymer.

In an embodiment of the fifteenth aspect, the conductive layer comprising the reference electrode or the counter electrode comprises a silver-containing material.

In an embodiment of the fifteenth aspect, the silver-containing material has a particle size associated with a maximum particle dimension that is less than about 100 microns.

In an embodiment of the fifteenth aspect, the silver-containing material has a particle shape that is substantially spherical.

In an embodiment of the fifteenth aspect, the insulating layer comprises at least one polymer selected from the group consisting of polyurethane and polyimide.

In an embodiment of the fifteenth aspect, a ratio of a thickness of the conductive layer to a thickness of insulating layer is from about 1:5 to about 1:1.

In an embodiment of the fifteenth aspect, the conductive material is a silver-containing material.

In an embodiment of the fifteenth aspect, the membrane comprises a polymer having a Shore hardness of from about 70 A to about 55 C.

In an embodiment of the fifteenth aspect, the continuous analyte sensor has an ultimate tensile strength of from about 80 kPsi to about 500 kPsi.

In an embodiment of the fifteenth aspect, the continuous analyte sensor has an ultimate tensile strength of from about 150 kPsi to about 280 kPsi.

In an embodiment of the fifteenth aspect, the continuous analyte sensor has a fatigue life of at least 1,000 cycles of flexing of from about 28° to about 110° at a bend radius of about 0.125-inches.

In an embodiment of the fifteenth aspect, the continuous analyte sensor is configured for multi-axis bending.

In an embodiment of the fifteenth aspect, the multi-axis bending is associated with flexing in at least three directions.

In an embodiment of the fifteenth aspect, the elongated conductive body has a diameter of from about 50 microns to about 250 microns.

In an embodiment of the fifteenth aspect, the continuous analyte sensor has a fatigue life of at least 40 cycles of flexing of from about 45° to about −45° at a bend radius of about 0.031-inches.

In an embodiment of the fifteenth aspect, the continuous analyte sensor has a fatigue life of at least 50 cycles of flexing of from about 45° to about −45° at a bend radius of about 0.031-inches.

In an embodiment of the fifteenth aspect, the continuous analyte sensor has a fatigue life of at least 60 cycles of flexing of from about 45° to about −45° at a bend radius of about 0.031-inches.

In an embodiment of the fifteenth aspect, the continuous analyte sensor has a fatigue life of at least 65 cycles of flexing of from about 45° to about −45° at a bend radius of about 0.031-inches.

BRIEF DESCRIPTION OF THE DRAWINGS

FIG. 2A is a perspective-view schematic illustrating an in vivo portion of an analyte sensor, in one embodiment.

FIG. 2B is a perspective-view schematic illustrating an ex vivo portion of the analyte sensor of FIG. 2A, in one embodiment.

FIG. 3A is a perspective-view schematic illustrating an in vivo portion of an analyte sensor, in another embodiment.

FIG. 3B is a cross-sectional schematic illustrating an in vivo portion of an analyte sensor, in another embodiment.

FIG. 4A is a perspective-view schematic illustrating an in vivo portion of an analyte sensor, in one embodiment.

FIG. 4B is a perspective-view schematic illustrating an in vivo portion of an analyte sensor, in another embodiment.

FIG. 4C is a perspective-view schematic illustrating an in vivo portion of an analyte sensor, in another embodiment.

FIG. 5A is a perspective-view schematic illustrating an in vivo portion of a multi-electrode analyte sensor, in one embodiment.

FIG. 5B is a perspective-view schematic illustrating an in vivo portion of a multi-electrode analyte sensor, in another embodiment.

FIG. 5C is a perspective-view schematic illustrating an in vivo portion of a multi-electrode analyte sensor, in another embodiment.

FIG. 5D is a perspective-view schematic illustrating an in vivo portion of a multi-electrode analyte sensor, in another embodiment.

FIG. 9B is a close perspective schematic of the distal portion of the sensor embodiment illustrated in FIG. 9A.

FIG. 9C is a front view of the sensor embodiment illustrated in FIGS. 9A and 9B.

FIG. 10A is a perspective-view schematic illustrating an in vivo portion of a multi-electrode analyte sensor, in another embodiment.

FIG. 15 is a table summarizing the results of the performance of test sensors with conventional sensors, with respect to fatigue life.

Figure 1A:
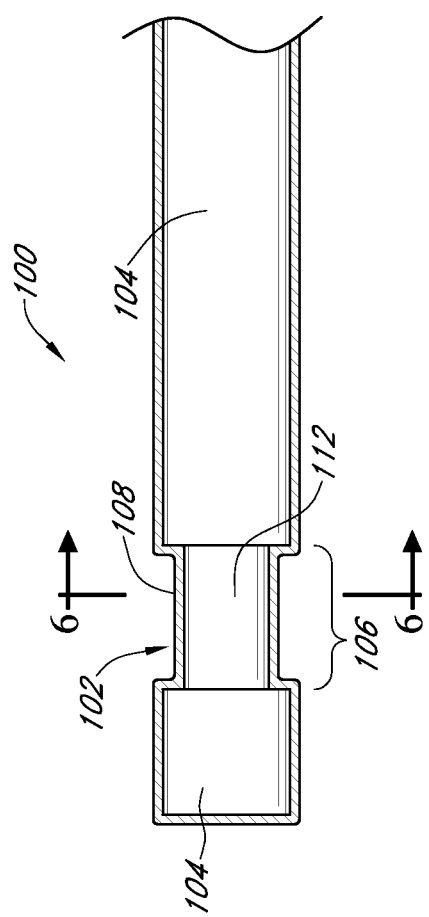
FIG. 1A is a side-view schematic illustrating an in vivo portion of an analyte sensor, in one embodiment.

It should be understood that the figures shown herein are not necessarily drawn to scale.

DETAILED DESCRIPTION OF THE PREFERRED EMBODIMENT

The following description and examples illustrate some exemplary embodiments of the disclosed invention in detail. Those of skill in the art will recognize that there are numerous variations and modifications of this invention that are encompassed by its scope. Accordingly, the description of a certain exemplary embodiment should not be deemed to limit the scope of the embodiments described herein.

In order to facilitate an understanding of the embodiments described herein, a number of terms are defined below.

The term "analyte," as used herein, is a broad term, and is to be given its ordinary and customary meaning to a person of ordinary skill in the art (and is not to be limited to a special or customized meaning), and refers without limitation to a substance or chemical constituent in a biological sample (e.g., body fluids, including, blood, serum, plasma, interstitial fluid, cerebral spinal fluid, lymph fluid, ocular fluid, saliva, oral fluid, urine, excretions, or exudates. Analytes can include naturally occurring substances (e.g., various minerals), artificial substances, metabolites, and/or reaction products. In some embodiments, the analyte for measurement by the sensing regions, devices, and methods is glucose, calcium, sodium, magnesium, potassium, phosphorus, $CO_2$, chloride, blood urea nitrogen, creatinine, pH, a metabolic marker, oxygen, albumin, total protein, alkaline phosphatase, alanine amino transferase, aspartate amino transferase, alanine transaminase, bilirubin, gamma-glutamyl transpeptidase, and hematocrit. However, other analytes are contemplated as well, including but not limited to acetaminophen, dopamine, ephedrine, terbutaline, ascorbate, uric acid, oxygen, d-amino acid oxidase, plasma amine oxidase, Xanthine oxidase, NADPH oxidase, alcohol oxidase, alcohol dehydrogenase, Pyruvate dehydrogenase, diols, Ros, NO, bilirubin, cholesterol, triglycerides, gentisic acid, ibuprophen, L-Dopa, Methyl Dopa, salicylates, tetracycline, tolazamide, tolbutamide, acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotimidase; biopterin; c-reactive protein; carnitine; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, glucose-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; glucose-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lactate dehydrogenase; lead; lipoproteins ((a), B/A-1, β); lysozyme; mefloquine; netilmicin; phenobarbitone; phenyloin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, antinuclear antibody, anti-zeta antibody, arbovirus, Aujeszky's disease virus, dengue virus, *Dracunculus medinensis*, *Echinococcus granulosus*, *Entamoeba histolytica*, enterovirus, *Giardia duodenalisa*, *Helicobacter pylori*, hepatitis B virus, herpes virus, HIV-1, IgE (atopic disease), influenza virus, *Leishmania donovani*, *leptospira*, measles/mumps/rubella, *Mycobacterium leprae*, *Mycoplasma pneumoniae*, Myoglobin, *Onchocerca volvulus*, parainfluenza virus, *Plasmodium falciparum*, poliovirus, *Pseudomonas aeruginosa*, respiratory syncytial virus, *rickettsia* (scrub typhus), *Schistosoma mansoni*, *Toxoplasma gondii*, *Trepenoma pallidium*, *Trypanosoma cruzi/rangeli*, vesicular stomatis virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids can also constitute analytes in certain embodiments. The analyte can be naturally present in the biological fluid, for example, a metabolic product, a hormone, an antigen, an antibody, and the like. Alternatively, the analyte can be introduced into the body, for example, a contrast agent for imaging, a radioisotope, a chemical agent, a fluorocarbon-based synthetic blood, or a drug or pharmaceutical composition, including but not limited to insulin; ethanol; *cannabis* (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbituates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3 MT), 3,4-dihydroxyphenylacetic acid (DOPAC), homovanillic acid (HVA), 5-hydroxytryptamine (5HT), histamine, Advanced Glycation End Products (AGEs) and 5-hydroxyindoleacetic acid (FHIAA).

The term "sample," as used herein, is a broad term, and is to be given its ordinary and customary meaning to a person of ordinary skill in the art (and it is not to be limited to a special or customized meaning), and refers without limitation to a sample of a host body, for example, body fluids, including, blood, serum, plasma, interstitial fluid, cerebral spinal fluid, lymph fluid, ocular fluid, saliva, oral fluid, urine, excretions, or exudates.

The term "calibration," as used herein, is a broad term, and is to be given its ordinary and customary meaning to a person of ordinary skill in the art (and is not to be limited to a special or customized meaning), and refers without limitation to the relationship and/or process of determining the relationship between the sensor data and the corresponding reference data. In some embodiments, namely, in continuous analyte sensors, calibration can be updated or recalibrated over time if changes in the relationship between the sensor data and reference data occur, for example, due to changes in sensitivity, baseline, transport, metabolism, and the like.

The terms "continuous" and "continuously," as used herein in reference to analyte sensing, are broad terms, and are to be given their ordinary and customary meaning to a person of ordinary skill in the art (and is not to be limited to a special or customized meaning), and refer without limitation to the continuous, continual, or intermittent (e.g., regular) monitoring of analyte concentration, such as, for example, performing a measurement about every 1 to 10 minutes. It should be understood that continuous analyte sensors generally continually measure the analyte concentration without required user initiation and/or interaction for each measurement, such as described with reference to continuous glucose sensors in U.S. Pat. No. 6,001,067, for example. These terms include situations wherein data gaps can exist (e.g., when a continuous glucose sensor is temporarily not providing data).

The term "count," as used herein, is a broad term, and is to be given its ordinary and customary meaning to a person of ordinary skill in the art (and is not to be limited to a special or customized meaning), and refers without limitation to a unit of measurement of a digital signal. For example, a raw data stream or raw data signal measured in counts is directly related to a voltage (for example, converted by an A/D converter), which is directly related to current from the working electrode. In some embodiments, the terms can refer to data that has been integrated or averaged over a time period (e.g., 5 minutes).

The term "crosslink," as used herein, is a broad term, and is to be given its ordinary and customary meaning to a person of ordinary skill in the art (and is not to be limited to a special or customized meaning), and refers without limitation to the formation of bonds (e.g., covalent bonds, ionic bonds, hydrogen bonds, etc.) that link one polymer (or oligomer) chain to another, or to a process that increases the cohesiveness of one polymer (or oligomer) chain to another. Crosslinks can be formed, e.g., through various reactions or processes, e.g., chemical processes initiated by heat, pressure, catalysts, radiation, and the like.

The term "distal to," as used herein, is a broad term, and is to be given its ordinary and customary meaning to a person of ordinary skill in the art (and is not to be limited to a special or customized meaning), and refers without limitation to the spatial relationship between various elements in comparison to a particular point of reference. In general, the term indicates an element is located relatively far from the reference point than another element.

The term "proximal to," as used herein, is a broad term, and is to be given its ordinary and customary meaning to a person of ordinary skill in the art (and is not to be limited to a special or customized meaning), and refers without limitation to the spatial relationship between various elements in comparison to a particular point of reference. In general, the term indicates an element is located relatively near to the reference point than another element.

The terms "electrochemically reactive surface" and "electroactive surface," as used herein, are broad terms, and are to be given their ordinary and customary meaning to a person of ordinary skill in the art (and are not to be limited to a special or customized meaning), and refer without limitation to a surface where an electrochemical reaction takes place. As a non-limiting example, in an electrochemical glucose sensor, a working electrode measures hydrogen peroxide, $H_2O_2$, at its electroactive surface. The hydrogen peroxide is produced by the enzyme-catalyzed reaction of the analyte detected, which reacts with the electroactive surface to create a detectable electric current. For example, glucose can be detected utilizing glucose oxidase (GOX), which produces hydrogen peroxide as a byproduct. Hydrogen peroxide reacts with the surface of the working electrode (e.g., the electroactive surface), producing two protons ($2H^+$), two electrons ($2e^-$) and one molecule of oxygen ($O_2$), which produces the electronic current being detected.

The terms "electrical connection" and "electrical contact," as used herein, are broad terms, and are to be given their ordinary and customary meaning to a person of ordinary skill in the art (and are not to be limited to a special or customized meaning), and refer without limitation to any connection between two electrical conductors known to those in the art. In one embodiment, electrodes are in electrical connection with (e.g., electrically connected to) the electronic circuitry of a device. In another embodiment, two materials, such as but not limited to two metals, can be in electrical contact with each other, such that an electrical current can pass from one of the two materials to the other material.

The terms "electronics," "sensor electronics," and "system electronics," as used herein, are broad terms, and are to be given their ordinary and customary meaning to a person of ordinary skill in the art (and are not to be limited to a special or customized meaning), and refer without limitation to electronics operatively coupled to the sensor and configured to measure, process, receive, and/or transmit data associated with a sensor, and/or electronics configured to communicate with a flow control device and to control and/or monitor fluid metering by a flow control device.

The term "elongated conductive body," as used herein, is a broad term, and is to be given its ordinary and customary meaning to a person of ordinary skill in the art (and is not to be limited to a special or customized meaning), and refers without limitation to an elongated body formed at least in part of a conductive material and includes any number of coatings that may be formed thereon. By way of example, an "elongated conductive body" may mean a bare elongated conductive core (e.g., a metal wire) or an elongated conductive core coated with one, two, three, four, five, or more layers of material, each of which may or may not be conductive.

The term "host," as used herein, is a broad term, and is to be given its ordinary and customary meaning to a person of ordinary skill in the art (and is not to be limited to a special or customized meaning), and refers without limitation to plants or animals, for example humans.

The term "ex vivo portion," as used herein, is a broad term, and is to be given its ordinary and customary meaning to a person of ordinary skill in the art (and is not to be limited to a special or customized meaning), and refers without limitation to a portion of a device (for example, a sensor) adapted to remain and/or exist outside of a living body of a host.

The term "in vivo portion," as used herein, is a broad term, and is to be given its ordinary and customary meaning to a person of ordinary skill in the art (and is not to be limited to a special or customized meaning), and refers without limitation to a portion of a device (for example, a sensor) adapted for insertion into and/or existence within a living body of a host.

The term "multi-axis bending," as used herein, is a broad term, and is to be given its ordinary and customary meaning to a person of ordinary skill in the art (and is not to be limited to a special or customized meaning), and refers without limitation to a preference for bending in more than one plane or about more than one axis.

The terms "operatively connected," "operatively linked," "operably connected," and "operably linked" as used herein, are broad terms, and are to be given their ordinary and customary meaning to a person of ordinary skill in the art (and are not to be limited to a special or customized meaning), and refer without limitation to one or more components linked to one or more other components. The terms can refer to a mechanical connection, an electrical connection, or any connection that allows transmission of signals between the components. For example, one or more electrodes can be used to detect the amount of analyte in a sample and to convert that information into a signal; the signal can then be transmitted to a circuit. In such an example, the electrode is "operably linked" to the electronic circuitry. The terms include wired and wireless connections.

The term "potentiostat," as used herein, is a broad term, and is to be given its ordinary and customary meaning to a person of ordinary skill in the art (and is not to be limited to a special or customized meaning), and refers without limitation to an electronic instrument that controls the electrical potential between the working and reference electrodes at one or more preset values.

The term "processor module," as used herein, is a broad term, and is to be given its ordinary and customary meaning to a person of ordinary skill in the art (and are not to be limited to a special or customized meaning), and refers without limitation to a computer system, state machine, processor, components thereof, and the like designed to perform arithmetic or logic operations using logic circuitry that responds to and processes the basic instructions that drive a computer.

The terms "raw data," "raw data stream," "raw data signal," "data signal," and "data stream," as used herein, are broad terms, and are to be given their ordinary and customary meaning to a person of ordinary skill in the art (and are not to be limited to a special or customized meaning), and refer without limitation to an analog or digital signal from the analyte sensor directly related to the measured analyte. For example, the raw data stream is digital data in "counts" converted by an A/D converter from an analog signal (for example, voltage or amps) representative of an analyte concentration. The terms can include a plurality of time spaced data points from a substantially continuous analyte sensor, each of which comprises individual measurements taken at time intervals ranging from fractions of a second up to, for example, 1, 2, or 5 minutes or longer. In some embodiments, the terms can refer to data that has been integrated or averaged over a time period (e.g., 5 minutes).

The terms "sensor" and "sensor system," as used herein, are broad terms, and are to be given their ordinary and customary meaning to a person of ordinary skill in the art (and are not to be limited to a special or customized meaning), and refer without limitation to a device, component, or region of a device by which an analyte can be quantified.

The term "sensor session," as used herein, is a broad term and is to be given its ordinary and customary meaning to a person of ordinary skill in the art (and is not to be limited to a special or customized meaning), and refers without limitation to a period of time a sensor is in use, such as but not limited to a period of time starting at the time the sensor is implanted (e.g., by the host) to removal of the sensor (e.g., removal of the sensor from the host's body and/or removal of (e.g., disconnection from) system electronics).

The terms "membrane system" and "membrane," as used herein, are broad terms, and are to be given their ordinary and customary meaning to a person of ordinary skill in the art (and are not to be limited to a special or customized meaning), and refer without limitation to a permeable or semi-permeable membrane that can comprise one or more layers and constructed of materials, which are permeable to oxygen and may or may not be permeable to an analyte of interest. In one example, the membrane system comprises an immobilized glucose oxidase enzyme, which enables an electrochemical reaction to occur to measure a concentration of glucose.

The terms "substantial" and "substantially," as used herein, are broad terms, and are to be given their ordinary and customary meaning to a person of ordinary skill in the art (and are not to be limited to a special or customized meaning), and refer without limitation to a sufficient amount that provides a desired function.

The development of reliable, user-friendly in vivo analyte sensors has been presented with several technical challenges relating to mechanical properties of the in vivo portion of the sensor. Sensors designed with an in vivo portion that has weak strength are more prone to the risk of breakage. Sensors designed with an in vivo portion that has great strength are often hard, and thus uncomfortable to the patient wearing the sensor. What has been desired is a sensor design that has the mechanical properties (e.g., a certain flexibility/stiffness as measured by Young' modulus and a certain high yield strength that reduces the risk of breakage of a bending sensor) that both lend comfort to the user and mechanical properties (e.g., fatigue life, strength) that provide durability and robustness to the sensor, thereby minimizing the risk of breakage. Described herein are sensor embodiments that overcome these technical obstacles and possesses both the mechanical properties that allow for comfort to the user and that minimizes the risk of breakage. For example, in one embodiment, the sensor comprises an elongated conductive body that has a Young's modulus of from about 160 GPa to about 220 GPa and a yield strength of at least 60 kPsi.

In some embodiments, the sensor is configured and arranged to monitor a single analyte. However, in other embodiments, the sensor is configured and arranged to monitor a plurality of analytes, such as 2, 3, 4, 5, 6, 7, 8, 9, 10, 11, 12, or more different analytes. In yet another embodiment, the sensor is configured to monitor at least one analyte substantially continuously and to monitor at least one analyte intermittently. The analyte that is substantially, continuously monitored and the analyte that is intermittently monitored can be the same analyte or a different one.

In some embodiments, the sensor is configured and arranged for implantation in a host and for generating in vivo a signal associated with an analyte in a sample of the host during a sensor session. In some embodiments, the time length of the sensor session is from about less than 10 minutes, 10 minutes, 20 minutes, 30 minutes, 40 minutes, or 50 minutes to about 1 hour, 2 hours, 3 hours, 4 hours, 5 hours or longer. In some embodiments, the time length of the sensor session is from about 1 hour, 2 hours, 3 hours, 4 hours, 5 hours, 6 hours, 7 hours, 8 hours, 9 hours, or 10 hours to about 11 hours, 12 hours, 13 hours, 14 hours, 15 hours, 16 hours, 17 hours, 18 hours, 19 hours, 20 hours, 21 hours, 22 hours, 23 hours, 24 hours or longer. In some embodiments, the time length of the sensor session is from about less than 0.25 days, 0.25 days, 0.5 days, 0.75 days, or 1 day to about 2 days, 3 days, 4 days, 5 days, 6 days, 7 days, 8 days, 9 days, 10 days or longer.

The analyte sensor can be configured for any type of implantation, such as transcutaneous implantation, subcutaneous implantation, or implantation into the host's circulatory system (e.g., into a vessel, such as a vein or artery). In addition, the sensor may be configured to be wholly implantable or extracorporeally implantable (e.g., into an extracorporeal blood circulatory device, such as a heart-bypass machine or a blood dialysis machine). U.S. Patent Application Publication No. US-2006-0020187-A1 describes an exemplary continuous analyte sensor that can be used for transcutaneous implantation by insertion into the abdominal tissue of a host. U.S. Patent Application Publication No. US-2008-0119703-A1 describes an exemplary embodiment of a continuous analyte sensor that can be used for insertion into a host's vein (e.g., via a catheter). In some embodiments, the sensor is configured and arranged for in vitro use.

By way of example and not of limitation, a wide variety of suitable detection methods including, but not limited to, enzymatic, chemical, physical, electrochemical, immunochemical, optical, radiometric, calorimetric, protein binding, and microscale methods of detection, can be employed in certain embodiments, although any other techniques can also be used. Additional description of analyte sensor configurations and detection methods that can be used can be found in U.S. Patent Application Publication No. US-2007-0213611-A1, U.S. Patent Application Publication No. US-2007-0027385-A1, U.S. Patent Application Publication No. US-2005-0143635-A1, U.S. Patent Application Publication No. US-2007-0020641-A1, U.S. Patent Application Publication No. US-2007-002064-A11, U.S. Patent Application Publication No. US-2005-0196820-A1, U.S. Pat. No. 5,517,313, U.S. Pat. No. 5,512,246, U.S. Pat. No. 6,400,974, U.S. Pat. No. 6,711,423, U.S. Pat. No. 7,308,292, U.S. Pat. No. 7,303,875, U.S. Pat. No. 7,289,836, U.S. Pat. No. 7,289,204, U.S. Pat. No. 5,156,972, U.S. Pat. No. 6,528,318, U.S. Pat. No. 5,738,992, U.S. Pat. No. 5,631,170, U.S. Pat. No. 5,114,859, U.S. Pat. No. 7,273,633, U.S. Pat. No. 7,247,443, U.S. Pat. No. 6,007,775, U.S. Pat. No. 7,074,610, U.S. Pat. No. 6,846,654, U.S. Pat. No. 7,288,368, U.S. Pat. No. 7,291,496, U.S. Pat. No. 5,466,348, U.S. Pat. No. 7,062,385, U.S. Pat. No. 7,244,582, U.S. Pat. No. 7,211,439, U.S. Pat. No. 7,214,190, U.S. Pat. No. 7,171,312, U.S. Pat. No. 7,135,342, U.S. Pat. No. 7,041,209, U.S. Pat. No. 7,061,593, U.S. Pat. No. 6,854,317, U.S. Pat. No. 7,315,752, and U.S. Pat. No. 7,312,040.

Although certain sensor configurations and methods of manufacture are described herein, it should be understood that any of a variety of known sensor configurations can be employed with the analyte sensor systems and methods of manufacture described herein, such as those described in U.S. Pat. No. 5,711,861 to Ward et al., U.S. Pat. No. 6,642,015 to Vachon et al., U.S. Pat. No. 6,654,625 to Say et al., U.S. Pat. No. 6,565,509 to Say et al., U.S. Pat. No. 6,514,718 to Heller, U.S. Pat. No. 6,465,066 to Essenpreis et al., U.S. Pat. No. 6,214,185 to Offenbacher et al., U.S. Pat. No. 5,310,469 to Cunningham et al., and U.S. Pat. No. 5,683,562 to Shaffer et al., U.S. Pat. No. 6,579,690 to Bonnecaze et al., U.S. Pat. No. 6,484,046 to Say et al., U.S. Pat. No. 6,103,033 to Say et al., U.S. Pat. No. 6,512,939 to Colvin et al., U.S. Pat. No. 6,424,847 to Mastrototaro et al., U.S. Pat. No. 6,424,847 to Mastrototaro et al., for example. The sensors described in the above-identified patents documents are not inclusive of all applicable analyte sensors. It should be understood that the disclosed embodiments are applicable to a variety of analyte sensor configurations. It is noted that much of the description of the embodiments, for example the membrane system described below, can be implemented not only with in vivo sensors, but also with in vitro sensors, such as blood glucose meters (SMBG).

The sensors of certain embodiments are configured and arranged for implantation into body structures. In use, the in vivo portion of the sensor can be bent about one or more axes. This bending can occur intermittently, which can be frequently or infrequently, depending upon factors such as the nature of the implantation site (e.g., the type(s) of surrounding tissue, the thicknesses of the tissue, etc.), the type or amount of host activity, and/or the sensor's configuration.

In one embodiment, the sensor is configured and arranged for transcutaneous implantation. One exemplary transcutaneous implantation site is the abdomen, which includes an abdominal wall with a plurality of layers (e.g., skin, fascia, fat, muscles) that can move and/or slide transversely with respect of one another (e.g., in response to movement by the host). The fascia can sometimes slide, stretch or move small distances across underlying fat or muscle tissue.

In some embodiments, when a sensor is transcutaneously implanted, the in vivo portion passes through the skin and into an underlying tissue layer. Depending upon the nature of the implantation site, the sensor may pass through two or more tissue layers. Consequently, voluntary or involuntary movements by the host can move the tissue layers, which in turn can apply force to the implanted sensor. Similarly, when the sensor is implanted into the host's circulatory system, such as into a vein or artery, and the host moves his arm, wrist and/or hand, forces may be applied to the implanted sensor.

When certain forces (e.g., forces that cause the sensor to bend in a non-preferred bending axis) are applied to a conventional sensor, they can cause damage to the sensor and/or the tissue surrounding the sensor. In contrast, the sensors of some of the embodiments are configured and arranged to bend and/or flex in response to forces applied thereto by surrounding tissue and/or body movements. While not wishing to be bound by theory, it is believed that the capability of some sensor embodiments to bend or flex, in response to application of forces by the surrounding tissue, reduces the risk of host tissue damage and sensor damage, while still maintaining sensor accuracy.

In certain embodiments, the sensor is configured and arranged for a unique combination of strength and flexibility that enables the sensor to be implanted for at least one, two, three or more days and to measure at least one analyte after implantation, while withstanding intermittent and/or repeated bending and/or flexing about multiple axes, such that the sensors. In some embodiments, the sensor is configured and arranged to bend and/or flex at one, two, three or more points along its length (e.g., along a length corresponding to the in vivo portion implanted into the host). Additionally or alternatively, the sensor may be capable of bending about a plurality of axes (e.g., multi-axis bending) and/or within a plurality of planes. As is described in greater detail elsewhere herein, components of the sensor may be treated, formed and/or combined in a way to achieve the requisite combination of strength or flexibility that enables certain sensor embodiments to provide substantially accurate continuous analyte data, while withstanding a harsh implantation environment for at least 1, 2, 3 or more days while, at the same time.

Figure 1C:
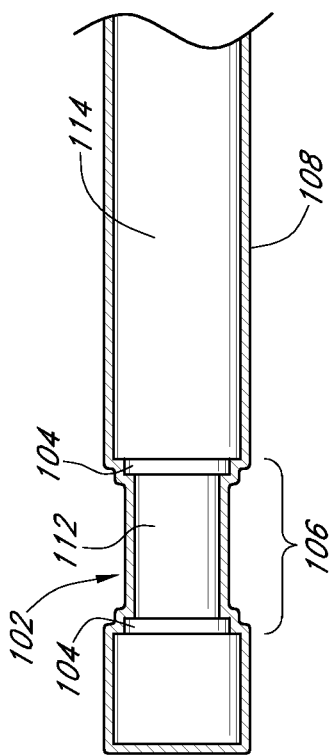
FIG. 1C is a side-view schematic illustrating an in vivo portion of an analyte sensor, in another embodiment.
Figure 1B:
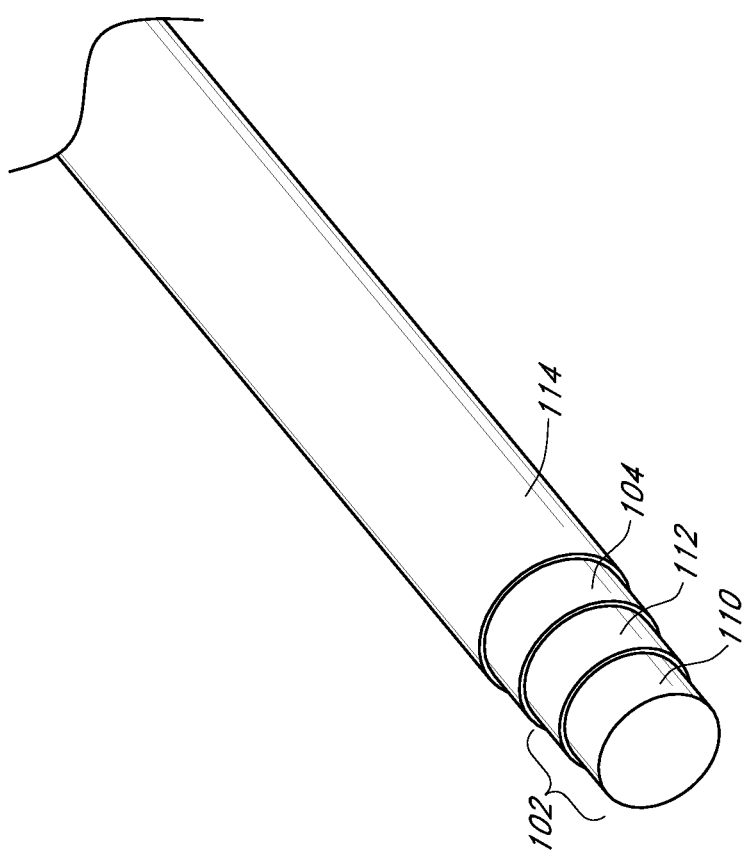
FIG. 1B is a perspective-view schematic illustrating an in vivo portion of an analyte sensor, in one embodiment.

FIGS. 1A through 1C illustrate one aspect (e.g., the in vivo portion) of a continuous analyte sensor 100, which includes an elongated conductive body 102. The elongated conductive body 102 includes a core 110 (see FIG. 1B) and a first layer 112 at least partially surrounding the core. The first layer includes a working electrode (e.g., located in window 106) and a membrane 108 located over the working electrode configured and arranged for multi-axis bending. In some embodiments, the core and first layer can be of a single material (e.g., platinum). In some embodiments, the elongated conductive body is a composite of at least two materials, such as a composite of two conductive materials, or a composite of at least one conductive material and at least one non-conductive material. In some embodiments, the elongated conductive body comprises a plurality of layers. In certain embodiments, there are at least two concentric (e.g., annular) layers, such as a core formed of a first material and a first layer formed of a second material. However, additional layers can be included in some embodiments. In some embodiments, the layers are coaxial.

The elongated conductive body may be long and thin, yet flexible and strong. For example, in some embodiments, the smallest dimension of the elongated conductive body is less than about 0.1 inches, 0.075 inches, 0.05 inches, 0.025 inches, 0.01 inches, 0.004 inches, or 0.002 inches. While the elongated conductive body is illustrated in FIGS. 1A through 1C as having a circular cross-section, in other embodiments the cross-section of the elongated conductive body can be ovoid, rectangular, triangular, polyhedral, star-shaped, C-shaped, T-shaped, X-shaped, Y-Shaped, irregular, or the like. In one embodiment, a conductive wire electrode is employed as a core. To such a clad electrode, two additional conducting layers may be added (e.g., with intervening insulating layers provided for electrical isolation). The conductive layers can be comprised of any suitable material. In certain embodiments, it can be desirable to employ a conductive layer comprising conductive particles (i.e., particles of a conductive material) in a polymer or other binder.

In certain embodiments, the materials used to form the elongated conductive body (e.g., stainless steel, titanium, tantalum, platinum, platinum-iridium, iridium, certain polymers, and/or the like) can be strong and hard, and therefore are resistant to breakage. For example, in some embodiments, the ultimate tensile strength of the elongated conductive body is from about 80 kPsi to about 500 kPsi. In another example, in some embodiments, the Young's modulus of the elongated conductive body is from about 160 GPa to about 220 GPa. In still another example, in some embodiments, the yield strength of the elongated conductive body is from about 60 kPsi to about 2200 MPa. Ultimate tensile strength, Young's modulus, and yield strength are discussed in greater detail elsewhere herein. In some embodiments, the sensor's small diameter provides (e.g., imparts, enables) flexibility to these materials, and therefore to the sensor as a whole. Thus, the sensor can withstand repeated forces applied to it by surrounding tissue. One measurement of the sensor's ability to withstand the implantation environment is fatigue life, which is described in greater detail in the section entitled "Multi-Axis Bending." In some embodiments, the fatigue life of the sensor is at least 1,000 cycles of flexing of from about 28° to about 110° at a bend radius of about 0.125-inches.

In addition to providing structural support, resiliency and flexibility, in some embodiments, the core 110 (or a component thereof) provides electrical conduction for an electrical signal from the working electrode to sensor electronics (not shown), which are described elsewhere herein. In some embodiments, the core 110 comprises a conductive material, such as stainless steel, titanium, tantalum, a conductive polymer, and/or the like. However, in other embodiments, the core is formed from a non-conductive material, such as a non-conductive polymer. In yet other embodiments, the core comprises a plurality of layers of materials. For example, in one embodiment the core includes an inner core and an outer core. In a further embodiment, the inner core is formed of a first conductive material and the outer core is formed of a second conductive material. For example, in some embodiments, the first conductive material is stainless steel, titanium, tantalum, a conductive polymer, an alloy, and/or the like, and the second conductive material is conductive material selected to provide electrical conduction between the core and the first layer, and/or to attach the first layer to the core (e.g., if the first layer is formed of a material that does not attach well to the core material). In another embodiment, the core is formed of a non-conductive material (e.g., a non-conductive metal and/or a non-conductive polymer) and the first layer is a conductive material, such as stainless steel, titanium, tantalum, a conductive polymer, and/or the like. The core and the first layer can be of a single (or same) material, e.g., platinum. One skilled in the art appreciates that additional configurations are possible.

Referring again to FIGS. 1A-1C, in some embodiments, the first layer 112 is formed of a conductive material. The working electrode is an exposed portion of the surface of the first layer. Accordingly, the first layer is formed of a material configured to provide a suitable electroactive surface for the working electrode, a material such as but not limited to platinum, platinum-iridium, gold, palladium, iridium, graphite, carbon, a conductive polymer, an alloy and/or the like.

As shown in FIG. 1B-1C, a second layer 104 surrounds a least a portion of the first layer 112, thereby defining the boundaries of the working electrode. In some embodiments, the second layer 104 serves as an insulator and is formed of an insulating material, such as polyimide, polyurethane, parylene, or any other known insulating materials. For example, in one embodiment the second layer is disposed on the first layer and configured such that the working electrode is exposed via window 106. In another embodiment, an elongated conductive body, including the core, the first layer and the second layer, is provided, and the working electrode is exposed (i.e., formed) by removing a portion of the second layer, thereby forming the window 106 through which the electroactive surface of the working electrode (e.g., the exposed surface of the first layer) is exposed. In some embodiments, the working electrode is exposed by (e.g., window 106 is formed by) removing a portion of the second and (optionally) third layers. Removal of coating materials from one or more layers of elongated conductive body (e.g., to expose the electroactive surface of the working electrode) can be performed by hand, excimer lasing, chemical etching, laser ablation, grit-blasting, or the like.

In some embodiments, the sensor further comprises a third layer 114 comprising a conductive material. In further embodiments, the third layer may comprise a reference electrode, which may be formed of a silver-containing material that is applied onto the second layer (e.g., an insulator). The silver-containing material may include any of a variety of materials and be in various forms, such as, Ag/AgCl-polymer pastes, paints, polymer-based conducting mixture, and/or inks that are commercially available, for example. The third layer can be processed using a pasting/dipping/coating step, for example, using a die-metered dip coating process. In one exemplary embodiment, an Ag/AgCl polymer paste is applied to an elongated body by dip-coating the body (e.g., using a meniscus coating technique) and then drawing the body through a die to meter the coating to a precise thickness. In some embodiments, multiple coating steps are used to build up the coating to a predetermined thickness. Such a drawing method can be utilized for forming one or more of the electrodes in the device depicted in FIG. 1B.

In some embodiments, the silver grain in the Ag/AgCl solution or paste can have an average particle size associated with a maximum particle dimension that is less than about 100 microns, or less than about 50 microns, or less than about 30 microns, or less than about 20 microns, or less than about 10 microns, or less than about 5 microns. The silver chloride grain in the Ag/AgCl solution or paste can have an average particle size associated with a maximum particle dimension that is less than about 100 microns, or less than about 80 microns, or less than about 60 microns, or less than about 50 microns, or less than about 20 microns, or less than about 10 microns. The silver grain and the silver chloride grain may be incorporated at a ratio of the silver chloride grain:silver grain of from about 0.01:1 to 2:1 by weight, or from about 0.1:1 to 1:1. The silver grains and the silver chloride grains are then mixed with a carrier (e.g., a polyurethane) to form a solution or paste. In certain embodiments, the Ag/AgCl component form from about 10% to about 65% by weight of the total Ag/AgCl solution or paste, or from about 20% to about 50%, or from about 23% to about 37%. In some embodiments, the Ag/AgCl solution or paste has a viscosity (under ambient conditions) that is from about 1 to about 500 centipoise, or from about 10 to about 300 centipoise, of from about 50 to about 150 centipoise.

In some embodiments, Ag/AgCl particles are mixed into a polymer, such as polyurethane, polyimide, or the like, to form the silver-containing material for the reference electrode. In some embodiments, the third layer is cured, for example, by using an oven or other curing process. In some embodiments, a covering of fluid-permeable polymer with conductive particles (e.g., carbon particles) therein is applied over the reference electrode and/or third layer. A layer of insulating material is located over a portion of the silver-containing material, in some embodiments.

In some embodiments, the elongated conductive body further comprises one or more intermediate layers located between the core and the first layer. For example, in some embodiments, the intermediate layer is an insulator, a conductor, a polymer, and/or an adhesive.

It is contemplated that the ratio between the thickness of the Ag/AgCl layer and the thickness of an insulator (e.g., polyurethane or polyimide) layer can be controlled, so as to allow for a certain error margin (e.g., an error margin associated with the etching process) that would not result in a defective sensor (e.g., due to a defect resulting from an etching process that cuts into a depth more than intended, thereby unintentionally exposing an electroactive surface). This ratio may be different depending on the type of etching process used, whether it is laser ablation, grit blasting, chemical etching, or some other etching method. In one embodiment in which laser ablation is performed to remove a Ag/AgCl layer and a polyurethane layer, the ratio of the thickness of the Ag/AgCl layer and the thickness of the polyurethane layer can be from about 1:5 to about 1:1, or from about 1:3 to about 1:2.

In certain embodiment, the core comprises a non-conductive polymer and the first layer comprises a conductive material. Such a sensor configuration can sometimes provide reduced material costs, in that it replaces a typically expensive material with an inexpensive material. For example, in some embodiments, the core is formed of a non-conductive polymer, such as, a nylon or polyester filament, string or cord, which can be coated and/or plated with a conductive material, such as platinum, platinum-iridium, gold, palladium, iridium, graphite, carbon, a conductive polymer, and allows or combinations thereof.

Figure 1E:
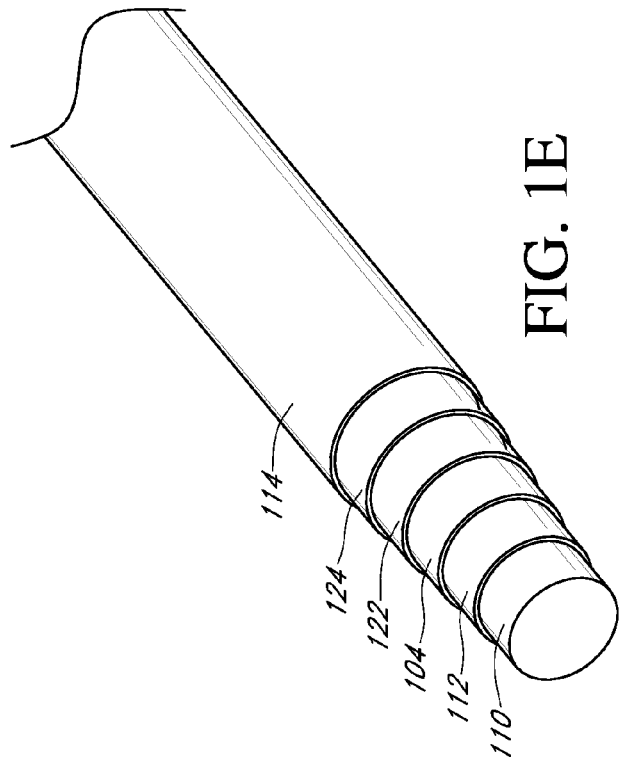
FIG. 1E is a side-view schematic illustrating an in vivo portion of an analyte sensor, in another embodiment.
Figure 1G:
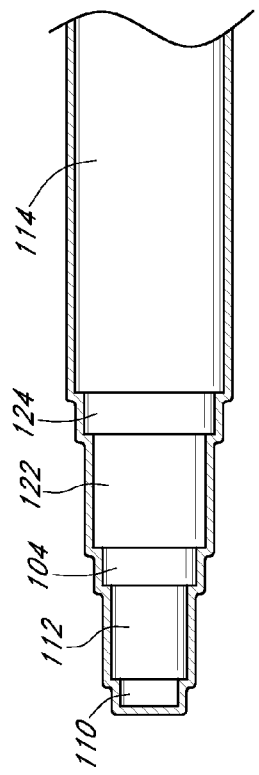
FIG. 1G is a side-view schematic illustrating an in vivo portion of an analyte sensor, in another embodiment.
Figure 1D:
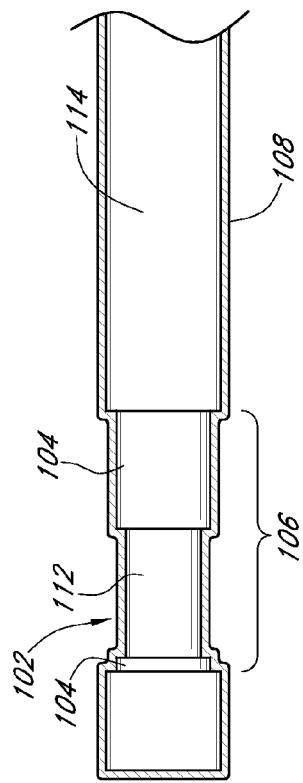
FIG. 1D is a cross-sectional/side-view schematic illustrating an in vivo portion of an analyte sensor, in another embodiment.

As shown in FIGS. 1C and 1D, the sensor also includes a membrane 108 covering at least a portion of the working electrode. Membranes are discussed in detail in the section entitled "Membrane Configurations."

FIGS. 3A and 3B illustrate another aspect of a continuous analyte sensor 100, including an elongated body comprising a conductive core 110 and an insulating layer 104 at least partially surrounding the conductive core, a working electrode body 112 in electrical contact with the conductive core, and a membrane (not shown) covering the working electrode body. The elongated conductive body is configured and arranged for multi-axis bending. In some embodiments, such as the embodiment shown in FIG. 3A, the sensor includes a single insulated conductive core. However, in other embodiments, two, three, or more conductive cores are embedded in a single insulator. For example, FIG. 3B shows an elongated body having three conductive cores embedded in the insulator. The conductive core is formed of a conductive material suitable to electrically connect the working electrode body to sensor electronics (not shown), and to provide flexible support to the sensor. The conductive material can include, but is not limited to, stainless steel, titanium, tantalum, a conductive polymer, an alloy, or the like. In some embodiments, the conductive core comprises an inner core and an outer core. In further embodiments, the inner core comprises a first conductive material, and the outer core comprises a second conductive material. In alternative embodiments, the inner core comprises an insulating material (e.g., non-conductive material) and the outer core comprises a conductive material. For example, a non-conductive polymer, such as nylon filament can be used to form the core, and electrical conduction (e.g., between the working electrode body and sensor electronics) is provided by an outer core formed of a conductive material, such as, for example, stainless steel, titanium, tantalum, a conductive polymer, an alloy or the like.

In some embodiments, the insulating layer 104 can be formed of any of a variety of insulating materials, such as polyurethane, polyimide, for example, as described elsewhere herein. In some embodiments, such as those shown in FIGS. 3A and 3B, a window 106 is formed in the insulator, such as by removal of a portion of the insulator using techniques described elsewhere herein. However, in other embodiments, no window is formed; rather, the working electrode body (as described below) is configured to penetrate through (e.g., by piercing) the insulator and make physical contact (e.g., electrical contact) with the core. In certain embodiments, one or more insulating layers can be formed from heat-shrink material.

As shown in FIGS. 3A and 3B, the sensor includes a working electrode body 112, which is formed of any of a variety of conductive materials, such as, platinum, platinum-iridium, gold, palladium, iridium, graphite, carbon, a conductive polymer, an alloy, and the like, for example. The working electrode body provides the electroactive surface of the working electrode. In some embodiments, the working electrode body includes a structure that can be attached to the elongated body, such as by crimping, clamping, welding, adhesive, and/or the like, such as but not limited to a C-clip, a washer, a foil, and the like. The working electrode body is applied to the conductive core, such that the working electrode body and the conductive core are electrically connected. In some embodiments, at least a portion of the working electrode body penetrates (e.g., pierces, intersects) the insulating layer 104 to physically contact (e.g., touch) the core, such that the working electrode body and the conductive core are electrically connected. In other embodiments, the working electrode body is applied over window 106, such that it makes electrical contact with the conductive core through the window. In some embodiments, one or more conductive materials are applied between the working electrode body and the core to facilitate conductivity therebetween. In some embodiments, an adhesive, such as a conductive adhesive, is applied between the working electrode body and the conductive core, so as to attach the working electrode body to the core. In some embodiments, additional materials, such as but not limited to polytetrafluoroethylene (such as is marketed under the trade name TEFLON®), are used to attach the working electrode body to the conductive core.

In some embodiments, instead of an elongated body having a plurality of conductive cores embedded in an insulator, the sensor includes two or more elongated bodies (e.g., bundled and/or twisted together) with at least one of the elongated bodies having a working electrode body electrically connected thereto. For example, FIG. 4C illustrates an in vivo portion of a sensor including three elongated bodies, wherein each elongated body includes a conductive core at least partially coated in insulator. Two of the elongated bodies are shown to include windows, wherein working electrode bodies can be attached. In an alternative embodiment, windows are not formed, and the working electrode bodies are C-clip structures that are crimped about the elongated bodies, wherein the ends of the C-clips pierce the insulator and make physical (e.g., electrical) contact with the underlying conductive cores. In yet another embodiment, the working electrode body is deposited, printed, and/or plated on the conductive core (e.g., through the window).

In some embodiments, the sensor includes a reference electrode, and optionally an insulator applied to an ex vivo portion of the sensor (e.g., a portion of the reference electrode material exposed to air during implantation), such as described herein.

FIG. 4B illustrates another embodiment of an analyte sensor, including an elongated body comprising an insulator 104, a first conductive core 110A embedded in the insulator and a second conductive core 110B embedded in the insulator. The insulator comprises a first window 106A configured and arranged to expose an electroactive portion of the first conductive core, wherein the insulator also comprises a second window 106B configured and arranged to expose an electroactive portion of the second conductive core. The elongated body is configured and arranged for multi-axis bending. A membrane 108 covers the exposed electroactive portion of the first conductive core. In some embodiments, the sensor has a relatively small diameter, such as described elsewhere herein. For example, in some embodiments, the smallest dimension of the elongated body is less than or equal to about 0.002 inches, 0.004 inches, 0.01 inches, 0.05 inches, 0.075 inches, 0.1 inches, 0.25 inches, 0.5 inches, or 0.75 inches. The elongated body can be formed using a variety of insulators known in the art. In some embodiments, the insulator comprises at least one of polyurethane or polyimide.

In some embodiments, the electroactive portion of the first conductive core is a working electrode. Accordingly, in some embodiments, the first conductive core may be formed of platinum, platinum-iridium, gold, palladium, iridium, graphite, carbon, a conductive polymer, or combinations or alloys thereof. In alternative embodiments, the first conductive core comprises a core and a first layer, wherein an exposed electroactive surface of the first layer provides the working electrode. For example, in some embodiments, the core comprises stainless steel, titanium, tantalum and/or a polymer, and the first layer comprises platinum, platinum-iridium, gold, palladium, iridium, graphite, carbon, a conductive polymer and/or an alloy.

In some embodiments, the second conductive core provides a reference electrode, and thus may be formed of a silver-containing material, such as, a silver wire or a silver-containing polymer, for example. In some embodiments, the silver is chloridized prior to being embedded in the insulator. In other embodiments, the silver is non-chloridized prior to being embedded in the insulator, and is chloridized after the silver is exposed (e.g., via window 106B).

In some embodiments, a third conductive core is embedded in the insulator. For example, in some embodiments, the sensor is a dual-electrode sensor and the third conductive core is configured as a second working electrode. In alternative embodiments, the third conductive core is configured as a counter electrode, in some embodiments. The third conductive core is a wire-shaped structure formed of at least one of platinum, platinum-iridium, gold, palladium, iridium, graphite, carbon, a conductive polymer and an alloy, in some embodiments. Alternatively, the third conductive core can include a core and a first layer, such as described herein. In some further embodiments, the core comprises an inner core and an outer core, such as described herein.

In some further embodiments, the sensor includes two or more additional working electrodes. For example, the sensor can be configured to detect two or more analytes. Alternatively, some of the additional working electrodes can be configured as redundant sensors.

Referring again to FIG. 4B, in one exemplary embodiment, the sensor is a glucose sensor configured and arranged for multi-axis bending, and comprises an elongated body comprising an insulator 104 formed of an insulating material such as a polyurethane or a polyimide. A platinum or a platinum-iridium wire and a silver wire 110B is embedded in the insulator. The electroactive surface (e.g., the working electrode) of the platinum or a platinum-iridium wire is exposed via window 106A. The reference electrode (e.g., of the silver wire) is exposed via window 106B. A membrane 108 covers at least the working electrode. In some embodiments, the membrane may cover a larger portion of the sensor. For example, in FIG. 4B, the membrane covers the illustrated in vivo portion of the sensor.

The sensor can be manufactured using a variety of techniques and methods known in the art. For example, in one embodiment, the elongated body is provided with the insulator 104 and with the first 110A and second 110B conductive cores embedded therein). Portions of the insulator (e.g., windows 106A and 1060B) are then removed to expose the working electrode (e.g., located on the first conductive core, the Pt or Pt/Ir wire) and the reference electrode (e.g., located on the second conductive core, the Ag wire). In some embodiments, the step of removing a portion of the insulator to expose the working electrode and/or the reference electrode comprises ablating (e.g., laser or UV ablation) a portion of the insulator. Alternatively, portions of insulator can be removed manually or using methods known in the art such as grit blasting. If the silver wire is not provided as a chloridized wire, it can be chloridized prior to application of a membrane to the sensor. In some circumstances, the electroactive surfaces are cleaned, using standard methods known in the art, prior to membrane application. The membrane 108 is then applied to at least a portion of the sensor, such as but not limited to the working electrode. For example, at least the portion of the membrane covering the working electrode includes an enzyme (e.g., glucose oxidase) selected to detect the analyte.

In some embodiments, the membrane is formed of a polymer having a Shore hardness of from about 70 A to about 55 D. In some embodiments, one or more of the membrane domains are formed of polymers within this hardness range. However, in some embodiments, only the resistance domain is formed from a polymer having a Shore hardness of from about 70 A to about 55 D. While not wishing to be bound by theory, it is believed that some polymers having a Shore hardness in this range are sufficiently elastic yet resilient to withstand multi-axis bending without substantial disruption of the membrane's function. In some embodiments, the manufactured sensor has a fatigue life of at least about 1,000 cycles of flexing of from about 28° to about 110° at a bend radius of about 0.125 inches. However, the sensors of other embodiments can have longer fatigue lives (e.g., fatigue lives of about at least 10,000, 20,000, 30,000, 40,000 or 50,000 cycles or more of flexing).

Figure 7:
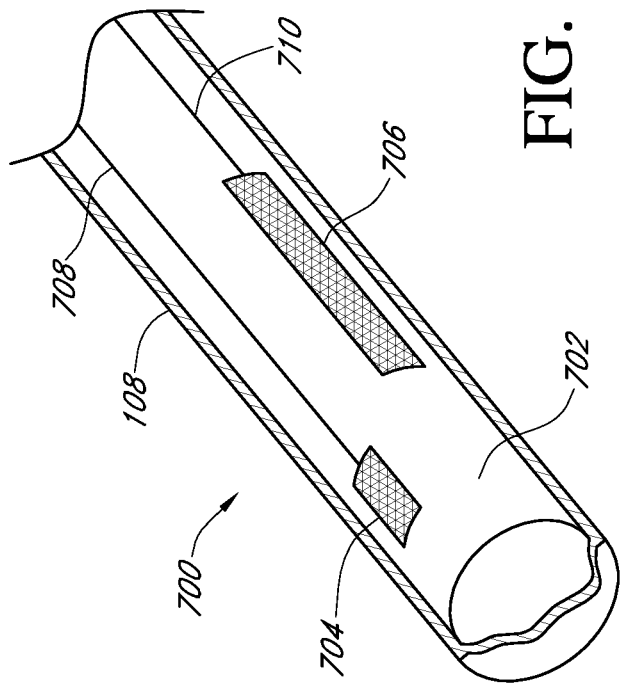
FIG. 7 is a perspective-view schematic illustrating an in vivo portion of an analyte sensor, in another embodiment.

FIG. 7 illustrates yet another continuous analyte sensor of an embodiment. In this particular embodiment, the sensor 700 comprises an elongated body 702 configured and arranged for multi-axis bending. The elongated conductive body 702 comprises a nonconductive material, a working electrode 704 located on the elongated body, a reference electrode 706 located on the elongated body, and a membrane 108 covering the working electrode. Conductive pathways 708 and 710 connect the working electrode and the reference electrode (respectively) to the sensor electronics (not shown). In further embodiments, the sensor is configured and arranged such that the fatigue life of the sensor is at least 1,000 cycles of flexing of from about 28° to about 110° at a bend radius of about 0.125 inches. Some embodiments are configured to provide longer fatigue lives, as described in the section entitled "Multi-Axis Bending."

In some embodiments, the elongated body can be formed out of any nonconductive material that can be formed into a thin, elongated structure. In further embodiments, the nonconductive material is a polymer. The polymer may be a nylon or polyester filament, string or cord, etc. In some embodiments, the elongated body is non-planar, such as described herein, and thus has a non-rectangular cross-section. However, in certain embodiments, the elongated body is planar. In some embodiments, the smallest dimension (e.g., the diameter or width) of the elongated body is less than about 0.004 inches. However, in certain embodiments, relatively larger or smaller sensor diameters are acceptable, such as described elsewhere herein.

The sensor 700 illustrated in FIG. 7 can be manufactured using a variety of techniques known in the art. In one embodiment, a method of making a flexible continuous analyte sensor adapted for in vivo use includes the steps of providing a non-planar elongated body 702 comprising a nonconductive material, applying a working electrode 704, the reference electrode 706 and conductive pathways 708, 710 on the elongated body, and covering (at least) the working electrode with a membrane 108, thereby producing a sensor capable of multi-axis bending. In some embodiments, the working electrode is applied by depositing a conductive material (e.g., at least one of platinum, platinum-iridium, gold, palladium, iridium, graphite, carbon, a conductive polymer and an alloy) on the elongated body. In some embodiments, the conductive material is an ink, paint or paste, and is deposited using thick film and/or thin film deposition techniques known in the art, such as but not limited to screen printing, jet printing, block printing, and the like. However, in some embodiments the working electrode material is plated on the elongated body, using plating techniques known in the art, such as but not limited to electroplating. The reference electrode can be applied by depositing a silver-containing material on the elongated body. Similar to the working electrode, the silver-containing material of the reference electrode can be deposited using thick film and/or thin film deposition techniques, various printing techniques known in the art, and/or plating. The membrane is applied to at least the working electrode using standard techniques. In particular, in some embodiments, the membrane is applied by applying a polymer having a Shore hardness of from about 70 A to about 55 D. As described with reference to FIG. 6, the membrane can include a plurality of layers and/or domains. The outermost domain in certain embodiments is the resistance domain, which is configured to modulate the amount of analyte and/or other substances diffusing into and/or through the membrane. In some embodiments, the step of applying a membrane comprises forming a resistance domain from a polymer having a Shore hardness of from about 70 A to about 55 D. For example, additional membrane domains (e.g., enzyme, interference, electrode domains, etc.) can be formed of other polymers, as is known in the art and described with reference to FIG. 6. While the sensor can be manufactured by hand, in some embodiments, at least one step is semi-automated. In certain embodiments, at least one step is fully-automated. In some circumstances, two or more steps are semi-automated or fully-automated.

Various sensor configurations that can be useful in connection with certain embodiments are described in U.S. Pat. No. 7,529,574. For example, the analyte sensor can have an active sensing region that includes an electrochemically active surface and a membrane system that adheres to or is otherwise situated atop the electrochemically active surface, wherein one or more protruding structures of dielectric material may extend outwardly from the electrochemically active surface (or other surface below the membrane system) and serve as supportive structure(s) to the membrane system. This particular configuration can be desirable when forming the membrane by dip coating a liquid (e.g., a viscous liquid, or curable liquid) onto the electrochemically active surface or other underlying surface of the sensor. The protruding structures are configured in a way such that they can support the liquid before, during, or after the curing process. The protruding structures can be in a form of one or more rings having, e.g., sharp corners or smooth edges, a square or semicircular cross section, or any other desired configuration. For example, the sensor can comprise a platinum wire coated with an insulating material (e.g., a polyimide layer), and a silver wire can be wrapped around a portion of this structure. A retractor (e.g., of stainless steel or other suitable material) can be incorporated into the sensor. Portions of the insulating material can be removed, e.g., by laser ablating, with the remaining insulating material forming the protruding structures (e.g., in the form of protruding rings). Multiple protruding structures can be spaced longitudinally along the surface of the platinum wire. After the laser ablation operation, the platinum wire with protruding structures is dip coated with one or more membrane layers, e.g., one or more layers such as an interference layer, a resistance layer, an enzyme layer, and the like, as discussed elsewhere herein. The protruding structures enable additional coating material to adhere to the wire, e.g., through capillary action, which can be desirable in forming thicker membranes in fewer steps, or by reducing the number of dip coating/curing steps necessary to form a particular thickness of layer.

U.S. Patent Application Publication No. US-2007-0173711-A1 describes thin film fabricating techniques that can be employed in the manufacture of sensors of certain embodiments. In such techniques, a base layer or substrate (conducting or nonconducting) is subjected to one or more deposition steps (e.g., metallization steps to form one or more conductive layers and/or electrode layers, or steps wherein an electrically insulating layer such as a polyurethane or polyimide is applied) to form at least a portion of the sensor. For example, a base layer that is an electrically insulating layer such as a polyimide substrate can be employed (e.g., self-supporting or further supported by another material). The base layer can be a polyimide tape, dispensed from a reel, to facilitate clean, high density mass production, and/or production of sensors on both sides of the tape.

Metallization steps involve application of a conductive layer onto an insulating layer (or other layer). The conductive layer can be provided as a plurality of thin film conductive layers, e.g., a chrome-based layer for chemical adhesion to the base layer, followed by subsequent formation of a thin film gold- or platinum-based layer, or a chrome-based top layers on top of the thin film gold- or platinum-based layer. The conductive layer may also be formed of gold and/or chrome in different ratios and/or other adhesive/conductive layers, such as titanium, platinum, tungsten, or the like. In alternative embodiments, other electrode layer conformations or materials can be used. The conductive layer can be applied using electrode deposition, surface sputtering, or another suitable process step. The electrical circuit of each conductive layer typically comprises one or more conductive paths with regions at a proximal end that form contacts and regions at a distal end that form sensor electrodes. Generally, etching is performed to define the electrical circuit of each layer. Alternatively, "lift off" may be used, in which the photoresist defines a pattern prior to metal sputtering, after which the photoresist is dissolved away (along with the unwanted metal), and the metal pattern is left behind. In further embodiments, photoresisting is performed to protect the metalized pathway and electrode and photoimaging is performed to cure specified areas. For example, the conductive layer is covered with a selected photoresist coating, followed by an etch step resulting in one or more conductive paths. An electrically insulating cover layer (or dielectric layer), such as a polymer coating, is then applied over at least portions of the conductive layer. Suitable polymer coatings for use as the insulating cover layer include, for example, non-toxic biocompatible polymers such as polyimide, biocompatible solder masks, epoxy acrylate copolymers, and the like. Further, these coatings can be photoimageable to facilitate photolithographic formation of apertures through to the conductive layer to expose the electrode. Multiple metallization steps can be employed to fabricate additional electrodes (e.g., sequentially) when intervening insulating layers are employed. For example, the resulting electrodes can be in a staggered configuration, so that at least a portion of each electrode may be exposed, or the conductive layers can be directly above each other. Alternatively, multiple electrodes can be fabricated at the same time (e.g., simultaneously) on the same insulating substrate. The conductive layers can be horizontally displaced from each other. The electrodes can be further be configured in any way that allows the electrodes to contact fluid when inserted into a body of a patient.

Sensors of embodiments can include conductive layers alternating with the insulating layers. In between every two conductive layers there may be an insulating layer that serves to isolate each conductive layer so that there is no trace communication between the layers. Apertures can be formed in a top insulating cover layer, or the top layer can be a conductive layer. Electrodes can be in a vertical orientation atop each other, or spaced sideways so that they are not directly on top of each other (e.g., horizontally displaced). Conductive pathways that lead to conductive contacts can be similarly positioned. The apertures can be made through photolithographic development, laser ablation, chemical milling, etching, or the like. The exposed electrodes and/or contacts can also undergo secondary processing through the apertures, such as additional plating processing, to prepare the surfaces, and/or strengthen the conductive regions.

Typically, the conductive layers (or electrodes) are formed by any of a variety of methods known in the art such as photoresist, etching and rinsing to define the geometry of the active electrodes. The electrodes can then be made electrochemically active, for example by electrodeposition of platinum black for the working and counter electrode, and silver followed by silver chloride on the reference electrode. The sensor chemistry layer is then disposed on the conductive layer by a method other than electrochemical deposition, usually followed by vapor crosslinking, for example with a dialdehyde, such as glutaraldehyde, or a carbodiimide.

One or more sensors can be formed on a rigid flat substrate, such as a polymer, glass, ceramic, composite, or metal. When finished, the sensors may be removed from the rigid flat substrate by a suitable method, such as laser cutting. Other materials that can be used for the substrate include, but are not limited to, stainless steel, aluminum, and plastic materials. Flexible sensors can be formed in a manner which is compatible with photolithographic mask and etch techniques, but where the sensors are not physically adhered or attached directly to the substrate. Each sensor thus comprises a plurality of thin film electrodes formed between an underlying insulating base layer and an insulating cover layer.

A flexible electrochemical sensor can be constructed according to thin film mask techniques to include elongated thin film conductors embedded or encased between layers of a selected insulating material such as polyimide film or sheet. The sensor electrodes at a tip end of the sensor distal segment are exposed through one of the insulating layers for direct contact with patient fluids, such as blood and/or interstitial fluids, when the sensor is transcutaneously, subcutaneously, or intravenously placed. The proximal segment and the contacts thereon are adapted for electrical connection to a suitable monitor for monitoring patient condition in response to signals derived from the sensor electrodes. The sensor electronics may be separated from the sensor by wire or be attached directly on the sensor. For example, the sensor may be housed in a sensor device including a housing that contains all of the sensor electronics, including any transmitter necessary to transmit data to a monitor or other device. The sensor device alternatively may include two portions, one portion housing the sensor and the other portion housing the sensor electronics. The sensor electronics portion could attach to the sensor portion in a side-to-side or top-to-bottom configuration, or any other configuration that would connect the two portions together.

If the sensor electronics are in a housing separated by a wire from the sensor, the sensor electronics housing may be adapted to be placed onto the user's skin or placed on the user's clothing in a convenient manner. The connection to the monitor may be wired or wireless. In a wired connection, the sensor electronics may essentially be included in the monitor instead of in a housing with the sensor. Alternatively, sensor electronics may be included with the sensor as described above. A wire could connect the sensor electronics to the monitor. Examples of wireless connection include, but are not limited to, radio frequency, infrared, WiFi, ZigBee and Bluetooth. Additional wireless connections further include single frequency communication, spread spectrum communication, adaptive frequency selection and frequency hopping communication. In further embodiments, some of the electronics may be housed on the sensor and other portions may be in a detachable device. For example, the electronics that process and digitize the sensor signal may be with the sensor, while data storage, telemetry electronics, and any transmission antenna may be housed separately. Other distributions of electronics are also possible, and it is further possible to have duplicates of electronics in each portion. Additionally, a battery may be in one or both portions. In further embodiments, the sensor electronics may include a minimal antenna to allow transmission of sensor data over a short distance to a separately located transmitter, which would transmit the data over greater distances. For example, the antenna could have a range of up to 6 inches, while the transmitter sends the information to the display, which could be over 10 feet away. The overall sensor height of sensors fabricated by such methods (from base to top insulating layer) can be on the order of microns (e.g., less than 250 microns, less than 100 microns, less than 50 microns, or less than 25 microns). The base layer can be about 12 microns and each insulating layer can be about 5 microns. The conductive/electrode layers can be several thousand angstroms in thickness. Any of these layers could be thicker if desired. The overall width of the sensor can be as small as about 250 microns or less or 150 microns or less. The length of the sensor can be selected depending upon the depth and/or method of insertion. For example, for transcutaneous or subcutaneous sensing, the sensor length may be about 2 mm to 5 mm, or for intravenous sensing up to about 3 cm or more. Additional methods for manufacturing the sensors and membranes described herein are described in U.S. Provisional Application No. 61/222,815 filed Jul. 2, 2009 and U.S. patent application Ser. No. 12/829,337, filed Jul. 1, 2010, entitled "ANALYTE SENSORS AND METHOD OF MAKING SAME," each of which is incorporated by reference herein in its entirety.

In certain embodiments, the sensor (e.g., sensor 100) is configured and arranged for multi-axis bending. The term "bending," as used herein, is a broad term, and is to be given its ordinary and customary meaning to a person of ordinary skill in the art (and is not to be limited to a special or customized meaning), and refers without limitation to movement that causes the formation of a curve, or a condition that is characterized as being not rigid or not straight. In general, a structure capable of multi-axis bending is configured for substantial bending in (e.g., within, along) two or more planes (e.g., about two or more axes). In one exemplary embodiment, with respect to the in vivo portion of a continuous analyte sensor, there is no preferred bending point or location for a bend and/or flex to occur. Accordingly, in some embodiments, the sensor is configured and arranged to bend along a plurality of planes, such as within 2, 3, 4, 5, 6, 7, 8, 9, 10 or more planes. In a further embodiment, multi-axis bending includes flexing (e.g., curving, bending, deflecting) in at least three directions. For example, in some embodiments, the sensor is configured to bend and/or flex in 4, 5, 6, 7, 8, 9, 10 or more directions. In further embodiment, the sensor is configured and arranged without preferred bending points and/or locations along its in vivo portion. Accordingly, in these embodiments, the sensor is configured and arranged for multi-axis bending at any point along the length of the sensor's in vivo portion (e.g., non-preferential bending). In some embodiments, a sensor with multi-axis bending does not have a preferred bending radius, thereby allowing substantial bending in 360°. Since movements by the host can cause the sensor to bend, it is believed that multi-axis bending extends sensor lifetime (e.g., by preventing sensor breakage and/or degradation) and affords greater host comfort (e.g., by moving/flexing/bending with, instead of resisting, the host's movements, and/or causing tissue damage).

Multi-axis bending of the certain embodiments includes a combination of strength and flexibility. The material properties of the components of the in vivo portion of the sensor (e.g., the elongated conductive body, the conductive core, the insulator and/or the membrane) and/or the geometry of the in vivo portion of the sensor impart this combination of strength and flexibility that enables multi-axis bending to the sensor. Material properties can be described in a variety of ways known in the art. For example, tensile strength is the stress at which a material breaks or permanently deforms. Ultimate tensile strength (UTS) is the maximum stress a material can withstand when subjected to tension, compression or shearing, and is the maximum stress on a stress-strain curve created during tensile tests conducted on a sensor. Young's modulus (E) is a measure of the stiffness of an isotropic elastic material, and can be determined from the slope of a stress-strain curve described above. Yield strength is a measure of the ability to bend and not snap (e.g., break). Fatigue is a measure of the progressive and localized structural damage (e.g., the failure or decay of mechanical properties) that occurs when a material is subjected to cyclic loading (e.g., stress). The maximum stress values are less than the ultimate tensile stress limit, and may be below the yield stress limit of the material.

Fatigue life is the number of cycles of deformation required to bring about failure of the test specimen under a given set of oscillating conditions. Fatigue life can be determined by fatigue testing, such as by testing with a device configured to repeatedly bend, pull, compress and/or twist the device. For example, fatigue-life testing can be performed on a plurality of sensors and then the tensile strength and/or Young's modulus mathematically determined from data collected during the sensor testing. For example, sensors to be tested can include pre-bent elbows at a predetermined angle, such as but not limited to into a 10, 20, 30, 40, 50, 60, 70 or 80-degree elbows, wherein the elbows have a bend radius of about 0.015, 0.02, 0.025, 0.03, 0.035, 0.04, 0.045 or 0.05-inches. Using a fatigue-testing machine (e.g., via a Bose ElectroForce® 3200 fatigue-testing unit, Bose Corporation, Eden Prairie, Minn., USA), the elbows can be repeatedly pulled open and/or pushed closed a predetermined amount, such as but not limited to 1, 2, 3, 4, 5, 6, 7, 8, 9, 10, 11, 12, 13, 14, or 15-mm or more, and/or through a plurality of deflection ranges, such as but not limited to at a cycle frequency of about 1, 2, 3, 4, 5, 6, 7, 8, 9, 10, 11, 12, 13, 14, 15, 16, 70, 18, 19 or 20 Hertz. For example, a peak-to-peak deflection of 4-mm means that the elbow was pushed in the closed direction 2-mm from its initial condition, as well as pulled open 2-mm from its initial condition. The number of cycles (of pulling/pushing) to failure of the device (e.g., breaking, buckling, cracking, fraying) can be counted. In one exemplary embodiment, 60° elbows having a bend radius of about 0.025-inches (e.g. bent sensors) can withstand at least about 5,000-10,000 cycles of 5-mm peak-to-peak displacement. In another exemplary embodiment, the elbows can withstand at least about 10,000-70,000 cycles of 4-mm peak-to-peak displacement. In another exemplary embodiment, the elbows can withstand at least about 1,000,000-10,000,000 cycles of 2-mm peak-to-peak displacement. In another exemplary embodiment, the elbows can withstand at least about 100,000-600,000 cycles of 3-mm peak-to-peak displacement.

These data (above) can be used to calculate the sensor's tensile strength, Young's modulus, and the like, as is understood by one skilled in the art. In some embodiments, the sensor is configured for multi-axis bending to an angle of at least about 60°, 70°, 80°, 90°, 100°, 110° or 120° or more. In some embodiments, a sensor with multi-axis bending does not have a preferred bending radius, thereby allowing substantial bending in 360° about the sensor's longitudinal axis. In some embodiments, the sensor is configured and arranged such that the ultimate tensile strength of the elongated conductive body is from about less than about 80, 80, 90, 100, 110, 120, 130, 140 or 150 kPsi (551 MPa) to about 160, 170, 180, 190, 200, 210, 220 or 500 kPsi (1517 MPa) or more. In some embodiments, the Young's modulus of the sensor is from more than about 165, 165, 170, 175, 180, 185 or 190 GPa to less than about 195, 200, 205, 210, 215 or 220 GPa. In some embodiments, the yield strength of the elongated conductive body (e.g., the sensor, conductive core) is at least about 70, 100, 150, 200, 250, 300, 350, 400, 450, 500, 600, 700, 800, 900, 1000, 1250, 1500, 1750, 2000, 2250, 2500, 2750, or 3000 MPa or more. In some embodiments, the fatigue life of the sensor is at least about 1,000, 2,000, 3,000, 4,000, or 5,000 cycles or more when the sensor is pre-bent into an elbow comprising a bend angle of at least 60° and a bend radius of about 0.05-inches or less. In some embodiments, the fatigue life of the sensor is at least 1,000 cycles of flexing of from about 28° to about 110° and a bend radius of about 0.125-inches.

The analyte sensors (e.g., electrodes and membrane systems) of some embodiments are coaxially and/or concentrically formed. Namely, the electrodes (e.g., elongated conductive bodies) and/or membrane systems all share the same central axis. While not wishing to be bound by theory, it is believed that a coaxial design of the sensor enables a symmetrical design without a preferred bend radius. In contrast to conventional sensors comprising a substantially planar configuration that can suffer from regular bending about the plane of the sensor, the coaxial design of the certain embodiments do not have a preferred bend radius and therefore are not subject to regular bending within and/or about a particular plane (which can cause fatigue failures and the like). However, non-coaxial sensors can be implemented with the sensor system of the some embodiments.

In addition to the above-described advantages, the coaxial sensor design of some embodiments enables the diameter of the connecting end of the sensor (proximal portion) to be substantially the same as that of the sensing end (distal portion). For sensors configured and arranged for implantation into a host's circulatory system, this configuration enables the protective slotted sheath to insert the sensor into a catheter and subsequently slide back over the sensor and release the sensor from the protective slotted sheath, without complex multi-component designs. For sensors configured for transcutaneous implantation, this configuration enables a needle to implant the sensor and then slide over the sensor when the needle is withdrawn.

FIG. 1B is a schematic illustrating an elongated conductive body 102 (also referred to as the "elongated body") in one embodiment, wherein the elongated conductive body is formed from at least two materials and/or layers of conductive material, as described in greater detail elsewhere herein. In some embodiments, the term "electrode" can be used herein to refer to the elongated conductive body, which includes the electroactive surface that detects the analyte. In some embodiments, the elongated conductive body provides an electrical connection between the electroactive surface (e.g., working electrode) and sensor electronics (not shown). In certain embodiments, each electrode (e.g., the elongated conductive body, on which the electroactive surface is located) is formed from a fine wire with a diameter of from about 0.001 inches or less to about 0.01 inches or more, for example, and is formed from, e.g., a plated insulator, a plated wire, or bulk electrically conductive material. For example, in some embodiments, the wire and/or elongated conductive body used to form a working electrode is about 0.002, 0.003, 0.004, 0.005, 0.006, 0.007, 0.008, 0.009, 0.01, 0.015, 0.02, 0.025, 0.03, 0.035, 0.04 or 0.045 inches in diameter.

In some embodiments, the working electrode (e.g., the elongated conductive body including an electroactive surface) comprises a wire formed from a conductive material, such as platinum, platinum-iridium, palladium, graphite, gold, carbon, conductive polymer, alloys, or the like In some embodiments, the working electrode is formed of platinum-iridium or iridium wire. In general, platinum-iridium and iridium materials are generally stronger (e.g., more resilient and less likely to fail due to stress or strain fracture or fatigue). While not wishing to be bound by theory, it is believed that platinum-iridium and/or iridium materials can facilitate fabrication of a wire with a smaller diameter to further decrease the maximum diameter (size) of the sensor (e.g., in vivo portion). Advantageously, with respect to intravascularly-implanted sensors, a smaller sensor diameter both reduces the risk of clot or thrombus formation (or other foreign body response) and allows the use of smaller catheters.

Referring to FIG. 1B, in some embodiments, the elongated conductive body 102 comprises at least two concentric layers (e.g., a composite structure). In a further embodiment, the elongated conductive body comprises a core 110 and a first layer 112. The core is formed from one of the at least two materials referred to above. For example, the core can be formed of a polymer, a metal, an alloy and the like. In some embodiments, the core is formed from a conductive polymer, such as but not limited to polyaniline and polypyrrole. In some embodiments, a conductive material is added to (e.g., mixed with and/or applied to) a non-conductive polymer, whereby the polymer core is rendered conductive. For example, in some embodiments, one or more conductive metals (e.g., carbon, gold, platinum, iridium, etc.), such as but not limited to particles, can be mixed with the uncured polymer, which can be formed into the core. Alternatively, the core can comprise an inner core and an outer core, in some embodiments. For example, platinum, iridium or gold particles can be ion-implanted on the surface of a polymer inner core, such that the particles form an outer core. For example, a polymer filament fiber can be ion-implanted with gold, such that the treated filament fiber is conductive. In some embodiments, the core is formed from a metal, such as but not limited to at least one of stainless steel, tantalum, titanium and/or an alloy thereof. For example, in one embodiment, the core is formed of an extruded stainless steel, tantalum, titanium and/or an extruded alloy. In some embodiments, the material of the core is processed to provide the strength and flexibility necessary for multi-axis bending. Processing the metal changes its properties, such as but not limited to by compressing and/or rearranging the metal's crystalline lattice. For example, tempering can make a metal less brittle and more springy; hardening can make a metal hold its shape better. Accordingly, in certain embodiments, the core is formed of a metal that has been processed to provide the requisite combination of strength and flexibility (e.g., an ultimate tensile strength of from about less than 80, 80, 90, 100, 110, 120, 130, 140 or 150 kPsi (551 MPa) to about 160, 170, 180, 190, 200, 210, 220 or 500 kPsi (3297 MPa)) or more. For example, in some embodiments, the core is formed from a metal that has been annealed, tempered, normalized, hardened, work-hardened, full-processed, case hardened, draw air hardened, cold worked and/or the like, to render it more stiff. In one embodiment, the core is formed from full-processed platinum. In another embodiment, the core is formed from work-hardened platinum-iridium.

In some embodiments, the surface of the elongated conductive body and/or the core is treated to remove initiation sites (e.g., locations/points of irregularity, where sensor breaking tends to begin), to smooth and/or clean the surface, to prepare it for application of the next material, and/or the like. Suitable treatments include but are not limited to electropolishing, etching, application of a tie layer, electro-deposition, and electrostatic deposition.

In some embodiments, the elongated conductive body (and/or the core, and/or the sensor) is wire-shaped. However, the wire-shape can include one of a variety of cross-sectional shapes, such as but not limited to a circle, an oval, a rectangle, a triangle, a cross, a star, a cloverleaf, an X-shape, a C-shape, an irregular or other non-circular configuration, and the like. The elongated conductive body includes a diameter and/or a smallest dimension (e.g., width) of about less than 0.002, 0.002, 0.003, 0.004, 0.005, 0.006, 0.007, 0.008, 0.009, 0.01, 0.015, 0.02, 0.025, 0.03, 0.035, 0.04 or 0.045 inches or more in diameter. The elongated conductive body can be provided as a reel and/or extended lengths that are subsequently processed and/or singularized into individual sensor lengths.

In some embodiments, the elongated conductive body 102 comprises a first layer 112 applied to a core 110. In some embodiments, the first layer is applied to the core such that they are electrically connected (e.g., in electrical contact, such that a current can pass therebetween). The first layer can be formed of a variety of conductive materials, such as but not limited to at least one of platinum, platinum-iridium, gold, palladium, iridium, graphite, carbon, conductive polymers and an alloy. In certain embodiments, the first layer is relatively thin, such as but not limited to a thickness of from about less than 50, 50, 55, 60, 65, 70, 75, 80, 85, 90, 95 or 100 micro-inches to about 125, 150, 175, 200, 225, 250, 275 or 300 micro-inches, or thicker. As is described elsewhere herein with greater detail, at least a portion of the surface of the first layer provides the sensor's electroactive surface (e.g., working electrode). For example, as described herein, in some embodiments, the electroactive surface is exposed through a window formed in the insulator. In some embodiments, the surface of the applied first layer is treated prior to application of membrane materials, such as to optimize the surface for membrane attachment and for function as an electroactive surface. For example, the surface can be cleaned, smoothed, etched, and the like. Advantageously, forming the conductive core of an inexpensive yet strong and flexible inner body with a thin layer of the costly electroactive surface material enables a substantial reduction in material costs.

In some embodiments, a conductive paste comprising a mixture of material (e.g., an ink) and an enzyme (e.g., glucose oxidase) may be applied to the layer surrounding the core, or applied directly to the core. The conductive paste may also include an interference reducing substance, mediator, or diffusion limiting polymers. Use of the conductive paste may reduce or eliminate the need for certain membrane layers (e.g., the enzyme layer).

The first layer 112 can be applied to the core 110 using a variety of manufacturing methods. For example, in some embodiments, the first layer is co-extruded with the core using known techniques, such as but not limited to metal-on-metal or metal-on-polymer extrusion techniques. Some useful co-extrusion techniques are described in U.S. Pat. No. 7,416,802, U.S. Pat. No. 7,268,562, U.S. Pat. No. 7,153,458, U.S. Pat. No. 7,280,879, U.S. Pat. No. 5,324,328 and U.S. Pat. No. 6,434,430. In one exemplary embodiment, a stainless steel inner body is co-extruded with a platinum first layer, such as but not limited to through a die, to form a thin reel of 0.005-inch diameter wire having a stainless steel core with a 100-micro-inch layer of platinum thereon.

In some embodiments, the first layer 112 is applied to the core 110 (which, in some embodiments, is pre-treated as described above) using a thin film or thick film technique (e.g., spraying, electro-depositing, vapor-depositing, dipping, spin coating, sputtering, evaporation, printing or the like). For example, in one embodiment, the first layer is applied by dipping the core into a solution of the first layer material and drawing out the core at a speed that provides the appropriate first layer thickness. However, any known thin or thick film method can be used to apply the first layer to the core, as will be appreciated by one skilled in the art. Some examples of thin and/or thick film manufacturing techniques can be found in U.S. Patent Application Publication No. US-2005-0181012-A1, U.S. Patent Application Publication No. US-2006-0036143-A1, U.S. Patent Application Publication No. US-2007-0163880-A1, U.S. Patent Application Publication No. US-2006-0270923-A1, U.S. Patent Application Publication No. US-2007-0027370-A1, U.S. Patent Application Publication No. US-2006-0015020-A1, U.S. Patent Application Publication No. US-2006-0189856-A1, U.S. Patent Application Publication No. US-2007-0197890-A1, U.S. Patent Application Publication No. US-2006-0257996-A1, U.S. Patent Application Publication No. US-2006-0229512-A1, U.S. Patent Application Publication No. US-2007-0173709-A1, U.S. Patent Application Publication No. US-2006-0253012-A1, U.S. Patent Application Publication No. US-2006-0195029-A1, U.S. Patent Application Publication No. US-2008-0119703-A1, U.S. Patent Application Publication No. US-2008-0108942-A1, and U.S. Patent Application Publication No. US-2008-0200789-A1.

In some embodiments the first layer 112 is deposited onto the core 110. For example, in some embodiments, the first layer is plated (e.g., electroplated) onto the core. In one exemplary embodiment, a thin layer of platinum is plated onto a tantalum core by immersing the inner body in a platinum-containing solution and applying a current to the inner body for an amount of time, such that the desired thickness of platinum first layer is generated and/or achieved. Description of deposition methods and devices therefore can be found in U.S. Pat. No. 7,427,338, U.S. Pat. No. 7,425,877, U.S. Pat. No. 7,427,560, U.S. Pat. No. 7,351,321 and U.S. Pat. No. 7,384,532.

In still other embodiments, the core 110 is embedded in insulator and a working electrode body 112 is attached, such that the core and the working electrode body are electrically (e.g., functionally, operably) connected, such as described with reference to FIGS. 3A and 3B. For example, in some embodiments, a working electrode body is formed as a foil that is attached to the core, such as with adhesive, welding and/or an intermediate layer of conductive material to provide adhesion between the core and the working electrode body material (e.g., at tie layer). In some embodiments, multiple layers are applied on top of the core. In some embodiments, each layer possesses a finite interface with adjacent layers or together forms a physically continuous structure having a gradient in chemical composition. In another embodiment, the working electrode body is a C-clip or snap-ring that is attached by compression about and/or around the core. In some embodiments, the working electrode body is attached over a window. In other embodiments, there is no window, instead, the working electrode body is configured to pierce the insulator and to physically contact the underlying core, such that the working electrode body and the core are operably connected. In some embodiments, a conductive metal C-clip is attached to the core with adhesive, welding and/or a tie layer. In yet another embodiment, an adhesive is attached to the core, followed by wrapping a conductive foil therearound.

The elongated conductive body 102 can be manufactured using a variety of manufacturing techniques. In some embodiments, the first layer 112 is applied to the core 110 in a substantially continuous process. For example, in some embodiments, the manufacturing of the elongated conductive body involves a reel-to-reel process. In other embodiments, a sheet-fed technique is used. In some embodiments, application of the first layer to the core can be by either a semi-automated or fully-automated process. Automation of some or all manufacturing steps generally requires the use of one or more machines, such as robotic devices, that are configured and arranged to perform the manufacturing step(s). In some embodiments, one manufacturing step can be automated, such as production of the elongated conductive body. However, in other embodiments, two or more of the manufacturing steps can be automated. For example, a device can be configured to perform two or more of the steps, or two or more devices can perform the steps. In some embodiments, when multiple devices are used, the devices are connected, coupled together, interconnected, and linked functionally and/or physically. For example, in some embodiments, the product of one device is fed directly into the next device, and so on. In one exemplary embodiment, a reel of previously manufactured core, such as a stainless-steel, tantalum or titanium wire, can be fed substantially continuously through a device configured to electroplate the core with platinum, gold, carbon or the like, such that a reel of plated wire is generated. For example, a manufacturing device and/or system can be configured to automatically co-extrude stainless-steel and platinum to generate/produce a reel of wire-shaped elongated conductive body comprising a stainless-steel core and platinum first layer. Examples of continuous manufacturing processes can be found in U.S. Pat. No. 6,103,033, U.S. Pat. No. 5,879,828, U.S. Pat. No. 5,714,391, U.S. Pat. No. 7,429,552, U.S. Pat. No. 7,402,349 and U.S. Pat. No. 7,387,811.

In a further embodiment, the first layer comprises an electroactive surface (e.g., the portion exposed through the window 106). The exposed electroactive surface of the first layer is the working electrode, in some embodiments. For example, if the sensor is an enzymatic electrochemical analyte sensor, the analyte enzymatically reacts with an enzyme in the membrane covering at least a portion of the electroactive surface, which can generate electrons ($e^-$) that are detected at the electroactive surface as a measurable electronic current. For example, in the detection of glucose wherein glucose oxidase produces hydrogen peroxide as a byproduct, hydrogen peroxide reacts with the surface of the working electrode producing two protons ($2H^+$), two electrons ($2e^-$) and one molecule of oxygen ($O_2$), which produces the electronic current being detected.

As previously described with reference to FIG. 1A and as shown in FIG. 1C, an insulator 104 is disposed on (e.g., located on, covers) at least a portion of the elongated conductive body 102. In some embodiments, the sensor is configured and arranged such that the elongated body includes a core 110 and a first layer 112, and a portion of the first layer is exposed via window 106 in the insulator. In other embodiments, the sensor is configured and arranged such that the elongated body includes a core embedded in an insulator, and a portion of the core is exposed via the window in the insulator. For example, in some embodiments, the insulating material is applied to the elongated body (e.g., screen-, ink-jet and/or block-printed) in a configuration designed to leave a portion of the first layer's surface (or the core's surface) exposed. For example, the insulating material can be printed in a pattern that does not cover a portion of the elongated body. In another example, a portion of the elongated body is masked prior to application of the insulating material. Removal of the mask, after insulating material application, exposes the portion of the elongated body.

In some embodiments, the insulating material 104 comprises a polymer, for example, a non-conductive (e.g., dielectric) polymer. Dip-coating, spray-coating, vapor-deposition, printing and/or other thin film and/or thick film coating or deposition techniques can be used to deposit the insulating material on the elongated body and/or core. For example, in some embodiments, the insulating material is applied as a layer of from about less than 5, 5, 10 or 15-microns to about 20, 25, 30 or 35-microns or more in thickness. In some embodiments, the insulator is applied as a single layer of material. In other embodiments, the insulator is applied as two or more layers, which are comprised of either the same or different materials. In some embodiments, the insulating material comprises at least one of polyurethane, polyimide and parylene. In one embodiment, the insulating material comprises parylene, which can be an advantageous polymer coating for its strength, lubricity, and electrical insulation properties. Generally, parylene is produced by vapor deposition and polymerization of para-xylylene (or its substituted derivatives). However, any suitable insulating material, such as but not limited to a dielectric ink, paste or paint, can be used, for example, fluorinated polymers, polyethyleneterephthalate, polyurethane, polyimide, other nonconducting polymers, or the like. In some embodiments, glass or ceramic materials can also be employed. Other materials suitable for use include surface energy modified coating systems such as are marketed under the trade names AMC18, AMC148, AMC141, and AMC321 by Advanced Materials Components Express of Bellafonte, Pa. In some alternative embodiments, however, the conductive core may not require a coating of insulator. In certain embodiments, the insulating material defines an electroactive surface of the analyte sensor (e.g., the working electrode). For example, in some embodiments a surface of the conductive core (e.g., a portion of the first layer 112) either remains exposed during the insulator application or a portion of applied insulator is removed to expose a portion of the conductive core's surface, as described above.

In some embodiments, in which the sensor has an insulated elongated body, a portion of the insulating material is stripped or otherwise removed, for example, by hand, excimer lasing, chemical etching, laser ablation, grit-blasting (e.g., with sodium bicarbonate or other suitable grit), or the like, to expose the electroactive surfaces. In one exemplary embodiment, grit blasting is implemented to expose the electroactive surface(s), for example, by utilizing a grit material that is sufficiently hard to ablate the polymer material yet also sufficiently soft so as to minimize or avoid damage to the underlying metal electrode (e.g., a platinum electrode). Although a variety of "grit" materials can be used (e.g., sand, talc, walnut shell, ground plastic, sea salt, and the like), in some embodiments, sodium bicarbonate is an advantageous grit-material because it is sufficiently hard to ablate, e.g., a parylene coating without damaging, e.g., an underlying platinum conductor. One additional advantage of sodium bicarbonate blasting includes its polishing action on the metal as it strips the polymer layer, thereby eliminating a cleaning step that might otherwise be necessary. In some embodiments, the opening in the insulator, through which the surface of the first layer is exposed, is referred to as a "window" 106.

Due to the small sizes of the sensors in some embodiments, it can be difficult to precisely remove the insulator over one insulated conductive core without affecting, and possibly removing, the insulator over an adjacent conductive core or over other parts of the sensor. However, in some embodiments, the insulator is configured such that the precision of laser ablation is substantially improved. For example, in some embodiments, the insulator is configured such that two different types of lasers can be used to ablate separate portions of the insulator. For example, if the insulators of two elongated bodies are different materials (i.e. one is polyurethane and another is TEFLON® or another type of polytetrafluoroethylene), then it is possible to selectively ablate the insulator off of one of the elongated bodies and to not remove insulator from the other elongated body in the same region of the sensor. In some embodiments, the two insulation materials require different laser parameters for optimal ablation, such that a first laser setup could be used to ablate a first material but not the second material, and a second laser setup could be used to ablate a second material but not the first material. In another example, for a sensor containing two elongated bodies, the insulator covering one elongated body can be configured for laser ablation with an ultraviolet laser (e.g., using a wavelength of about 200 nm), and the other elongated body can be configured for laser ablation with an infrared laser (e.g., using a wavelength of about 1000 nm). In another embodiment, the insulator materials are selected such that the insulator of a first elongated body requires a substantially higher laser power to be ablated than the insulator of a second elongated body. For example, the insulator over the two elongated bodies can be the same, except that the insulator of the first elongated body is thicker than the insulator of the second elongated body. In another example, the insulator on each of the elongated bodies has a different thickness, such that a single laser is used to remove the insulator over both cores, except that the window in the thinner insulator is formed more quickly than the window in the thicker insulator. For example, the insulator of one elongated body can be from about 0.0001 inches to about 0.0003 inches in thickness, and the insulator of one elongated body can be from about 0.0008 inches to about 0.0010 inches in thickness. In yet another example, a colorant can be added to the insulator of one of the elongated bodies, to modify the amount of energy that is absorbed from the laser. For example, adding a dark colorant or other absorptive material to the first insulator but not the second insulator can cause the first insulator to absorb much more energy of the laser than the non-colored second insulator. In this way, a small amount of laser energy would ablate one wire but not the other, but a large amount of laser energy would ablate both. As is understood by one skilled in the art, the setup of the laser can be adjusted, to fine-tune the insulator removal process. For example, the laser pulse width and power level can be adjusted to modify and/or modulate the amount of insulator removed, the rate of removal, and/or the like. This principle can be used for assemblies (e.g., sensors) of three or more elongated bodies (e.g., cores, wires). The same principle may be applied to chemical ablation, where different solvents are required for the different insulation layers such that they can be selectively ablated. The same principle may also be used with plasma ablation, where different plasma settings or amounts of energy are required to ablate the different materials.

The electroactive surface of the working electrode is exposed by formation of a window 106 in the insulator 104. The electroactive window 106 of the working electrode is configured to measure the concentration of an analyte. For example, in an enzymatic electrochemical sensor for detecting glucose, the working electrode measures the hydrogen peroxide produced by an enzyme catalyzed reaction of the analyte being detected and creates a measurable electronic current. For example, in the detection of glucose wherein glucose oxidase (GOX) produces hydrogen peroxide as a byproduct, hydrogen peroxide reacts with the surface of the working electrode producing two protons ($2H^+$), two electrons ($2e^-$) and one molecule of oxygen ($O_2$), which produces the electronic current being detected. The sensor can be configured to detect other analytes by substituting an enzyme that metabolizes the analyte of interests for GOX, as is understood by one skilled in the art.

In the embodiments illustrated in FIGS. 1A, 1C, 2A, 4B, and 5A through 5D, a radial window 106 is formed through the insulating material 104 to expose a circumferential electroactive surface of the working electrode (e.g., first layer 112). In other embodiments, such as those shown in FIGS. 3A, 3B, 4A, 5B and 5D, a radial or non-radial window 106 is formed (e.g., for electrical connection to the working electrode body 112) by removing only a portion of the insulating material 104. Additionally, a section of electroactive surface of the reference electrode 114 is exposed, in some embodiments (not shown). For example, the sections of electroactive surface can be masked during deposition of an outer insulating layer and/or etched after deposition of an outer insulating layer. In some embodiments, a plurality of micro-windows comprises the electroactive surface of the working electrode, wherein the sum of the micro-window surface areas is substantially equal to the window 106 electroactive surface area. In certain embodiments, the plurality of micro-windows are spaced and/or staggered along a length of the conductive core.

In some embodiments, the window 106 (or the working electrode body 112) is sized to provide an electroactive surface (e.g., working electrode) having an area such that the sensor functions in the picoAmp range (e.g., when the analyte is glucose, a sensitivity of from about 1 to about 300 pA per mg/dL glucose, or a sensitivity of from about 5 to about 100 pA per mg/dL glucose, or from about 5 to about 25 pA per mg/dL glucose, and or from about 4 to about 7 pA per mg/dL). For an electrode having an electroactive surface area of about 0.3 $mm^2$, the current density (sensitivity divided by surface area) is or from about 17 $pA/mg/dL/mm^2$ to about 1000 $pA/mg/dL/mm^2$, or from about 3 $pA/mg/dL/mm^2$ to about 83 $pA/mg/dL/mm^2$, or 13 $pA/mg/dL/mm^2$ to about 23 $pA/mg/dL/mm^2$. In some embodiments, the working electrode has a diameter of from about 0.001 inches or less to about 0.01 inches or more, or from about 0.002 inches to about 0.008 inches, or from about 0.004 inches to about 0.005 inches. The length of the window can be from about 0.1 mm (about 0.004 inches) or less to about 2 mm (about 0.078 inches) or more, or from about 0.5 mm (about 0.02 inches) to about 0.75 mm (0.03 inches). In such embodiments, the exposed surface area of the working electrode is from about 0.000013 $in^2$ (0.0000839 $cm^2$) to about 0.0025 $in^2$ (0.016129 $cm^2$) (assuming a diameter of from about 0.001 inches to about 0.01 inches and a length of from about 0.004 inches to about 0.078 inches). The exposed surface area of the working electrode is selected to produce an analyte signal with a current in the picoAmp range. However, a current in the picoAmp range can be dependent upon a variety of factors, for example the electronic circuitry design (e.g., sample rate, current draw, A/D converter bit resolution, etc.), the membrane system (e.g., permeability of the analyte through the membrane system), and the exposed surface area of the working electrode. Accordingly, the exposed electroactive working electrode surface area can be selected to have a value greater than or less than the above-described ranges taking into consideration alterations in the membrane system and/or electronic circuitry. In certain embodiments of a glucose sensor, it can be advantageous to minimize the surface area of the working electrode while maximizing the diffusivity of glucose in order to optimize the signal-to-noise ratio while maintaining sensor performance in both high and low glucose concentration ranges.

In some embodiments, the exposed surface area (e.g., electroactive surface) of the working (and/or other) electrode (e.g., conductive core) can be increased by altering the cross-section of the electrode itself. For example, in some embodiments the cross-section of the working electrode can be defined by a cross, star, cloverleaf, ribbed, dimpled, ridged, irregular, or other non-circular configuration; thus, for any predetermined length of electrode, a specific increased surface area can be achieved (as compared to the area achieved by a circular cross-section). Increasing the surface area of the working electrode can be advantageous in providing an increased signal responsive to the analyte concentration, which in turn can be helpful in improving the signal-to-noise ratio, for example. In some embodiments, application of the insulator to the conductive core can be accomplished by a substantially continuous process, which can be semi- or fully-automated, such as in a manner similar to some methods described for formation/manufacture of the conductive core.

In some embodiments, the sensor 100 further comprises a reference electrode 114. The reference electrode 114, which can function as a reference electrode alone, or as a dual reference and counter electrode, is formed from silver, silver/silver chloride, or the like. In some embodiments, the reference electrode 114 is juxtapositioned and/or twisted with or around at least a portion of the sensor. For example, in FIG. 2A, the reference electrode is a silver wire helically twisted and/or wrapped and/or wound around the working electrode. This assembly of "wires" is then optionally coated or adhered together with an insulating material, similar to that described above, so as to provide an insulating attachment.

In some embodiments, a silver wire is formed onto and/or fabricated into the sensor and subsequently chloridized to form silver/silver chloride reference electrode. Advantageously, chloridizing the silver wire as described herein enables the manufacture of a reference electrode with optimal in vivo performance. Namely, by controlling the quantity and amount of chloridization of the silver to form silver/silver chloride, improved break-in time, stability of the reference electrode and extended life has been shown with some embodiments. Additionally, use of silver chloride as described above allows for relatively inexpensive and simple manufacture of the reference electrode.

Referring to FIGS. 1B-1C, in some embodiments, the reference electrode 114 comprises a silver-containing material applied over at least a portion of the insulating material 104. In some embodiments, the silver-containing material is applied using thin film and/or thick film techniques, such as but not limited to dipping, spraying, printing, electro-depositing, vapor deposition, spin coating, and sputter deposition, as described elsewhere herein. For example, a silver or silver-chloride-containing paint (or similar formulation) is applied to a reel of the insulated conductive core, in one embodiment. In another example, the reel of insulated elongated body (or core) is cut into single unit pieces (e.g., "singularized") and a silver-containing ink is pad printed thereon. In still other embodiments, the silver-containing material is applied as a silver foil. For example, an adhesive can be applied to an insulated elongated body, around which the silver foil is then wrapped in. Alternatively, the sensor can be rolled in Ag/AgCl particles, such that a sufficient amount of silver sticks to and/or embeds into and/or otherwise adheres to the adhesive for the particles to function as the reference electrode. In some embodiments, the sensor's reference electrode includes a sufficient amount of chloridized silver that the sensor measures and/or detects the analyte for at least three days.

In some embodiments, the sensor is formed from an elongated body 102 (e.g., elongated conductive body), such as that shown in FIG. 1B, wherein the elongated body includes a core 110, a first layer 112, an insulator 104, and a layer of silver-containing material 114. In some embodiments, such as that shown in FIG. 1C, the electroactive surface of the elongated body (e.g., also the (electroactive) surface of the first layer 112) is exposed by formation of a window 106 through both the silver-containing material and the insulator. In one exemplary embodiment, the elongated body of FIG. 1B is provided as an extended length on a reel that is singularized into a plurality of pieces having a length (e.g., less than 0.5, 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5 or 24-inch or longer lengths) suitable for a selected sensor configuration. For example, a first sensor configured for transcutaneous implantation can employ 2.5-inch lengths, while a second sensor configured for transcutaneous implantation can employ 3-inch lengths. In another example, a first sensor configured for implantation into a peripheral vein of an adult host can employ a 3-inch length, while a second sensor configured for implantation into a central vein of an adult host can employ a 12-inch length. The window is formed on each sensor, such as by scraping and or etching a radial window through the silver-containing material and the insulator such that the platinum surface is exposed (e.g., the electroactive surface of the "working electrode"). In some embodiments, a reel of elongated body is singularized and then the windows are formed. In other embodiments, the windows are formed along the length of the reel of elongated body, and then later singularized. In a further embodiment, additional manufacturing steps are performed prior to singularization. A membrane 108 is applied to the exposed electroactive surface (e.g., the working electrode) defined by the edges of the window, such that the electroactive surface can function as the working electrode of the sensor to generate a signal associated with an analyte (e.g., when the sensor is in contact with a sample of a host). Alternative manufacturing techniques and/or sequences of steps can be used to produce sensors having the configuration shown in FIG. 1C, such as but not limited to masking a portion of the elongated body (or core) prior to application of the insulator and the silver-containing material.

Figure 1F:
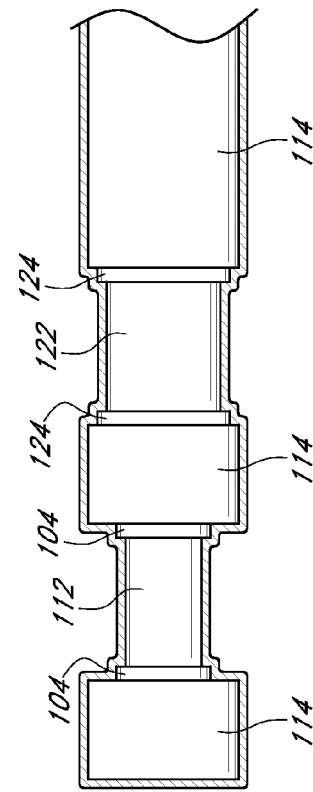
FIG. 1F is a side-view schematic illustrating an in vivo portion of an analyte sensor, in another embodiment.

FIG. 1B is an illustration showing layers cut away, but in the fabrication process the material typically obtained has all layers ending at a tip. A step of removing layers 104 and 114 can be performed so as to form window(s). FIG. 1D illustrates the results of this removal/cutting away process through a side-view/cross-section. The removal process can be accomplished by the methods already described or other methods as known in the art. In one embodiment the removal step is conducted, e.g., by laser skiving, and can be performed in a reel-to-reel process on a continuous strand. The removed area can be stepped, for example, by removing different layers by different lengths (FIG. 1D). In such a fabrication method involving a continuous strand, the sensors can be singularized after the removal step. In some embodiments, if the core is a metal, an end cap may be employed, e.g., by dipping, spraying, shrink tubing, crimp wrapping, etc., an insulating or other isolating material onto the tip. If the core is a polymer (e.g., hydrophobic material), an end cap may not be necessary. For example, in the sensor depicted in FIG. 1D, an end cap 120 (e.g., of a polymer or an insulating material) or other structure may be provided over the core (e.g., if the core 110 is not insulating). FIG. 1E can be considered to build on a general structure as depicted in FIG. 1B, in that two or more additional layers are added to create one or more additional electrodes. Methods for selectively removing two or more windows to create two or more electrodes can also be employed. For example, by adding another conductive layer 122 and insulating layer 124 under a reference electrode layer 114, then two electrodes (first and second working electrodes) can be formed, yielding a dual electrode sensor. The same concept can be applied to create, a counter electrode, electrodes to measure additional analytes (e.g., oxygen), and the like, for example. FIG. 1F illustrates a sensor having an additional electrode 122 (as compared to FIGS. 1B-1D), wherein the windows are selectively removed to expose working electrodes 112, 122 in between a reference electrode (including multiple segments) 114, with a small amount of insulator 104, 124 exposed therebetween. FIG. 1G illustrates another embodiment, wherein selective removal of the various layers is stepped to expose the electrodes 112, 122 and insulators 104, 124 along the length of the elongated body.

In some embodiments, the silver-containing material is applied to the sensor (e.g., the insulated conductive core) in a substantially continuous process, such as described elsewhere herein. Accordingly, in some embodiments, the silver-containing material is applied in a fully-automated process. In other embodiments, the silver-containing material is applied in a semi-automated process.

Referring to FIGS. 2A to 2B, in some embodiments, the sensor can be configured similarly to the continuous analyte sensors disclosed in co-pending U.S. Patent Application Publication No. US-2007-0197889-A1. The sensor includes a distal portion 202, also referred to as the in vivo portion, adapted for implantation into a host, and a proximal portion 204, also referred to as an ex vivo portion, adapted to operably connect to the sensor electronics. In certain embodiments, the sensor includes two or more electrodes: a working electrode (e.g., the electroactive surface of the elongated conductive body 102/first layer 112) and at least one additional electrode (e.g., electroactive surface), which can function as a counter electrode and/or reference electrode, hereinafter referred to as the reference electrode 114. In this embodiment, an insulator 104 is deposited over the conductive core. A radial window 106 is formed through the insulator, such that the working electrode/electroactive surface is exposed. The reference electrode is formed from a silver wire helically wound/wrapped around at least a portion of the sensor. The silver wire can be chloridized either before and/or after application to the sensor. The insulator, which is disposed between the elongated conductive body and reference electrode, provides electrical insulation therebetween. A membrane system may be deposited over the electrodes, such as described in more detail below with reference to FIG. 6.

Although the embodiments of FIGS. 2A to 2B illustrate one electrode configuration including one bulk metal wire helically wound around another bulk metal wire, other electrode configurations are also contemplated. In an alternative embodiment, the working electrode comprises a tube with a reference electrode disposed or coiled inside, including an insulator therebetween. Alternatively, the reference electrode comprises a tube with a working electrode disposed or coiled inside, including an insulator therebetween. In another alternative embodiment, a polymer (e.g., insulating) rod is provided, wherein the electrodes are deposited (e.g., electroplated) thereon. In yet another alternative embodiment, a metallic (e.g., steel) rod is provided, coated with an insulating material, onto which the working and reference electrodes are deposited. In yet another alternative embodiment, one or more working electrodes are helically wound around a reference electrode.

FIG. 3A is a perspective schematic illustrating an alternative embodiment of the analyte sensor, wherein the working electrode body 112 is formed separately from the core 110. FIG. 3B is a cross-sectional view of the sensor of FIG. 3A. In this embodiment, the core is coated with and/or embedded in the insulator 104. A portion of the insulator is removed to provide a window 106 therein. The working electrode body is applied to the core, such that the working electrode body and the core are in electrical contact (e.g., functionally connected). In some embodiments, the working electrode body is formed as a C-clip that is attached over the window. In this embodiment, the interior surface of the C-clip (e.g., working electrode body) makes either direct electrical contact with the exposed surface of the core, such as by the two members touching, or via indirect contact through an intervening media placed/applied on the core and/or the C-clip prior to connection (e.g., an electrically conductive adhesive, gel, paint or other media). In other embodiments, the working electrode body is applied to the exposed surface of the core as a conductive ink, paint or paste, which is subsequently cured and/or dried. For example, in one embodiment, an ink containing platinum particles is printed into the window. In another embodiment, a conductive material, such as a liquid metal, is applied directly to the exposed surface of the core. In another embodiment, no window is formed. Rather, the working electrode body is configured to pierce the insulator and to make physical (e.g., electrical, functional) contact with the core. In some embodiments, such as that shown in FIG. 7, the reference electrode is printed on the elongated body, using methods known in the art. For example, in some embodiments, the reference electrode is a silver-containing ink, paint or paste, such as but not limited to a silver-containing polymer, that is printed on the elongated body using thin-film and/or thick-film printing techniques.

The electrochemical analyte sensors described herein are configured to generate a signal associated with a concentration of the analyte in the host. The sensors provide at least one working electrode and at least one reference electrode. The output signal is typically a raw data stream that is used to provide a useful value of the measured analyte concentration in a host to the patient or doctor, for example. The analyte sensors of certain embodiments may further measure at least one additional signal. For example, in some embodiments, the additional signal is associated with the baseline and/or sensitivity of the analyte sensor, thereby enabling monitoring of baseline and/or sensitivity changes that may occur in a continuous analyte sensor over time. Additionally or alternatively, multiple working electrodes can allow for measurement of multiple analytes, which may also allow for improved accuracy in the measurement of glucose, or allow for detection of certain conditions that can affect sensor accuracy.

In some embodiments, the sensor comprises a second elongated conductive body 102 (or a core that can be electrically connected with a working electrode body). In some embodiments, the second elongated conductive body is configured as a counter electrode. In other embodiments, a sensor comprising a second elongated conductive body (or core) is configured and arranged as a second working electrode, as described below. In some embodiments, the sensor comprises at least three elongated conductive bodies (or cores). The insulating material 104 covers at least a portion of each of the first and second elongated conductive bodies (or cores). In some embodiments, the insulating material covering at least a portion of each of the first and second elongated conductive bodies (or cores) is unitary, such that the insulating material covers at least a portion of both the first and second elongated conductive bodies (or cores). For example, in some embodiments, the elongated conductive bodies (or cores) are disposed (e.g., embedded, located) within the same insulator.

FIG. 3B is a schematic illustrating a cross-section of an analyte sensor in one embodiment, in which an insulated conductive body includes a plurality of conductive cores 110A, 110B, and 110C located (e.g., embedded) in the insulator 104. A surface of core 110B is exposed by window 106, and a working electrode body 112 is applied to the exposed surface of the core. FIG. 3B shows a single working electrode body. However, each core can have a working electrode body attached thereto (e.g., in electrical contact with it). Accordingly, in some embodiments, a completed sensor includes one, two, or three working electrode bodies. Similarly, if the insulated conductive body includes more than three cores, then the completed sensor manufactured from that insulated conductive body can include a corresponding number of elongated conductive bodies.

In the embodiment shown in FIG. 3B, the working electrode body is a formed structure and/or body (e.g., a C-clip, wire or foil) that is attached at the window. In an alternative embodiment, the working electrode body comprises an amorphous material (e.g., an ink, paint or paste) applied to the exposed surface (e.g., through the window) and subsequently cured. In another alternative embodiment, the working electrode body is configured for application over the insulator (e.g., no window is formed) and to extend through (e.g., pierce, intersect) the insulator, such that at least the ends of the working electrode body make electrical contact with the core. In some embodiments, the core and working electrode body make direct physical contact, such that an electrical current can pass therebetween. However, a conductive intermediary, such as a conductive adhesive, gel, lubricant, paint, ink or paste is disposed therebetween, such as to enable current transfer from one component to the other, or to promote attachments between two incompatible materials (e.g., that will not readily adhere to each other). In this embodiment, one, some or all of the inner bodies can be connected and/or attached to a working electrode body, wherein the sensor includes one, two, three, or more working electrodes. In embodiments in which two or more windows are formed in the insulator, the windows are staggered along a length of the sensor (e.g., the in vivo portion). In other embodiments, the windows are not staggered along the length of the sensor. In some embodiments, a silver-containing material is applied over the insulator, to form a reference electrode. In other embodiments, a silver wire is wrapped around the sensor, to form the reference electrode, as described elsewhere herein.

FIG. 4A is a perspective view of the in vivo portion of an analyte sensor in another embodiment. In this embodiment, the insulated elongated body comprises three conductive cores 110A, 110B, 110C located in (e.g., embedded in, coated with) the insulator 104. In this embodiment, a plurality of windows is formed in and/or through the insulator, such that each window exposes a portion of a core. As a non-limiting example, window 106A is formed in the insulator such that a portion of core 110A is exposed. Similarly, window 106B is formed in the insulator such that a portion of core 110B is exposed. The windows can be staggered and/or non-staggered along the longitudinal length of the sensor. In a further embodiment, each conductive core includes an inner core and an outer core, such as described elsewhere herein.

FIG. 4B is a perspective view of the in vivo portion of an analyte sensor including an elongated body (e.g., configured and arranged for multi-axis bending) formed of an insulator 104, first and second conductive cores 110A, 110B embedded in the insulator, and a membrane 108. The first conductive core is formed of platinum, platinum-iridium, gold, palladium, iridium, graphite, carbon, a conductive polymer and/or an alloy, and a first window 106A is configured and arranged to expose an electroactive portion of the first conductive core. The second conductive core is formed of a silver-containing material (e.g., a silver or silver/silver-chloride wire, or a silver-containing wire-shaped a silver-containing material body), and a second window 106B is configured and arranged to expose an electroactive portion of the second conductive core. In some embodiments, instead of a bulk metal wire, the first conductive core comprises an inner core and an outer core. For example, to reduce material costs, the inner core is formed of a material that is relatively less expensive than platinum, such as stainless steel, titanium, tantalum and/or a polymer, and the outer core is formed of a material that provides an appropriate electroactive surface, such as but not limited to platinum, platinum-iridium, gold, palladium, iridium, graphite, carbon, a conductive polymer and/or an alloy. In some embodiments, the membrane covers the exposed electroactive portion of the first conductive core. In a further embodiment, the membrane covers the in vivo portion of the sensor. In some embodiments, a third conductive core is embedded in the insulator. In some embodiments, the third conductive core is configured and arranged as a second working electrode, which can be configured as a redundant working electrode, a non-analyte signal-measuring working electrode (e.g., no enzyme as described below), as a counter working electrode, to detect a second analyte, and/or the like.

FIG. 4C is a perspective view of the in vivo portion of an analyte sensor comprising three insulated conductive bodies, wherein each insulated conductive body includes a core (e.g., 110A, 110B and 110C) coated with insulator (e.g., 104A, 104B and 104C). In some embodiments, one or more of the cores is formed of a material that provides the electroactive surface of the working electrode, such as but not limited to platinum, platinum-iridium, gold, palladium, iridium, graphite, carbon, a conductive polymer and/or an alloy. However, in some embodiments, one or more of the cores is formed of an inner core and an outer core, wherein a portion of the surface of the outer core provides the electroactive surface of the working electrode. In still other embodiments, one or more of the cores is formed of a material that provides electrical conduction from the working electrode (e.g., an attached working electrode body) to sensor electronics. Materials suitable to provide electrical conduction include, but are not limited to stainless steel, titanium, tantalum and/or a conductive polymer. In some embodiments, one or more working electrode bodies 112 are disposed (e.g., applied, attached, located) on the cores, as described elsewhere herein. In some embodiments, the cores (e.g., coated with insulator) are bundled together, such as by an elastic band, an adhesive, wrapping, a shrink-wrap or C-clip, as is known in the art. In other embodiments, the inner bodies (e.g., coated with insulator) are twisted, such as into a triple-helix or similar configuration. In one embodiment, two of the cores (e.g., coated with insulator) are twisted together to form a twisted pair, and then a third core (e.g., with insulator) and/or elongated conductive body is twisted around the twisted pair. In some embodiments, the sensor comprises additional cores (e.g., coated with insulator).

FIG. 5A is a perspective view of the in vivo portion a dual-electrode analyte sensor, in one embodiment. In this embodiment, the sensor comprises first and second bundled elongated bodies (e.g., conductive cores) E1, E2, wherein a working electrode comprises an exposed electroactive surface of the elongated body, and a reference electrode 114, wherein each working electrode comprises a conductive core. For example, the first working electrode comprises an exposed portion of the surface of a first elongated body 102A having an insulating material 104A disposed thereon, such that the portion of the surface of the elongated body (e.g., the working electrode) is exposed via a radial window 106A in the insulator. In some embodiments, the elongated body comprises a core and a first layer, wherein an exposed surface (e.g., electroactive) of the first layer is the first working electrode. The second working electrode comprises an exposed surface of a second core 110B having an insulator 104B disposed thereon, such that a portion of the surface of the core is exposed via a radial window 106B in the insulator. A first layer (not shown) is applied to the exposed surface of the second core to form the second working electrode. In this embodiment, the radial windows are spaced such that the working electrodes (e.g., electroactive surfaces) are substantially overlapping along the length of the sensor. However, in other embodiments, the working electrodes are spaced such that they are not substantially overlapping along the length of the sensor. In this embodiment, the reference electrode comprises a wire (e.g., Ag/AgCl wire) wrapped around the bundled conductive cores. However, in some embodiments, the referenced electrode comprises a layer of silver-containing material applied to at least one of the conductive cores, such as described with reference to FIG. 1B.

FIG. 5B is a perspective view of the in vivo portion of a dual-electrode analyte sensor, in another embodiment. In this embodiment, the first and second elongated bodies E1, E2 are twisted into a twisted pair, such as a helix. The reference electrode 114 is then wrapped around the twisted pair.

FIGS. 5C and 5D include views of the in vivo portion of a dual-electrode analyte sensor, in additional embodiments. In these embodiments, the first and second elongated bodies E1, E2 are bundled together with reference electrode 114. Connectors 502, 530 are configured and arranged to hold the conductive cores and reference electrode together. Alternatively, instead of connectors 502, a tube 530 or heat shrink material can be employed as a connector and/or supporting member. The tubing or heat shrink material may include an adhesive inside the tube so as to provide enhanced adhesion to the components secured within (e.g., wire(s), core, layer materials, etc.). In such a configuration, the heat-shrink material functions not only as an insulator, but also to hold the proximal ends of the sensor together so as to prevent or reduce fatigue and/or to maintain the electrodes together in the event of a fatigue failure. In the embodiment depicted in FIG. 5C, the wires need not be a core and a layer, but can instead comprise bulk materials. The distal ends of the sensor can be loose and finger-like, as depicted in FIG. 5C, or can be held together with an end cap. A reference electrode can be placed on one or more of the first and second elongated bodies instead of being provided as a separate electrode, and the first and second elongated bodies including at least one reference electrode thereof can be bundled together. Heat shrink tubing, crimp wrapping, dipping, or the like can be employed to bundle one or more elongated bodies together. In some embodiments, the reference electrode is a wire, such as described elsewhere herein. In other embodiments, the reference electrode comprises a foil. In an embodiment of a dual-electrode analyte sensor, the first and second elongated bodies can be present as or formed into a twisted pair, which is subsequently bundled with a wire or foil reference electrode. Connectors, which can also function as supporting members, can be configured and arranged to hold the conductive cores and reference electrode together.

In some embodiments, a dual-electrode sensor is configured and arranged to detect two analytes and/or configured as plus-enzyme and minus-enzyme electrodes. In certain embodiments of a dual-electrode analyte sensor, the first working electrode (e.g., the electroactive surface of the first elongated body E1) is configured and arranged to generate a first signal comprising an analyte component and a baseline, and the second working electrode (e.g., the electroactive surface of the second elongated body E2) is configured and arranged to generate a second signal comprising baseline without an analyte component. In one such dual-electrode system, a first electrode functions as a hydrogen peroxide sensor including a membrane system containing glucose-oxidase disposed thereon, which operates as described herein. A second electrode is a hydrogen peroxide sensor that is configured similar to the first electrode, but with a modified membrane system (without active enzyme, for example). This second electrode provides a signal composed mostly of the baseline signal, b.

In some dual-electrode systems, the baseline signal is (electronically or digitally) subtracted from the glucose signal to obtain a glucose signal substantially without baseline. Accordingly, calibration of the resultant difference signal can be performed by solving the equation y=mx with a single paired measurement. Calibration of the inserted sensor in this alternative embodiment can be made less dependent on the values/range of the paired measurements, less sensitive to error in manual blood glucose measurements, and can facilitate the sensor's use as a primary source of glucose information for the user. U.S. Patent Application Publication No. US-2005-0143635-A1, U.S. Patent Application Publication No. US-2007-0027385-A1, U.S. Patent Application Publication No. US-2007-0213611-A1, and U.S. Patent Application Publication No. US-2008-0083617-A1 describe systems and methods for subtracting the baseline from a sensor signal.

In some alternative dual-electrode system embodiments, the analyte sensor is configured to transmit signals obtained from each electrode separately (e.g., without subtraction of the baseline signal). In this way, the receiver can process these signals to determine additional information about the sensor and/or analyte concentration. For example, by comparing the signals from the first and second electrodes, changes in baseline and/or sensitivity can be detected and/or measured and used to update calibration (e.g., without the use of a reference analyte value). In one such example, by monitoring the corresponding first and second signals over time, an amount of signal contributed by baseline can be measured. In another such example, by comparing fluctuations in the correlating signals over time, changes in sensitivity can be detected and/or measured.

In some embodiments, a substantial portion of the in vivo portion of the sensor is designed with at least one dimension less than about 0.004 inches, 0.005 inches, 0.006 inches, 0.008 inches, 0.01 inches, 0.012, 0.015, or 0.02 inches. In some embodiments, in which the sensor is configured and arranged for implantation into a host vessel, a substantial portion of the sensor that is in fluid contact with the blood flow is designed with at least one dimension less than about 0.001, 0.002, 0.003, 0.004, 0.005, 0.006, 0.008, 0.01, 0.012, or 0.015, inches. As one exemplary embodiment, a sensor such as described in more detail with reference to FIGS. 5A to 5E is formed from a 0.004 inch conductive wire (e.g., platinum) for a diameter of about 0.004 inches along a substantial portion of the sensor (e.g., in vivo portion or fluid contact portion). As another exemplary embodiment, a sensor such as described in more detail with reference to FIGS. 5A to 5E is formed from a 0.004 inch conductive wire and vapor deposited with an insulator material for a diameter of about 0.005 inches along a substantial portion of the sensor (e.g., in vivo portion or fluid contact portion), after which a desired electroactive surface area can be exposed. In the above two exemplary embodiments, the reference electrode can be located remote from the working electrode (e.g., formed from the conductive wire). While the devices and methods described herein are suitable for use within the host's blood stream, one skilled in the art will recognize that the systems, configurations, methods and principles of operation described herein can be incorporated into other analyte sensing devices, such as but not limited to transcutaneous devices, subcutaneous devices, and wholly implantable devices such as described in U.S. Patent Application Publication No. US-2006-0016700-A1.

In addition to the embodiments described above, the sensor can be configured with additional working electrodes as described in U.S. Patent Application Publication No. US-2005-0143635-A1, U.S. Pat. No. 7,081,195, and U.S. Patent Application Publication No. US-2007-0027385-A1. For example, in one embodiment have an auxiliary working electrode, wherein the auxiliary working electrode comprises a wire formed from a conductive material, such as described with reference to the glucose-measuring working electrode above. The reference electrode, which can function as a reference electrode alone, or as a dual reference and counter electrode, is formed from silver, silver/silver chloride, and the like.

In some embodiments, the electrodes are juxtapositioned and/or twisted with or around each other; however other configurations are also possible. In one example, the auxiliary working electrode and reference electrode can be helically wound around the glucose-measuring working electrode. Alternatively, the auxiliary working electrode and reference electrode can be formed as a double helix around a length of the glucose-measuring working electrode. The assembly of wires can then be optionally coated together with an insulating material, similar to that described above, in order to provide an insulating attachment. Some portion of the coated assembly structure is then stripped, for example using an excimer laser, chemical etching, and the like, to expose the necessary electroactive surfaces. In some alternative embodiments, additional electrodes can be included within the assembly, for example, a three-electrode system (including separate reference and counter electrodes) as is appreciated by one skilled in the art.

In some alternative embodiments, additional electrodes can be included within the assembly, for example, a three-electrode system (working, reference, and counter electrodes) and/or an additional working electrode (e.g., an electrode which can be used to generate oxygen, which is configured as a baseline subtracting electrode, or which is configured for measuring additional analytes). U.S. Patent Application Publication No. US-2005-0161346-A1, U.S. Patent Application Publication No. US-2005-0143635-A1, and U.S. Patent Application Publication No. US-2007-0027385-A1 describe some systems and methods for implementing and using additional working, counter, and/or reference electrodes. In one implementation wherein the sensor comprises two working electrodes, the two working electrodes are juxtapositioned (e.g., extend parallel to each other), around which the reference electrode is disposed (e.g., helically wound). In some embodiments wherein two or more working electrodes are provided, the working electrodes can be formed in a double-, triple-, quad-, etc. helix configuration along the length of the sensor (for example, surrounding a reference electrode, insulated rod, or other support structure). The resulting electrode system can be configured with an appropriate membrane system, wherein the first working electrode is configured to measure a first signal comprising glucose and baseline (e.g., background noise) signals and the additional working electrode is configured to measure a baseline signal only (e.g., configured to be substantially similar to the first working electrode, but without an enzyme disposed thereon). In this way, the baseline signal can be subtracted from the first signal to produce a glucose-only signal that is substantially not subject to fluctuations in the baseline and/or interfering species on the signal.

In certain embodiments, the analyte sensor is configured as a dual-electrode system and comprises a first working electrode and a second working electrode, in addition to a reference electrode. The first and second working electrodes may be in any useful conformation, as described in U.S. Patent Application Publication No. US-2007-0027385-A1, U.S. Patent Application Publication No. US-2007-0213611-A1, U.S. Patent Application Publication No. US-2007-0027284-A1, U.S. Patent Application Publication No. US-2007-0032717-A1, U.S. Patent Application Publication No. US-2007-0093704-A1, and U.S. Patent Application Publication No. US-2008-0083617-A1. In some embodiments, the first and second working electrodes are twisted and/or bundled. For example, two wire working electrodes can be twisted together, such as in a helix conformation. The reference electrode can then be wrapped around the twisted pair of working electrodes. In some embodiments, the first and second working electrodes include a coaxial configuration. A variety of dual-electrode system configurations are described with reference to FIGS. 2G through 2H of the references incorporated above. In some embodiments, the sensor is configured as a dual electrode sensor, such as described in U.S. Patent Application Publication No. US-2005-0143635-A1, U.S. Patent Application Publication No. US-2007-0027385-A1, U.S. Patent Application Publication No. US-2007-0213611-A1, and U.S. Patent Application Publication No. US-2008-0083617-A1.

In certain embodiments, both of the working electrodes of a dual-electrode analyte sensor are disposed beneath a sensor membrane, such as but not limited to a membrane system similar to that described with reference to FIG. 6, with the following exceptions. The first working electrode is disposed beneath an enzymatic enzyme domain (or portion of the sensor membrane) including an active enzyme configured to detect the analyte or an analyte-related compound. Accordingly, the first working electrode is configured to generate a first signal composed of both a signal related to the analyte and a signal related to non-analyte electroactive compounds (e.g., physiological baseline, interferents, and non-constant noise) that have an oxidation/reduction potential that overlaps with the oxidation/reduction potential of the analyte. This oxidation/reduction potential may be referred to as a "first oxidation/reduction potential" herein. The second working electrode is disposed beneath a non-enzymatic enzyme domain (or portion of the sensor membrane) that includes either an inactivated form of the enzyme contained in the enzymatic portion of the membrane or no enzyme. In some embodiments, the non-enzymatic portion can include a non-specific protein, such as BSA, ovalbumin, milk protein, certain polypeptides, and the like. The non-enzymatic portion generates a second signal associated with noise of the analyte sensor. The noise of the sensor comprises signal contribution due to non-analyte electroactive species (e.g., interferents) that have an oxidation/reduction potential that substantially overlaps the first oxidation/reduction potential (e.g., that overlap with the oxidation/reduction potential of the analyte). In some embodiments of a dual-electrode analyte sensor configured for fluid communication with a host's circulatory system, the non-analyte related electroactive species comprises at least one species selected from the group consisting of interfering species, non-reaction-related hydrogen peroxide, and other electroactive species.

In one exemplary embodiment, the dual-electrode analyte sensor is a glucose sensor having a first working electrode configured to generate a first signal associated with both glucose and non-glucose related electroactive compounds that have a first oxidation/reduction potential. Non-glucose related electroactive compounds can be any compound, in the sensor's local environment that has an oxidation/reduction potential substantially overlapping with the oxidation/reduction potential of $H_2O_2$, for example. While not wishing to be bound by theory, it is believed that the glucose-measuring electrode can measure both the signal directly related to the reaction of glucose with GOx (produces $H_2O_2$ that is oxidized at the working electrode) and signals from unknown compounds that are in the blood surrounding the sensor. These unknown compounds can be constant or non-constant (e.g., intermittent or transient) in concentration and/or effect. In some circumstances, it is believed that some of these unknown compounds are related to the host's disease state. For example, it is known that blood chemistry changes dramatically during/after a heart attack (e.g., pH changes, changes in the concentration of various blood components/protein, and the like). Additionally, a variety of medicaments or infusion fluid components (e.g., acetaminophen, ascorbic acid, dopamine, ibuprofen, salicylic acid, tolbutamide, tetracycline, creatinine, uric acid, ephedrine, L-dopa, methyl dopa and tolazamide) that may be given to the host may have oxidation/reduction potentials that overlap with that of $H_2O_2$.

In this exemplary embodiment, the dual-electrode analyte sensor includes a second working electrode that is configured to generate a second signal associated with the non-glucose related electroactive compounds that have the same oxidation/reduction potential as the above-described first working electrode. In some embodiments, the non-glucose related electroactive species includes at least one of interfering species, non-reaction-related $H_2O_2$, and other electroactive species. For example, interfering species includes any compound that is not directly related to the electrochemical signal generated by the glucose-GOx reaction, such as but not limited to electroactive species in the local environment produces by other body processes (e.g., cellular metabolism, a disease process, and the like). Other electroactive species includes any compound that has an oxidation/reduction potential similar to or overlapping that of $H_2O_2$.

The non-analyte (e.g., non-glucose) signal produced by compounds other than the analyte (e.g., glucose) may obscure the signal related to the analyte, may contribute to sensor inaccuracy, and is considered background noise. Background noise includes both constant and non-constant components and is to be removed to accurately calculate the analyte concentration. While not wishing to be bound by theory, it is believed that the sensor of some of the embodiments are designed (e.g., with symmetry, coaxial design and/or integral formation, and interference domain of the membrane described elsewhere herein) such that the first and second electrodes are influenced by substantially the same external and/or environmental factors, which enables substantially equivalent measurement of both the constant and non-constant species/noise. This advantageously allows the substantial elimination of noise on the sensor signal (using electronics described elsewhere herein) to substantially reduce or eliminate signal effects due to noise, including non-constant noise (e.g., unpredictable biological, biochemical species, medicaments, pH fluctuations, $O_2$ fluctuations, or the like) known to effect the accuracy of conventional continuous sensor signals. The sensor includes electronics may be operably connected to the first and second working electrodes. The electronics are configured to provide the first and second signals that are used to generate glucose concentration data substantially without signal contribution due to non-glucose-related noise. The electronics can include at least a potentiostat that provides a bias to the electrodes. In some embodiments, sensor electronics are configured to measure the current (or voltage) to provide the first and second signals. The first and second signals are used to determine the glucose concentration substantially without signal contribution due to non-glucose-related noise such as by but not limited to subtraction of the second signal from the first signal or alternative data analysis techniques. In some embodiments, the sensor electronics include a transmitter that transmits the first and second signals to a receiver, where additional data analysis and/or calibration of glucose concentration can be processed. U.S. Patent Application Publication No. US-2005-0027463-A1, U.S. Patent Application Publication No. US-2005-0203360-A1, and U.S. Patent Application Publication No. US-2006-0036142-A1 describe systems and methods for processing sensor analyte data.

In some embodiments, the dual-electrode sensor is configured such that the first and second working electrodes are equivalently influenced by in vivo environmental factors. For example, in one embodiment, the dual-electrode sensor is configured for fluid communication with the circulatory system of the host, such as by implantation in the host's vein or artery via a vascular access device (also referred to as a fluid communication device herein) such as a catheter and/or cannula. When the sensor is contacted with a sample of the host's circulatory system (e.g., blood), the first and second working electrodes are configured such that they are equivalently influenced by a variety of environmental factors impinging upon the sensor, such as but not limited to non-analyte related electroactive species (e.g., interfering species, non-reaction-related $H_2O_2$, another electroactive species). Because the first and second working electrodes are equivalently influenced by in vivo environmental factors, the signal component associated with the in vivo environmental factors (e.g., non-analyte related species with an oxidation/reduction potential that overlaps with that of the analyte) can be removed from the signal detected by the first working electrode (e.g., the first signal). This can give a substantially analyte-only signal.

In some embodiments, the surface area of the electroactive portion of the reference (and/or counter) electrode is at least six times the surface area of the working electrodes. In other embodiments, the reference (and/or counter) electrode surface is at least 1, 2, 3, 4, 5, 7, 8, 9 or 10 times the surface area of the working electrodes. In other embodiments, the reference (and/or counter) electrode surface area is at least 11, 12, 13, 14, 15, 16, 17, 18, 19 or 20 times the surface area of the working electrodes. For example, in a needle-type glucose sensor, similar to the embodiment shown in FIGS. 5A-5E, the surface area of the reference electrode (e.g., 114) includes the exposed surface of the reference electrode, such as but not limited to the electrode surface facing away from the working electrodes.

As a non-limiting example, in one embodiment, the dual-electrode analyte sensor comprises a first working electrode configured to detect the analyte and a second working electrode, wherein the first and second working electrodes are located on of two wire elongated conductive bodies E1, E2 twisted together to form a "twisted pair." The first working electrode is disposed beneath an enzymatic portion of the membrane (not shown) containing an analyte-detecting enzyme. For example, in a glucose-detecting dual-electrode analyte sensor, a glucose-detecting enzyme, such as GOX, is included in the enzymatic portion of the membrane. Accordingly, the first working electrode detects signal due to both the analyte and non-analyte-related species that have an oxidation/reduction potential that substantially overlaps with the oxidation/reduction potential of the analyte. The second working electrode is disposed beneath a portion of the membrane comprising either inactivated enzyme (e.g., inactivated by heat, chemical or UV treatment) or no enzyme. Accordingly, the second working electrode detects a signal associated with only the non-analyte electroactive species that have an oxidation/reduction potential that substantially overlaps with that of analyte. For example, in the glucose-detecting dual-electrode analyte sensor described above, the non-analyte (e.g., non-glucose) electroactive species have an oxidation/reduction potential that overlaps substantially with that of $H_2O_2$. A reference electrode 114, such as a silver/silver chloride wire electrode, is wrapped around the twisted pair. The three electrodes (e.g., working electrodes E1, E2 and the reference electrode 114) are connected to sensor electronics (not shown), such as described elsewhere herein. In certain embodiments, the dual-electrode sensor is configured to provide an analyte-only signal (e.g., glucose-only signal) substantially without a signal component due to the non-analyte electroactive species (e.g., noise). For example, the dual-electrode sensor is operably connected to sensor electronics that process the first and second signals, such that a substantially analyte-only signal is provided (e.g., output to a user). In other exemplary embodiments, the dual-electrode sensor can be configured for detection of a variety of analytes other than glucose, such as but not limited to urea, creatinine, succinate, glutamine, oxygen, electrolytes, cholesterol, lipids, triglycerides, hormones, liver enzymes, and the like.

In some embodiments, the analyte sensor substantially continuously measures the host's analyte concentration. In some embodiments, for example, the sensor can measure the analyte concentration every fraction of a second, about every fraction of a minute or every minute. In other exemplary embodiments, the sensor measures the analyte concentration at least about every 2, 3, 4, 5, 6, 7, 8, 9, or 10 minutes. In still other embodiments, the sensor measures the analyte concentration every fraction of an hour, such as but not limited to every 15, 30 or 45 minutes. Yet in other embodiments, the sensor measures the analyte concentration about every hour or longer. In some exemplary embodiments, the sensor measures the analyte concentration intermittently or periodically. In one embodiment, the analyte sensor is a glucose sensor and measures the host's glucose concentration about every 4-6 minutes. In a further embodiment, the sensor measures the host's glucose concentration every 5 minutes.

As a non-limiting example, dual-electrode glucose sensor can be manufactured as follows. In one embodiment, the conductive cores are first coated with a layer of insulating material (e.g., non-conductive material or dielectric) to prevent direct contact between conductive cores and the reference electrode 114. At this point, or at any point hereafter, the two insulated conductive cores can be twisted and/or bundled to form a twisted pair. A portion of the insulator on an exterior surface of each conductive core is etched away, to expose the electroactive surfaces of the working electrodes. In some embodiments, an enzyme solution (e.g., containing active GOx) is applied to the electroactive surfaces of both working electrodes, and dried. Thereafter, the enzyme applied to one of the electroactive surfaces is inactivated. As is known in the art, enzymes can be inactivated by a variety of means, such as by heat, treatment with inactivating (e.g., denaturing) solvents, proteolysis, laser irradiation or UV irradiation (e.g., at 254-320 nm). For example, the enzyme coating one of the electroactive surfaces can be inactivated by masking one of the electroactive surfaces/electrodes (e.g., temporarily covered with a UV-blocking material); irradiating the sensor with UV light (e.g., 254-320 nm; a wavelength that inactivates the enzyme, such as by cross-linking amino acid residues) and removing the mask. Accordingly, the GOx on the second working electrode is inactivated by the UV treatment, but the first working electrode's GOx is still active due to the protective mask. In other embodiments, an enzyme solution containing active enzyme is applied to a first electroactive surface (e.g., first working electrode) and an enzyme solution containing either inactivated enzyme or no enzyme is applied to the second electroactive surface (e.g., second working electrode). Thus, the enzyme-coated first electroactive surface detects analyte-related signal and non-analyte-related signal, while the second electroactive surface, which lacks active enzyme, detects non-analyte-related signal. As described herein, the sensor electronics can use the data collected from the two working electrodes to calculate the analyte-only signal.

In some embodiments, the dual-electrode sensor system is configured for fluid communication with a host's circulatory system, such as via a vascular access device. A variety of vascular access devices suitable for use with a dual-electrode analyte sensor are described U.S. Patent Application Publication No. US-2008-0119703-A1, U.S. Patent Application Publication No. US-2008-0108942-A1, U.S. Patent Application Publication No. US-2008-0200789-A1.

Figure 8A:
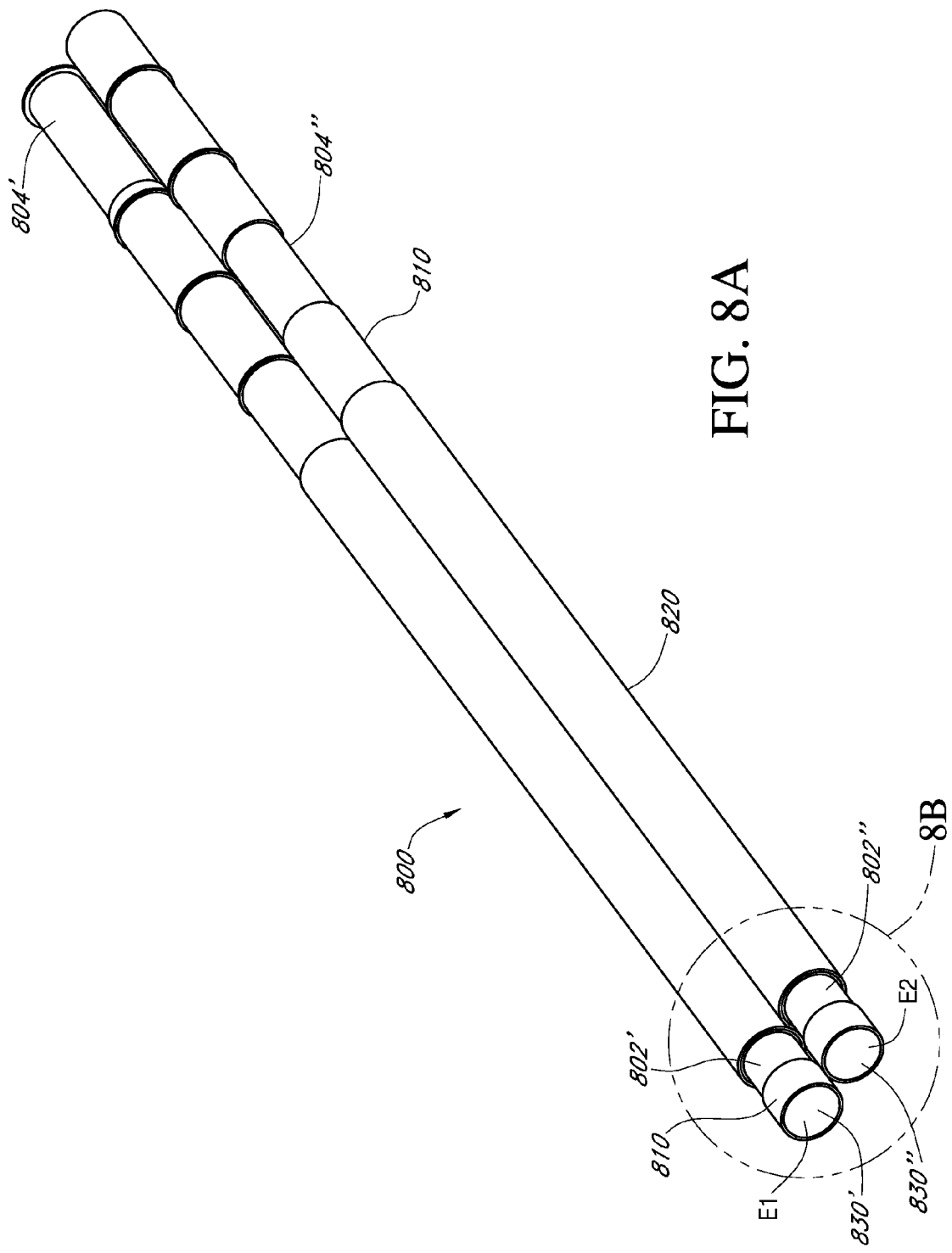
FIG. 8A is a perspective-view schematic illustrating an in vivo portion of a multi-electrode analyte sensor, in another embodiment.
Figure 8C:
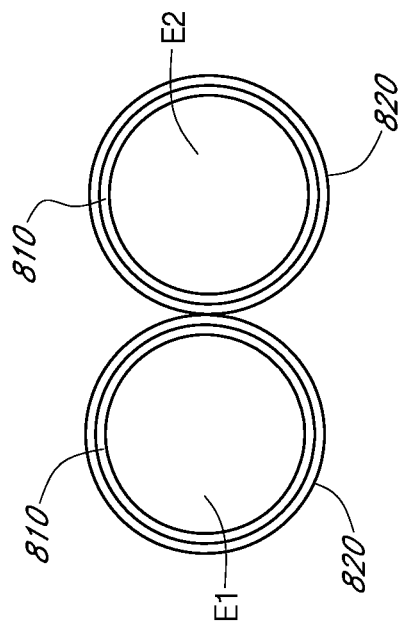
FIG. 8C is a front view of the sensor embodiment illustrated in FIGS. 8A and 8B.
Figure 8B:
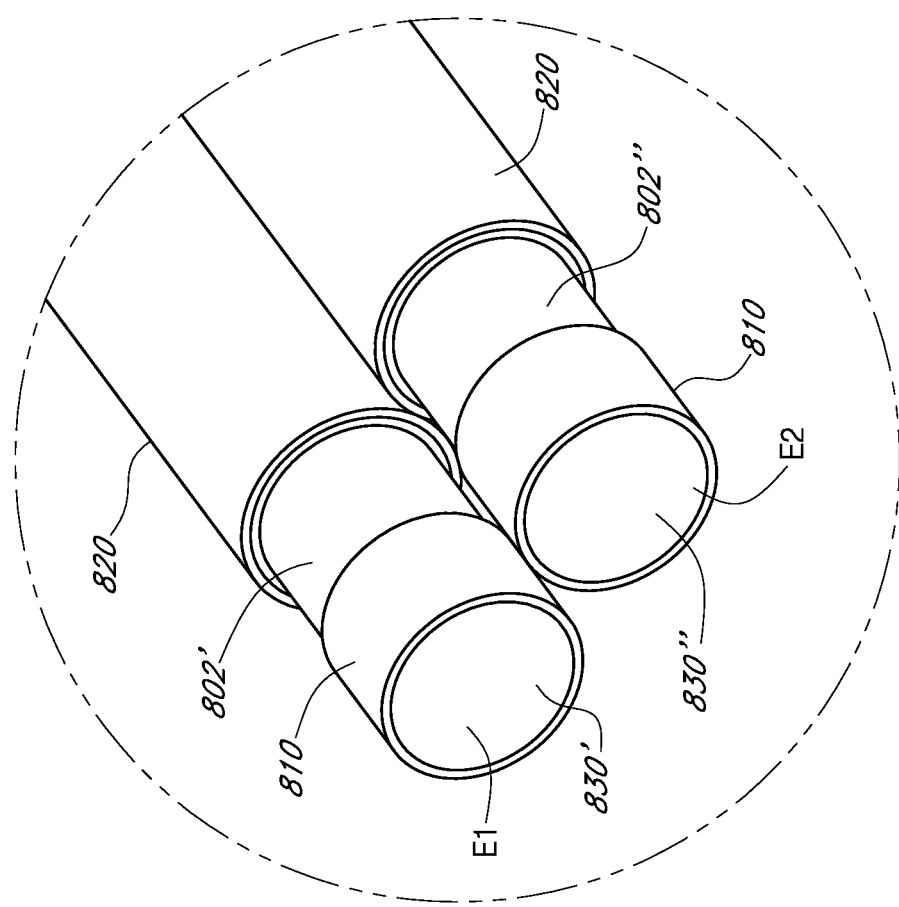
FIG. 8B is a close perspective schematic of the distal portion of the sensor embodiment illustrated in FIG. 8A.

FIG. 8A is a perspective view of the in vivo portion of another embodiment of a multi-electrode sensor system 800 comprising two working electrodes and at least one reference/counter electrode. The sensor system 800 comprises first and second elongated bodies E1, E2, each formed of a conductive core or of a core with a conductive layer deposited thereon. In this particular embodiment, an insulating layer 810, a conductive layer 820, and a membrane layer (not shown) are deposited on top of the elongated bodies E1, E2. The insulating layer 810 separates the conductive layer 820 from the elongated body. The materials selected to form the insulating layer 810 may include any of the insulating materials described elsewhere herein, including polyurethane and polyimide. The materials selected to form the conductive layer 820 may include any of the conductive materials described elsewhere herein, including silver/silver chloride, platinum, gold, etc. Working electrodes 802', 802" are formed by removing portions of the conductive layer 820 and the insulating layer 810, thereby exposing electroactive surface of the elongated bodies E1, E2, respectively. FIG. 8B provides a close perspective view of the distal portion of the elongated bodies E1, E2. FIG. 8C provides a front view of the sensor embodiment illustrated in FIGS. 8A and 8B.

The two elongated bodies illustrated in FIG. 8A are fabricated to have substantially the same shape and dimensions. In some embodiments, the working electrodes are fabricated to have the same properties, thereby providing a sensor system capable of providing redundancy of signal measurements. In other embodiments, the working electrodes, associated with the elongated bodies E1, E2, may each have one or more characteristics that distinguish each working electrode from the other. For example, in one embodiment, each of the elongated bodies E1, E2 may be covered with a different membrane, so that each working electrode has a different membrane property than the other working electrode. For example, one of the working electrodes may have a membrane comprising an enzyme layer and the other working electrode may have a membrane comprising a layer having either an inactivated form of the enzyme or no enzyme. Additional sensor system configurations that are possible with a plurality of working electrodes (e.g., sensor elements) are described in U.S. Provisional Application No. 61/222,716 filed Jul. 2, 2009 and U.S. patent application Ser. No. 12/829,264, filed Jul. 1, 2010, entitled "ANALYTE SENSOR," each of which is incorporated by reference herein in its entirety.

Although not shown in FIGS. 8A-8C, in certain embodiments, the distal ends 830', 830" of the core portions of the elongated bodies E1, E2 may be covered with an insulating material (e.g., polyurethane or polyimide). In alternative embodiments, the exposed core portions 830', 830" may be covered with a membrane system and serve as additional working electrode surface area.

Regarding fabrication of the sensor system illustrated in FIG. 8A-8C, in one embodiment, two elongated bodies E1, E2 are provided. As described above, the elongated bodies E1, E2 may be formed as an elongated conductive core, or alternatively as a core (conductive or non-conductive) having at least one conductive material deposited thereon. Next, an insulating layer 810 is deposited onto each of the elongated bodies E1, E2. Thereafter, a conductive layer 820 is deposited over the insulating layer 810. The conductive layer 820 may serve as a reference/counter electrode and may be formed of silver/silver chloride, or any other material that may be used for a reference electrode. In alternative embodiments, the conductive layer 820 may be formed of a different conductive material, and may be used another working electrode. After these steps, a layer removal process is performed to remove portions of the deposited layers (i.e., the conductive layer 820 and/or the insulating layer 810). Any of the techniques described elsewhere herein (e.g., laser ablation, chemical etching, grit blasting) may be used. In the embodiment illustrated in FIGS. 8A and 8B, layers of the conductive layer 820 and the insulating layer 810 are removed to form the working electrodes 802', 802". Although in the embodiment shown, layer removal is performed across the entire cross-sectional perimeter (e.g., circumference) of the deposited layer, it is contemplated that in other embodiments, layer removal may be performed across a preselected section of the cross-sectional perimeter, instead of across the entire cross-sectional perimeter.

Contacts 804', 804" used to provide electrical connection between the working electrodes and other components of the sensor system may be formed in a similar manner. As shown, contacts 804' and 804" are separated from each other to prevent an electrical connection therebetween. Because the layer removal process is performed on each individual elongated body E1, E2, instead of a single geometrically complicated elongated body, this particular sensor design (i.e., two elongated bodies placed side by side) may provide ease of manufacturing, as compared to the manufacturing processes involved with other multi-electrode systems having other geometries.

After the conductive and insulating layers are deposited onto the elongated body, and after selected portions of the deposited layers have been removed, a membrane is applied onto at least a portion of the elongated bodies. In certain embodiments, the membrane system is applied only to the working electrodes, but in other embodiments the membrane system is applied to the entire elongated body. In one embodiment, the membrane system is deposited onto the two working electrodes simultaneously while they are placed together (e.g., by bundling), but in another embodiment, membranes are deposited onto each individual working electrode first, and the two working electrodes are then placed together.

Figure 9A:
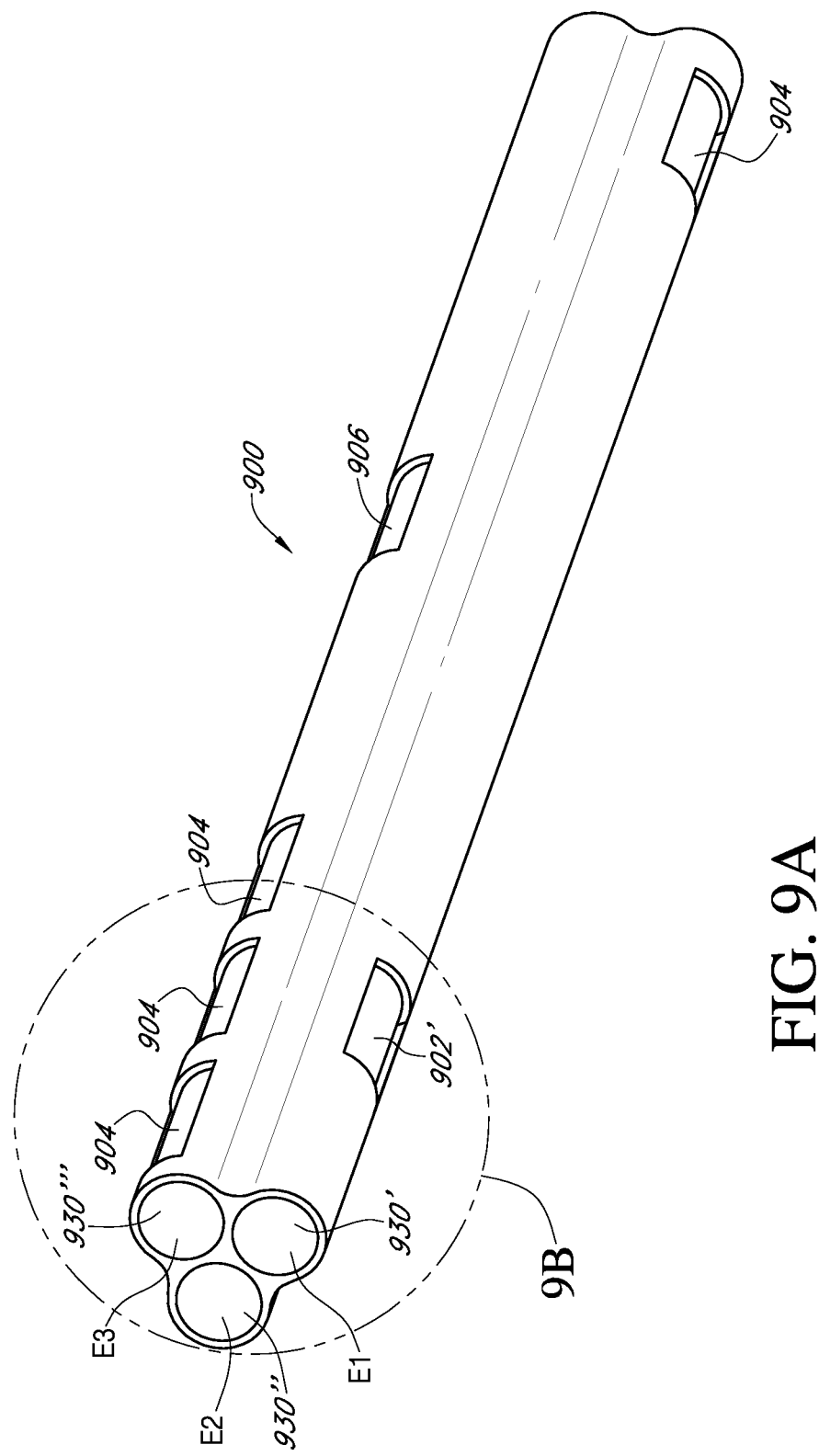
FIG. 9A is a perspective-view schematic illustrating an in vivo portion of a multi-electrode analyte sensor, in another embodiment.

FIG. 9A is a perspective view of the in vivo portion of another embodiment of a multi-electrode sensor system 900 comprising two working electrodes and one reference/counter electrode. The three electrodes are integrated into one piece. The sensor system 900 comprises first, second, and third elongated bodies E1, E2, E3, each formed of a conductive core or of a core with a conductive layer deposited thereon. In this particular embodiment, an insulating domain 910 and a membrane layer (not shown) are deposited on top of an assembly comprising the elongated bodies E1, E2, E3. The insulating domain 910 binds the three elongated bodies E1, E2, E3 in close proximity of each other, while also separating them from direct contact with each other. The materials selected to form the insulating domain 910 may include any of the insulating materials described elsewhere herein, including polyurethane and polyimide, for example. Working electrode 902' on elongated body E1 and another working electrode (not shown) on elongated body E2, are formed by removing portions of the insulating domain 910, thereby exposing electroactive surface of the elongated bodies E1, E2. Similarly, the reference electrode 904' on elongated body E3 is also formed by removing portions of the insulating domain 910, thereby exposing electroactive surface of the elongated body E3. FIG. 9B provides a close perspective view of the distal portion of the elongated bodies E1, E2, E3. FIG. 9C provides a front view of the sensor embodiment illustrated in FIGS. 9A and 9B.

As described elsewhere herein, in certain embodiments, the working electrodes, associated with the elongated bodies E1, E2, may each have one or more characteristics that distinguish each working electrode from the other. For example, in some embodiments, one of the working electrodes may have a membrane comprising an enzyme layer and the other working electrode may have a membrane comprising a layer having either an inactivated form of the enzyme or no enzyme. Additional sensor system configurations that are possible with a plurality of working electrodes (e.g., sensor elements) are described in U.S. Provisional Application No. 61/222,716 filed Jul. 2, 2009 and U.S. patent application Ser. No. 12/829,264, filed Jul. 1, 2010 and entitled "ANALYTE SENSOR," each of which is incorporated by reference herein in its entirety. In other embodiments, the working electrodes are fabricated to have the same properties, thereby providing a sensor system capable of providing redundancy of signal measurements.

Although not shown in FIGS. 9A-9C, in certain embodiments, the distal ends 930', 930", 930''' of the core portions of the elongated bodies E1, E2, E3, respectively, may be covered with an insulating material (e.g., polyurethane or polyimide). In alternative embodiments, one or more of the exposed core portions 930', 930", 930''' may be covered with a membrane system and serve as additional working electrodes.

In one embodiment, fabrication of the sensor system illustrated in FIGS. 9A-9C involves providing three elongated bodies E1, E2, E3. As described above, the elongated bodies may be formed as an elongated conductive core, or alternatively as a core (conductive or non-conductive) having at least one conductive material deposited thereon. The E3 reference electrode includes a core and/or an outer layer that comprises a reference electrode material, such as, silver/silver chloride, for example. Next, an insulating layer is deposited onto each of the elongated bodies. Thereafter, the three elongated bodies E1, E2, E3 (with an insulating layer thereon) are placed together to form a single elongated body. Although not required, in some embodiments, the three elongated bodies E1, E2, E3 may be coated with a thermoplastic material and fed through an aligning die. Afterwards, an insulating domain 910 is deposited over this single elongated body. The deposited domain is then allowed to dry or be cured, after which an unitary elongated body is formed, in which the three elongated bodies E1, E2, E3 are encased and held together by insulating domain 910.

After these steps, a layer removal process is performed to remove portions of the insulating domain 910. Any of the techniques described herein (e.g., laser ablation, chemical etching, grit blasting) may be used. In the embodiment illustrated in FIGS. 9A and 9B, portions of the insulating domain 910 are removed to form the working electrode 902' on elongated body E1, to form a second working electrode (not shown) on elongated body E2, and to form a reference electrode 904 on elongated body E3. Contacts 904', 906 used to provide electrical connection between the working and reference electrodes and other components of the sensor system may be formed in a similar manner.

Figure 10C:
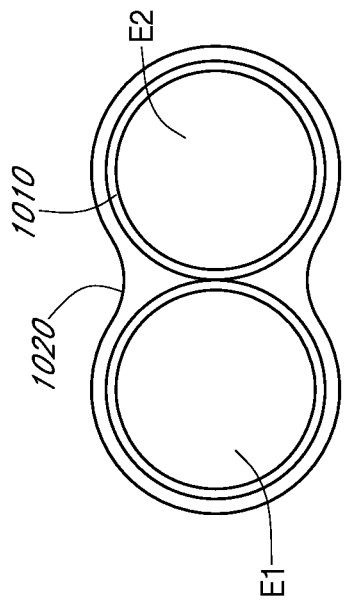
FIG. 10C is a front view of the sensor embodiment illustrated in FIGS. 10A and 10B.
Figure 10B:
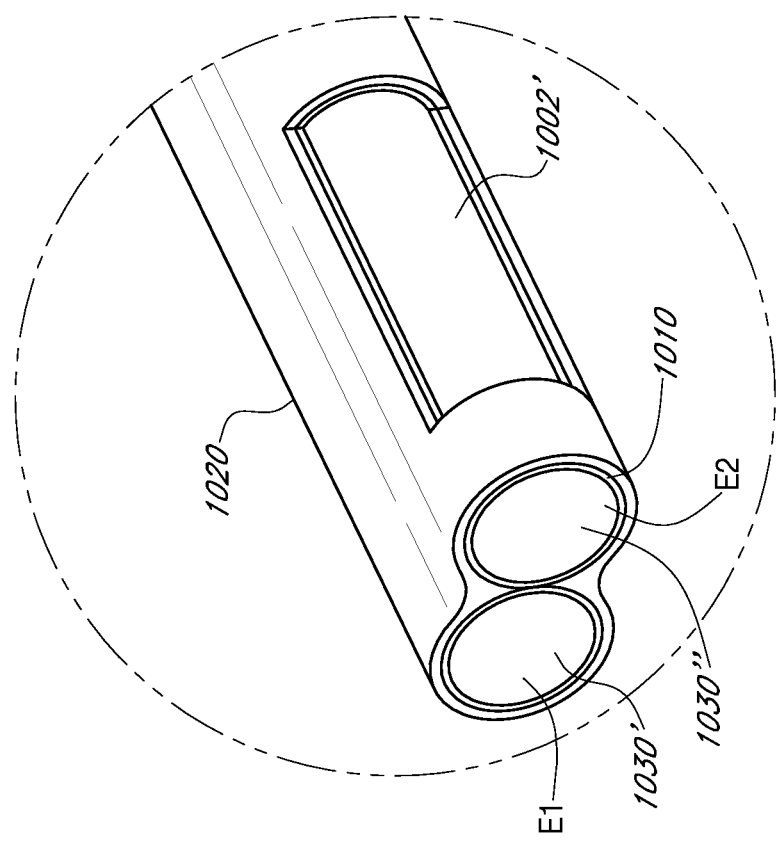
FIG. 10B is a close perspective schematic of the distal portion of the sensor embodiment illustrated in FIG. 10A.

FIG. 10A is a perspective view of the in vivo portion of yet another embodiment of a multi-electrode sensor system 1000 comprising two working electrodes and at least one reference/counter electrode. The sensor system 1000 comprises first and second elongated bodies E1, E2, each formed of a conductive core or of a core with a conductive layer deposited thereon. An insulating layer 1010 is deposited onto each elongated body E1, E2. Furthermore, a conductive domain 1020 and a membrane layer (not shown) are deposited on top of an assembly comprising the elongated bodies E1, E2 and the insulating layer. The conductive domain 1020, binds the two elongated bodies E1, E2 into one elongated body. The insulating layers 1010 surrounding each elongated body E1, E2 prevents electrical contact between the two elongated bodies E1, E2. The materials selected to form the insulating layer 1010 may include any of the insulating materials described elsewhere herein, including polyurethane and polyimide, for example. The materials selected to form the conductive domain 1020 may include any of the conductive materials described elsewhere herein, including silver/silver chloride and platinum, for example. Working electrode 1002' on elongated body E1 and another working electrode (not shown) on elongated body E2, are formed by removing portions of the conductive domain 1020 and portions of the insulating layer 1010, thereby exposing electroactive surfaces of elongated bodies E1, E2. The portion of the conductive domain 1020 not removed forms the reference/counter electrode. FIG. 10B provides a close perspective view of the distal portion of the elongated bodies E1, E2. FIG. 10C provides a front view of the sensor embodiment illustrated in FIGS. 10A and 10B.

As described elsewhere herein, in certain embodiments, the working electrodes, associated with the elongated bodies E1, E2, may each have one or more characteristics that distinguish each working electrode from the other. For example, in some embodiments, one of the working electrodes may have a membrane comprising an enzyme layer and the other working electrode may have a membrane comprising a layer having either an inactivated form of the enzyme or no enzyme. Additional sensor system configurations that are possible with a plurality of working electrodes (e.g., sensor elements) are described in U.S. Provisional Application No. 61/222,716 filed Jul. 2, 2009 and U.S. patent application Ser. No. 12/829,264, filed Jul. 1, 2010 and entitled "ANALYTE SENSOR," each of which is incorporated by reference herein in its entirety. In other embodiments, the working electrodes are fabricated to have the same properties, thereby providing a sensor system capable of providing redundancy of signal measurements.

Although not shown in FIGS. 10A-10C, in certain embodiments, the distal ends 1030', 1030" of the core portions of the elongated bodies E1, E2, respectively, may be covered with an insulating material (e.g., polyurethane or polyimide). In alternative embodiments, one or more of the exposed core portions 1030', 1030" may be covered with a membrane system and serve as additional working electrodes.

In one embodiment, fabrication of the sensor system illustrated in FIGS. 10A-10C involves providing two elongated bodies E1, E2. As described above, the elongated bodies may be formed as an elongated conductive core, or alternatively as a core (conductive or non-conductive) having at least one conductive material deposited thereon. Next, an insulating layer is deposited onto each of the elongated bodies. Thereafter, the two elongated bodies E1, E2 (with an insulating layer thereon) are placed together to form a single elongated body. Although not required, in some embodiments, the three elongated bodies E1, E2, E3 may be coated with a thermoplastic material and fed through an aligning die. Afterwards, a conductive domain 1020 is deposited over this single elongated body. The coated domain is then allowed to dry or be cured, after which the one unitary elongated body is formed, in which the two elongated bodies E1, E2 are encased and held together by conductive domain 1020.

After these steps, a layer removal process is performed to remove portions of the conductive domain 1020 and portions of the insulating layer 1010. Any of the techniques described herein (e.g., laser ablation, chemical etching, grit blasting) may be used. In the embodiment illustrated in FIGS. 10A and 10B, portions of the conductive domain 1020 and insulating layer 1010 are removed to form the working electrode 1002' on elongated body E1, to form a second working electrode (not shown) on elongated body E2, and to form the reference electrode 1020. Contacts 1004', 1004" used to provide electrical connection between the working electrodes and other components of the sensor system may be formed in a similar manner.

With this particular sensor design, because the conductive domain 1020 is disposed between the contact point between the two elongated bodies E1, E2, the sensor system's largest cross-sectional dimension is minimized, as compared to a design in which both of the elongated bodies were each individually covered with a conductive layer.

Figure 11A:
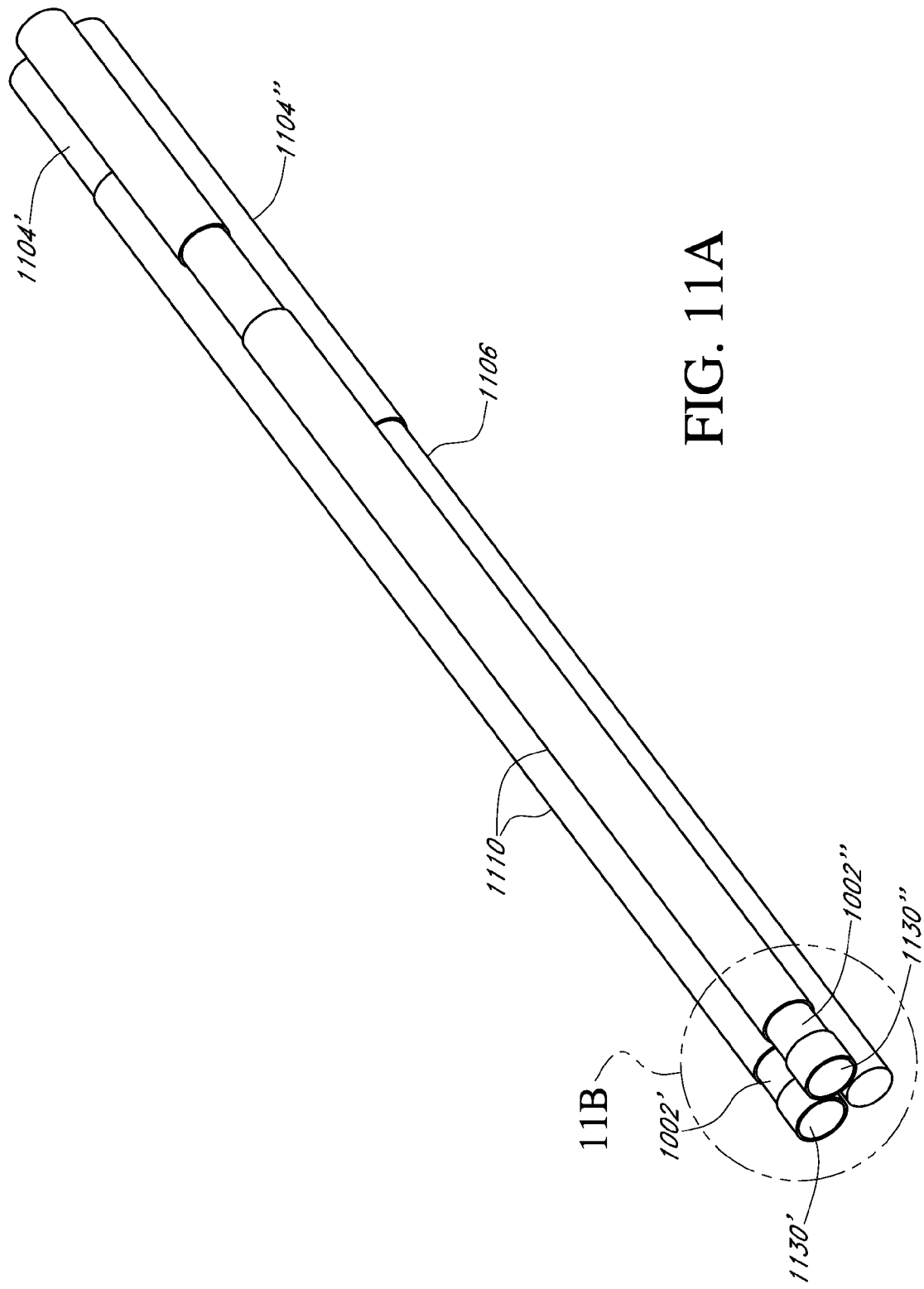
FIG. 11A is a perspective-view schematic illustrating an in vivo portion of a multi-electrode analyte sensor, in another embodiment.

FIG. 11A is a perspective view of the in vivo portion of another embodiment of a multi-electrode sensor system 1100 comprising two working electrodes and one reference/counter electrode. The sensor system 1100 comprises first, second, and third elongated bodies E1, E2, E3, each formed of a conductive core or of a core with a conductive layer deposited thereon. In this particular embodiment, an insulating layer 1110 and a membrane layer (not shown) are deposited on top of the elongated bodies E1, E2. The insulating layer 1110 separates the elongated bodies from each other. The materials selected to form the insulating layer 1110 may include any of the insulating materials described elsewhere herein, including polyurethane and polyimide. Working electrodes 1002', 1002" are formed by removing portions of the insulating layer 1110, thereby exposing electroactive surface of the elongated bodies E1, E2, respectively.

As described elsewhere herein, in certain embodiments, the working electrodes, associated with the elongated bodies E1, E2, may each have one or more characteristics that distinguish each working electrode from the other. For example, in some embodiments, one of the working electrodes may have a membrane comprising an enzyme layer and the other working electrode may have a membrane comprising a layer having either an inactivated form of the enzyme or no enzyme. Additional sensor system configurations that are possible with a plurality of working electrodes (e.g., sensor elements) are described in U.S. Provisional Application No. 61/222,716 filed Jul. 2, 2009 and U.S. patent application Ser. No. 12/829,264, filed Jul. 1, 2010 and entitled "ANALYTE SENSOR," each of which is incorporated by reference herein in its entirety. In other embodiments, the working electrodes are fabricated to have the same properties, thereby providing a sensor system capable of providing redundancy of signal measurements.

Figure 11C:
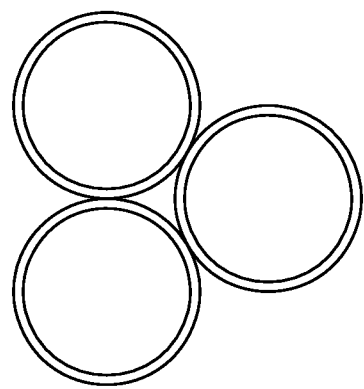
FIG. 11C is a front view of the sensor embodiment illustrated in FIGS. 11A and 11B.
Figure 11B:
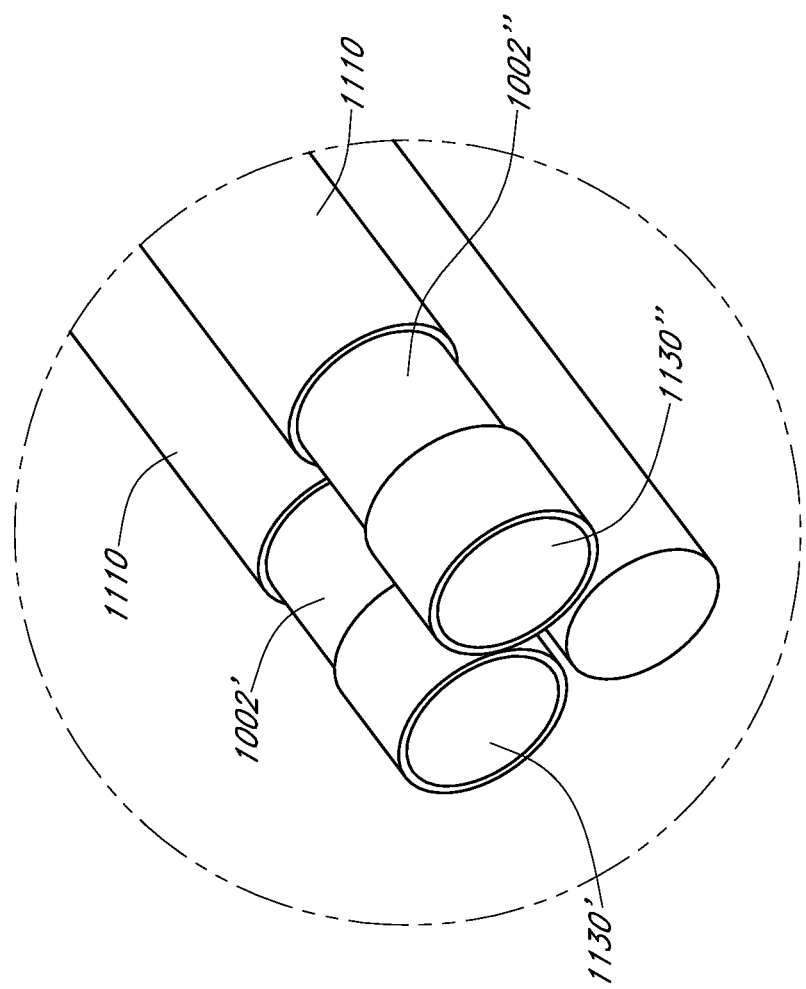
FIG. 11B is a close perspective schematic of the distal portion of the sensor embodiment illustrated in FIG. 11A.

Although not shown in FIGS. 11A-11C, in certain embodiments, the distal ends 1130', 1130" of the core portions of the elongated bodies E1, E2 may be covered with an insulating material (e.g., polyurethane or polyimide). In alternative embodiments, the exposed core portions 1130', 1130" may be covered with a membrane system and serve as additional working electrodes.

Regarding fabrication of the sensor system illustrated in FIG. 11A-11C, in one embodiment, three elongated bodies E1, E2, E3 are provided. As described above, the elongated bodies may be formed as an elongated conductive core, or alternatively as a core (conductive or non-conductive) having at least one conductive material deposited thereon. The elongated bodies E1, E2 that correspond to working electrodes may comprise an elongated core with a conductive material typically used with working electrodes (e.g., a core formed of a conductive material like platinum, or a core plated, coated, or cladded with a conductive material like platinum). The elongated body E3 that corresponds to a reference electrode may comprise an elongated core with a conductive material typically used with reference electrodes (e.g., a core formed of a conductive material like silver/silver chloride, or a core plated, coated, or cladded with a conductive material like silver/silver chloride).

Next, an insulating layer 1110 is deposited onto each of the elongated bodies. In some embodiments, the insulating layer 1110 is formed of a thermoplastic material, thereby allowing the three elongated bodies E1, E2, E3 to be attached together by a heating process that permits the insulating layers of the three elongated bodies E1, E2, E3 to adhere together.

Thereafter, a layer removal process is performed to remove portions of the insulating layer 1110. Any of the techniques described herein (e.g., laser ablation, chemical etching, grit blasting) may be used. In the embodiment illustrated in FIGS. 11A and 11B, the insulating layer 1110 is removed to form the working electrodes 1102', 1102" and reference electrode 1106. Contacts 1104', 1104" used to provide electrical connection between the working electrodes and other components of the sensor system may be formed in a similar manner. As shown, contacts 1104' and 1104" are separated from each other to prevent an electrical connection therebetween. Because the layer removal process is performed on each individual elongated body, instead of a single geometrically complicated elongated body, this particular sensor design (i.e., two elongated bodies placed side by side) may provide ease of manufacturing, as compared to the manufacturing involved with other sensors having other geometries.

After the conductive and insulating layers have been deposited onto the elongated body, and after selected portions of the deposited layers have been removed, a membrane can be applied onto at least a portion of the elongated bodies. In certain embodiments, the membrane system is applied only to the working electrodes, but in other embodiments the membrane system is applied to the entire elongated body. In one embodiment, a membrane system is deposited onto the two working electrodes simultaneously while they are placed together (e.g., by bundling), but in another embodiment, a membrane is deposited onto each individual working electrode, and the two working electrodes are then placed together.

In one exemplary embodiment, the two elongated bodies E1, E2 are bundled together first (e.g., by providing adherence between the insulating layers of the working electrodes) to form a subassembly and an uncoated silver elongated conductive body E3 is then adhered to the subassembly to form an assembly including all three elongated bodies E1, E2, E3. Subsequently, the silver elongated conductive body E3 can be chlorized to form a silver/silver chloride reference electrode.

It should be understood that with any of the embodiments described herein involving multiple working electrodes, one or more working electrodes may be designed to serve as an enzymatic electrode and one or more working electrodes may be designed to serve as a "blank" working electrode configured to measure baseline. This configuration allows for subtraction of a signal associated with the "blank" working electrode (i.e., the baseline non-analyte related signal) from the signal associated with the enzymatic working electrode. The subtraction, in turn, results in a signal that contains substantially reduced (or no) non-analyte-related signal contribution (e.g., contribution from interferents).

Figure 10D:
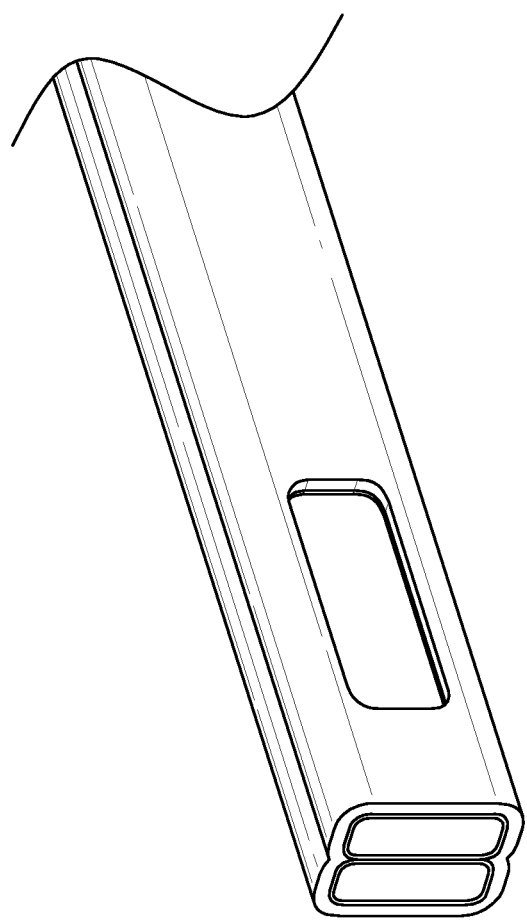
FIG. 10D is a perspective-view schematic illustrating an in vivo portion of a multi-electrode analyte sensor, in another embodiment.

As described elsewhere herein, the elongated body may have any of a variety of cross-sectional shapes. This concept also applies to multi-electrode sensors. For example, even though the elongated bodies of the embodiment illustrated in FIGS. 10 A-10C is shown with a circular or substantially circular cross-sectional shape, it is contemplated that other shapes may be used. By way of example, FIG. 10D is a perspective view of the in vivo portion of one embodiment having a sensor design similar to that of the embodiment illustrated in FIGS. 10A-10C, except that that this particular embodiment has a substantially rectangular cross-section. The rectangular shape may provide advantages in certain instances. For example, a rectangular shape design may provide a larger window area per unit length of etching (e.g., laser ablation). This results in a larger electrode surface per unit length of the elongated body, which in turn, allows for a sensor with a higher sensitivity, as compared to an equivalent sensor with a circular cross section. Additionally, the rectangular cross-section may allow for easier handling (e.g., easier alignment) during the fabrication operations, such as, extrusion, dip-coating, etching, and membrane applications (e.g., with a "drop-on-demand" systems such as ink-jetting.). Furthermore, a rectangular shape may provide for a more compact cross-section, which allows for the sensor to be inserted with a needle with a smaller diameter than an equivalent sensor with a different cross-sectional shape.

Figure 12:
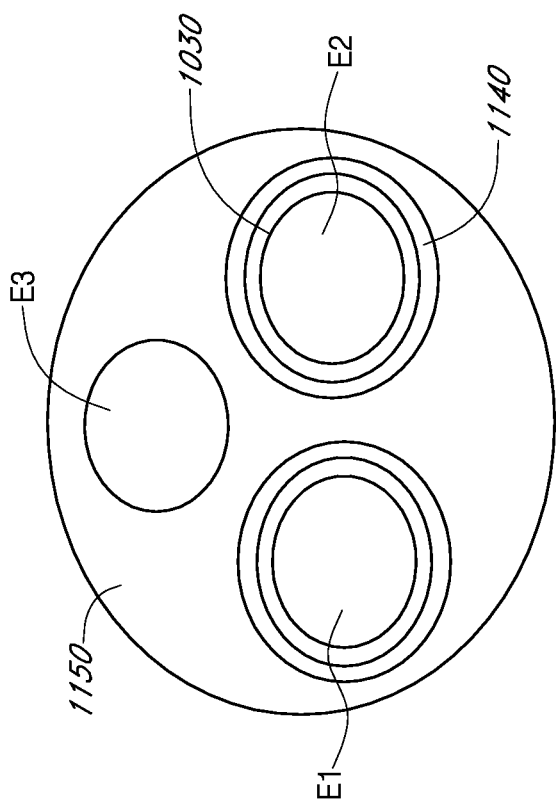
FIG. 12 is a front-view schematic illustrating an in vivo portion of a multi-electrode analyte sensor, in another embodiment.

As described above, in some embodiments, a domain formed of a conductive material or an insulating material may be used to encase multiple electrodes so that they are held together to form a unitary elongated body. In other embodiments, other types of material may be used instead of (or in addition) to a conductive or insulating domain to hold together the multiple elongated bodies. FIG. 12 illustrates one such embodiment. In this particular embodiment, the multi-electrode sensor system 1100 comprises two working electrodes associated with elongated bodies E1, E2 and one reference/counter electrode associated with elongated body E3. Each of the elongated bodies E1, E2, E3 may optionally include an insulating layer 1110, portions of which are removed to expose electroactive portions that correspond to working or reference electrodes. In addition, the elongated bodies E1, E2 associated with the working electrodes include a membrane 1140. Although in this particular embodiment, the elongated body E3 associated with the reference electrode does not include a membrane, in alternative embodiments, a membrane covers at least a portion of the reference electrode. A support structure 1150 is used to hold together the multiple elongated bodies E1, E2, E3. The support structure 1150 may be made from any of a variety of materials, such as, polyurethane, silicone, or certain membrane materials. In addition, the support structure 1150 may contain a combination of hydrophobic and hydrophilic components to ensure favorable bonding properties and permeability to the underlying structure.

Figure 13A:
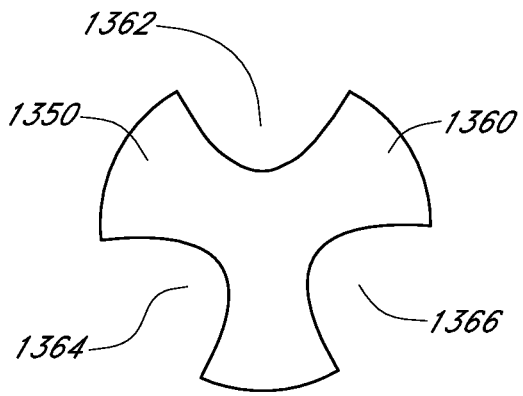
FIG. 13A is a front-view schematic illustrating another embodiment a multi-electrode analyte sensor, during one stage of sensor fabrication.
Figure 13B:
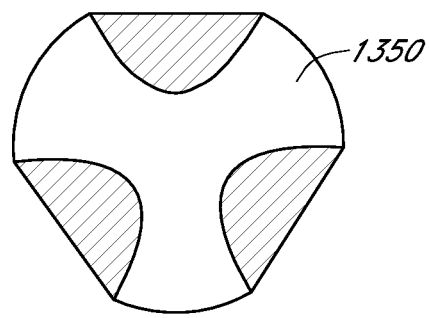
FIG. 13B is a front-view schematic illustrating the embodiment shown in FIG. 13A, during another stage of sensor fabrication.
Figure 13C:
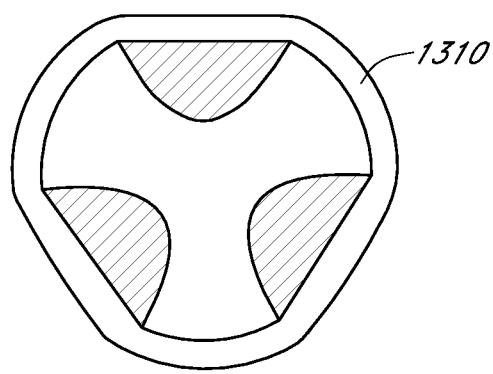
FIG. 13C is a front-view schematic illustrating the embodiment shown in FIG. 13A, during yet another stage of sensor fabrication.

FIGS. 13A-13C illustrates another embodiment of a multi-electrode sensor system and the process for manufacturing it. As illustrated in FIG. 13A, an elongated body in the form of a carrier 1350 is provided which includes grooves 1360 that extend along the longitudinal axis of the carrier 1350. The grooves 1360 are configured to hold a conductive paste, such as, for example, a platinum paste to form a working electrode, or a silver/silver chloride paste to form a reference electrode. Although in this particular embodiment, the carrier 1350 includes three grooves, in other embodiments, the carrier may include more (e.g., 4, 5, 6, 7, 10, 15, 20) or less (e.g., 2) grooves to form a sensor system with any number of working and reference electrodes. In certain embodiments, the carrier 1350 is formed of a non-conductive material to prevent an electrical connection between the different electrodes. As shown in FIG. 13B, two of the grooves 1362, 1364 are then filled with a conductive material (e.g., a conductive metal paste such as a platinum filled screen print ink) to form a working electrode, and one groove 1366 is filled with a different conductive material (e.g., a silver/silver chloride paste) to form a reference electrode. To fill the grooves, a die can be used whereby channels are provided to guide paste to the selected groove. To prevent cross-contamination of the materials in between the grooves, a scraper can be provided at the exit end of the die that scrapes conductive material to be flush with the carrier. As illustrated in FIG. 13C, a membrane system 1310 can then applied to the assembly using any of the processes described elsewhere herein.

Figure 13D:
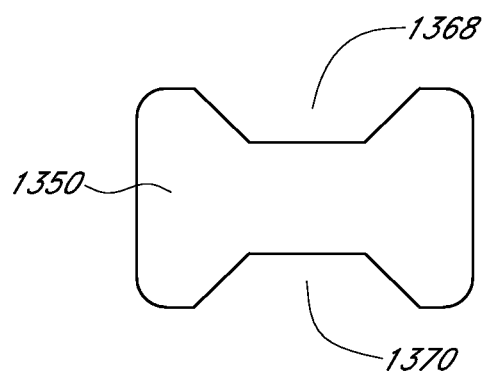
FIG. 13D is a front-view schematic illustrating another embodiment a multi-electrode analyte sensor, during one stage of sensor fabrication.
Figure 13E:
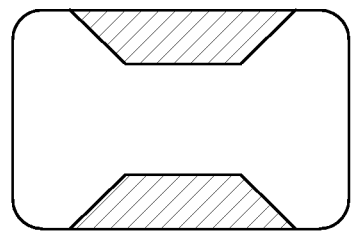
FIG. 13E is a front-view schematic illustrating the embodiment shown in FIG. 13D, during another stage of sensor fabrication.
Figure 13F:
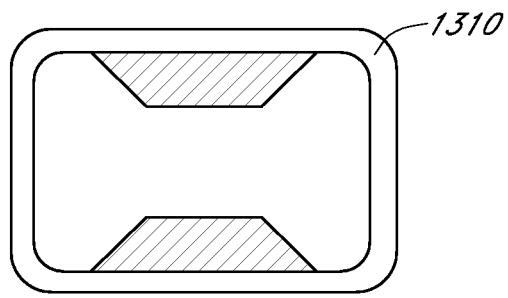
FIG. 13F is a front-view schematic illustrating the embodiment shown in FIG. 13D, during yet another stage of sensor fabrication.
Figure 13G:
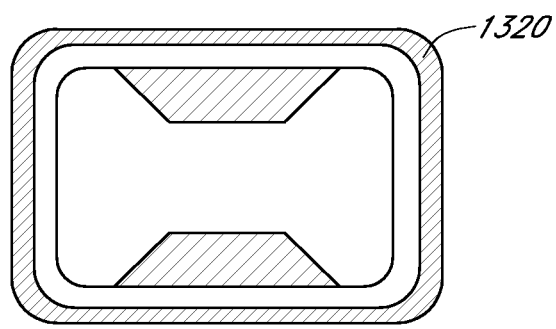
FIG. 13G is a front-view schematic illustrating the embodiment shown in FIG. 13D, during yet another stage of sensor fabrication.

FIGS. 13D-13F illustrates another embodiment similar to the embodiment illustrated in FIGS. 13A-13C. As illustrated in FIG. 13D, in this embodiment, a carrier 1350 is provided that includes two grooves 1368, 1370. As shown in FIG. 13E, the two grooves 1368, 1370 are then filled with a conductive material to form two working electrodes. Next, an insulating layer 1310 is deposited onto the assembly, followed by the deposition of a conductive layer 1320 which forms a reference electrode, as shown in FIGS. 13F-13G. Subsequently, the assembly undergoes an etching process (e.g., laser ablation, chemical etching, grit blasting) to remove certain portions of the insulating layer 1310 and conductive layer 1320, thereby forming working electrodes.

Referring to FIG. 1A, in some embodiments, the sensor 100 comprises a membrane 108 in contact with the electroactive surface (e.g., at least the working electrode). As described elsewhere herein, an implanted sensor can be subjected to repeated bending and/or flexing along a plurality of axes. In order to withstand this harsh treatment and to provide analyte data over 1, 2, 3 or more days, the sensor membrane is configured to withstand repeated compression, flexing and pulling while substantially maintaining membrane function (e.g., without ripping, buckling or tearing). Accordingly, the sensor membrane may be strong yet elastic. Shore hardness is a measure of a material's elasticity. In some embodiments, the membrane comprises a polymer having a Shore hardness of at least about 65 A, 70 A, 75 A, 80 A, 85 A, 90 A, 95 A, 30 D, 35 D, 40 D, 45 D, 50 D, 55 D, 60 D, or more. In some embodiments, the polymer has a Shore hardness of from about 70 A to about 55 D. Polymers having a Shore hardness within the range of from about 70 A to about 55 D include but are not limited to polyurethanes, polyimides, silicones, and the like, such as described elsewhere herein.

In some embodiments, the entire membrane is formed of one or more polymers having a Shore hardness of from about 70 A to about 55 D. However, in other embodiments, only a portion of the membrane, such as a membrane layer or domain, is formed of one of these polymers. In one exemplary embodiment, an outer layer of the membrane is formed of a polymer having a Shore hardness of from about 70 A to about 55 D. In some embodiments, approximately the outer 5%, 10%, 15%, 20%, 25%, 30%, 35%, 35%, 40%, 45%, or 50% of the membrane is formed of a polymer having a Shore hardness of from about 70 A to about 55 D. In some embodiments, the resistance domain is formed from a polymer having a Shore hardness of from about 70 A to about 55 D. Additional membrane domains are also formed of a polymer having a Shore hardness within this range, in other embodiments. In one embodiment, at least a portion of the membrane is formed of a polymer having a Shore hardness of from about 70 A to about 55 D and an enzyme is disposed in the polymer.

As discussed herein, membranes can be formed by any suitable method. It can be desirable to form membranes on the various exposed electrodes of the sensors of some embodiments by dipping the sensor at different lengths, by masking, controlled UV curing, and similar methods.

Figure 6:
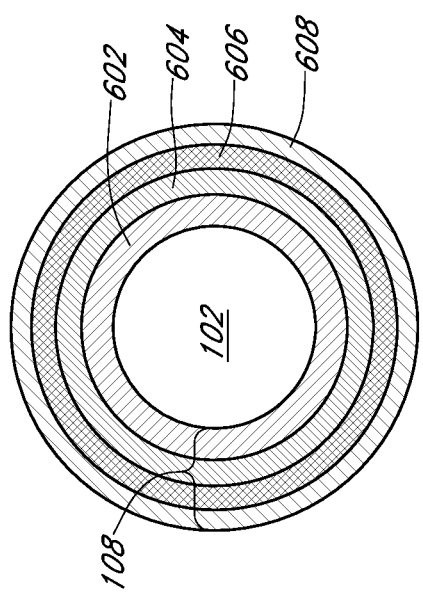
FIG. 6 is a cross-sectional schematic of the analyte sensor of FIG. 1A, taken on line 6-6, in one embodiment.

FIG. 6 is a cross section of the sensor shown in FIG. 1A, taken at line 6-6. A membrane system (see FIG. 6) is deposited over the electroactive surfaces of the sensor and includes a plurality of domains or layers, such as described in more detail below. In some embodiments, the membrane comprises a single layer. In some embodiments, the single layer includes one or more functional domains (e.g., portions or areas). In other embodiments, the membrane comprises two or more layers. In some embodiments, each of the layers performs a different function. Alternative, multiple layers can perform the same function. The membrane system can be deposited on the exposed electroactive surfaces using known thin film techniques (for example, spraying, electro-depositing, dipping, and the like). In one exemplary embodiment, each domain is deposited by dipping the sensor into a solution and drawing out the sensor at a speed that provides the appropriate domain thickness. In another exemplary embodiment, each domain is deposited by spraying the solution onto the sensor for a period of time that provides the appropriate domain thickness. In general, the membrane system can be disposed over (deposited on) the electroactive surfaces using methods appreciated by one skilled in the art.

In general, the membrane system includes a plurality of domains, for example, an electrode domain 602, an interference domain 304, an enzyme domain 606 (for example, including glucose oxidase), and/or a resistance domain 608, as shown in FIG. 6, and can include a high oxygen solubility domain, and/or a bioprotective domain (not shown), such as is described in more detail in U.S. Patent Application Publication No. US-2005-0245799-A1, and such as is described in more detail below. The membrane system can be deposited on the exposed electroactive surfaces using known thin film techniques (for example, vapor deposition, spraying, electro-depositing, dipping, and the like). In alternative embodiments, however, other vapor deposition processes (e.g., physical and/or chemical vapor deposition processes) can be useful for providing one or more of the insulating and/or membrane layers, including ultrasonic vapor deposition, electrostatic deposition, evaporative deposition, deposition by sputtering, pulsed laser deposition, high velocity oxygen fuel deposition, thermal evaporator deposition, electron beam evaporator deposition, deposition by reactive sputtering molecular beam epitaxy, atmospheric pressure chemical vapor deposition (CVD), atomic layer CVD, hot wire CVD, low-pressure CVD, microwave plasma-assisted CVD, plasma-enhanced CVD, rapid thermal CVD, remote plasma-enhanced CVD, and ultra-high vacuum CVD, for example. However, the membrane system can be disposed over (or deposited on) the electroactive surfaces using any known method, as will be appreciated by one skilled in the art. When enzymes are employed, e.g., in certain dual working electrode glucose sensor configurations, for ease of fabrication each of the electrodes can be dipped with an enzyme domain including enzyme. Enzyme over one of the working electrodes (e.g., the second working electrode) can then be denatured/killed, e.g., by exposure to UV or other irradiation, or by exposure to other agents or treatment methods as known in the art for denaturing enzyme. In some embodiments, one or more domains of the membrane systems are formed from materials such as silicone, polytetrafluoroethylene, polyethylene-co-tetrafluoroethylene, polyolefin, polyester, polycarbonate, biostable polytetrafluoroethylene, homopolymers, copolymers, terpolymers of polyurethanes, polypropylene (PP), polyvinylchloride (PVC), polyvinylidene fluoride (PVDF), polybutylene terephthalate (PBT), polymethylmethacrylate (PMMA), polyether ether ketone (PEEK), polyurethanes, cellulosic polymers, polysulfones and block copolymers thereof including, for example, di-block, tri-block, alternating, random and graft copolymers. U.S. Patent Application Publication No. US-2005-0245799-A1 describes biointerface and membrane system configurations and materials that may be applied.

In selected embodiments, the membrane system comprises an electrode domain. The electrode domain 602 is provided to ensure that an electrochemical reaction occurs between the electroactive surfaces of the working electrode and the reference electrode, and thus the electrode domain may be situated more proximal to the electroactive surfaces than the interference and/or enzyme domain. The electrode domain may include a coating that maintains a layer of water at the electrochemically reactive surfaces of the sensor. In other words, the electrode domain is present to provide an environment between the surfaces of the working electrode and the reference electrode, which facilitates an electrochemical reaction between the electrodes. For example, a humectant in a binder material can be employed as an electrode domain; this allows for the full transport of ions in the aqueous environment. The electrode domain can also assist in stabilizing the operation of the sensor by accelerating electrode start-up and drifting problems caused by inadequate electrolyte. The material that forms the electrode domain can also provide an environment that protects against pH-mediated damage that can result from the formation of a large pH gradient due to the electrochemical activity of the electrodes.

In one embodiment, the electrode domain includes hydrophilic polymer film (e.g., a flexible, water-swellable, hydrogel) having a "dry film" thickness of from about 0.05 microns or less to about 20 microns or more, or from about 0.05, 0.1, 0.15, 0.2, 0.25, 0.3, 0.35, 0.4, 0.45, 0.5, 1, 1.5, 2, 2.5, 3, or 3.5 microns to about 4, 5, 6, 7, 8, 9, 10, 11, 12, 13, 14, 15, 16, 17, 18, 19, or 19.5 microns, or from about 3, 2.5, 2, or 1 microns, or less, to about 3.5, 4, 4.5, or 5 microns or more. "Dry film" thickness refers to the thickness of a cured film cast from a coating formulation by standard coating techniques.

In certain embodiments, the electrode domain is formed of a curable mixture of a urethane polymer and a hydrophilic polymer. In some embodiments, the coatings are formed of a polyurethane polymer having carboxylate or hydroxyl functional groups and non-ionic hydrophilic polyether segments, wherein the polyurethane polymer is crosslinked with a water-soluble carbodiimide (e.g., 1-ethyl-3-(3-dimethylaminopropyl)carbodiimide (EDC)) in the presence of polyvinylpyrrolidone and cured at a moderate temperature of about 50° C.

In some embodiments, the electrode domain is formed from a hydrophilic polymer (e.g., a polyamide, a polylactone, a polyimide, a polylactam, a functionalized polyamide, a functionalized polylactone, a functionalized polyimide, a functionalized polylactam or a combination thereof) that renders the electrode domain substantially more hydrophilic than an overlying domain, (e.g., interference domain, enzyme domain). In some embodiments, the electrode domain is formed substantially entirely and/or primarily from a hydrophilic polymer. In some embodiments, the electrode domain is formed substantially entirely from PVP. In some embodiments, the electrode domain is formed entirely from a hydrophilic polymer. Useful hydrophilic polymers include but are not limited to poly-N-vinylpyrrolidone (PVP), poly-N-vinyl-2-piperidone, poly-N-vinyl-2-caprolactam, poly-N-vinyl-3-methyl-2-caprolactam, poly-N-vinyl-3-methyl-2-piperidone, poly-N-vinyl-4-methyl-2-piperidone, poly-N-vinyl-4-methyl-2-caprolactam, poly-N-vinyl-3-ethyl-2-pyrrolidone, poly-N-vinyl-4,5-dimethyl-2-pyrrolidone, polyvinylimidazole, poly-N,N-dimethylacrylamide, polyvinyl alcohol, polyacrylic acid, polyethylene oxide, poly-2-ethyl-oxazoline, copolymers thereof and mixtures thereof. A blend of two or more hydrophilic polymers may be used in some embodiments. In some embodiments, the hydrophilic polymer(s) is not crosslinked. In alternative embodiments, crosslinking may be performed, such as by adding a crosslinking agent, such as but not limited to EDC, or by irradiation at a wavelength sufficient to promote crosslinking between the hydrophilic polymer molecules, which is believed to create a more tortuous diffusion path through the domain.

An electrode domain formed from a hydrophilic polymer (e.g., PVP) has been shown to substantially reduce break-in time of analyte sensors; for example, a glucose sensor utilizing a cellulosic-based interference domain such as described in more detail elsewhere herein. In some embodiments, a uni-component electrode domain formed from a single hydrophilic polymer (e.g., PVP) has been shown to substantially reduce break-in time of a glucose sensor to less than about 2 hours, less than about 1 hour, less than about 20 minutes and/or substantially immediately, such as exemplified in Examples 9 through 11 and 13. Generally, sensor break-in is the amount of time required (after implantation) for the sensor signal to become substantially representative of the analyte concentration. Sensor break-in includes both membrane break-in and electrochemical break-in, which are described in more detail elsewhere herein. In some embodiments, break-in time is less than about 2 hours. In other embodiments, break-in time is less than about 1 hour. In still other embodiments, break-in time is less than about 30 minutes, less than about 20 minutes, less than about 15 minutes, less than about 10 minutes, or less. In one embodiment, sensor break-in occurs substantially immediately. Advantageously, in embodiments wherein the break-in time is about 0 minutes (substantially immediately), the sensor can be inserted and begin providing substantially accurate analyte (e.g., glucose) concentrations almost immediately post-insertion, for example, wherein membrane break-in does not limit start-up time.

While not wishing to be bound by theory, it is believed that providing an electrode domain that is substantially more hydrophilic than the next more distal membrane layer or domain (e.g., the overlaying domain; the layer more distal to the electroactive surface than the electrode domain, such as an interference domain or an enzyme domain) reduces the break-in time of an implanted sensor, by increasing the rate at which the membrane system is hydrated by the surrounding host tissue. While not wishing to be bound by theory, it is believed that, in general, increasing the amount of hydrophilicity of the electrode domain relative to the overlaying layer (e.g., the distal layer in contact with electrode domain, such as the interference domain, enzyme domain, etc.), increases the rate of water absorption, resulting in reduced sensor break-in time. The hydrophilicity of the electrode domain can be substantially increased by the proper selection of hydrophilic polymers, based on their hydrophilicity relative to each other and relative to the overlaying layer (e.g., cellulosic-based interference domain), with certain polymers being substantially more hydrophilic than the overlaying layer. In one exemplary embodiment, PVP forms the electrode domain, the interference domain is formed from a blend of cellulosic derivatives, such as but not limited to cellulose acetate butyrate and cellulose acetate; it is believed that since PVP is substantially more hydrophilic than the cellulosic-based interference domain, the PVP rapidly draws water into the membrane to the electrode domain, and enables the sensor to function with a desired sensitivity and accuracy and starting within a substantially reduced time period after implantation. Reductions in sensor break-in time reduce the amount of time a host has to wait to obtain sensor readings, which is particularly advantageous not only in ambulatory applications, but particularly in hospital settings where time is critical.

While not wishing to be bound by theory, it is believed that when the water absorption of the overlying domain (e.g., the domain overlaying the electrode domain) is less than the water absorption of the electrode domain (e.g., during membrane equilibration), then the difference in water absorption between the two domains will drive membrane equilibration and thus membrane break-in. Namely, increasing the difference in hydrophilicity (e.g., between the two domains) results in an increase in the rate of water absorption, which, in turn, results in a decrease in membrane break-in time and/or sensor break-in time. As discussed elsewhere herein, the relative hydrophilicity of the electrode domain as compared to the overlying domain can be modulated by a selection of more hydrophilic materials for formation of the electrode domain (and/or more hydrophobic materials for the overlying domain(s)). For example, an electrode domain with hydrophilic polymer capable of absorbing larger amounts of water can be selected instead of a second hydrophilic polymer that is capable of absorbing less water than the first hydrophilic polymer. In some embodiments, the water content difference between the electrode domain and the overlaying domain (e.g., during or after membrane equilibration) is from about 1% or less to about 90% or more. In other embodiments, the water content difference between the electrode domain and the overlying domain is from about 10% or less to about 80% or more. In still other embodiments, the water content difference between the electrode domain and the overlying domain is from about 30% or less to about 60% or more. In some embodiments, the electrode domain absorbs 5 wt. % or less to 95 wt. % or more water, or from about 5, 10, 15, 20, 25, 30, 35, 40, 45, or 50 wt. % to about 55, 60, 65, 70, 75, 80, 85, 90 or 95 wt. % water than the adjacent (overlying) domain (e.g., the domain that is more distal to the electroactive surface than the electrode domain).

In another example, the rate of water absorption by a polymer can be affected by other factors, such as but not limited to the polymer's molecular weight. For example, the rate of water absorption by PVP is dependent upon its molecular weight, which is typically from about 40 kDa or less to about 360 kDa or more; with a lower molecular weight PVP (e.g., 40 kDa) absorbing water faster than a higher molecular weight PVP. Accordingly, modulating factors, such as molecular weight, that affect the rate of water absorption by a polymer, can promote the proper selection of materials for electrode domain fabrication. In one embodiment, a lower molecular weight PVP is selected, to reduce break-in time.

The electrode domain may be deposited by known thin film deposition techniques (e.g., spray coating or dip-coating the electroactive surfaces of the sensor). In some embodiments, the electrode domain is formed by dip-coating the electroactive surfaces in an electrode domain solution (e.g., 5, 10, 15, 20, 25 or 30% or more PVP in deionized water) and curing the domain for a time of from about 15 minutes to about 30 minutes at a temperature of from about 40° C. to about 55° C. (and can be accomplished under vacuum (e.g., 20 to 30 mmHg)). In embodiments wherein dip-coating is used to deposit the electrode domain, an insertion rate of from about 1 to about 3 inches per minute into the electrode domain solution may be used, with a dwell time of from about 0.5 to about 2 minutes in the electrode domain solution, and a withdrawal rate of from about 0.25 to about 2 inches per minute from the electrode domain solution provide a functional coating. However, values outside of those set forth above can be acceptable or even desirable in certain embodiments, for example, depending upon solution viscosity and solution surface tension, as is appreciated by one skilled in the art. In one embodiment, the electroactive surfaces of the electrode system are dip-coated one time (one layer) and cured at 50° C. under vacuum for 20 minutes. In another embodiment, the electroactive surfaces of the electrode system is dip-coated and cured at 50° C. under vacuum for 20 minutes a first time, followed by dip coating and curing at 50° C. under vacuum for 20 minutes a second time (two layers). In still other embodiments, the electroactive surfaces can be dip-coated three or more times (three or more layers). In other embodiments, the 1, 2, 3 or more layers of PVP are applied to the electroactive surfaces by spray coating or vapor deposition. In some embodiments, a crosslinking agent (e.g., EDC) can be added to the electrode domain casting solution to promote crosslinking within the domain (e.g., between electrode domain polymer components, latex, etc.). In some alternative embodiments however, no crosslinking agent is used and the electrode domain is not substantially crosslinked.

In some embodiments, the deposited PVP electrode domain has a "dry film" thickness of from about 0.05 microns or less to about 20 microns, or from about 0.05, 0.1, 0.15, 0.2, 0.25, 0.3, 0.35, 0.4, 0.45, 0.5, 1, 1.5, 2, 2.5, 3, or 3.5 microns to about 4, 5, 6, 7, 8, 9, 10, 11, 12, 13, 14, 15, 16, 17, 18, 19, or 19.5 microns, or from about 2, 2.5 or 3 microns to about 3.5, 4, 4.5, or 5 microns. Although an independent electrode domain is described herein, in some embodiments sufficient hydrophilicity can be provided in the interference domain and/or enzyme domain (the domain adjacent to the electroactive surfaces) so as to provide for the full transport of ions in the aqueous environment (e.g. without a distinct electrode domain). In these embodiments, an electrode domain is not necessary.

Interferents are molecules or other species that are reduced or oxidized at the electrochemically reactive surfaces of the sensor, either directly or via an electron transfer agent, to produce a false positive analyte signal (e.g., a non-analyte-related signal). This false positive signal causes the host's analyte concentration (e.g., glucose concentration) to appear higher than the true analyte concentration. False-positive signal is a clinically significant problem in some conventional sensors. For example in a case of a dangerously hypoglycemic situation, wherein the host has ingested an interferent (e.g., acetaminophen), the artificially high glucose signal can lead the host to believe that he is euglycemic (or, in some cases, hyperglycemic). As a result, the host can make inappropriate treatment decisions, such as taking no action, when the proper course of action is to begin eating. In another example, in the case of a euglycemic or hyperglycemic situation, wherein a host has consumed acetaminophen, an artificially high glucose signal caused by the acetaminophen can lead the host to believe that his glucose concentration is much higher than it truly is. Again, as a result of the artificially high glucose signal, the host can make inappropriate treatment decisions, such as giving himself too much insulin, which in turn can lead to a dangerous hypoglycemic episode.

In some embodiments, an interference domain 604 is provided that substantially restricts or blocks the flow of one or more interfering species therethrough; thereby substantially preventing artificial signal increases. Some known interfering species for a glucose sensor, as described in more detail herein, include acetaminophen, ascorbic acid, bilirubin, cholesterol, creatinine, dopamine, ephedrine, ibuprofen, L-dopa, methyl dopa, salicylate, tetracycline, tolazamide, tolbutamide, triglycerides, and uric acid. In general, the interference domain of some embodiments is less permeable to one or more of the interfering species than to the measured species, e.g., the product of an enzymatic reaction that is measured at the electroactive surface(s), such as but not limited to $H_2O_2$.

In one embodiment, the interference domain is formed from one or more cellulosic derivatives. Cellulosic derivatives can include, but are not limited to, cellulose esters and cellulose ethers. In general, cellulosic derivatives include polymers such as cellulose acetate, cellulose acetate butyrate, 2-hydroxyethyl cellulose, cellulose acetate phthalate, cellulose acetate propionate, cellulose acetate trimellitate, and the like, as well as their copolymers and terpolymers with other cellulosic or non-cellulosic monomers. Cellulose is a polysaccharide polymer of β-D-glucose. While cellulosic derivatives may be used in some embodiments, other polymeric polysaccharides having similar properties to cellulosic derivatives can also be employed in other embodiments. Descriptions of cellulosic interference domains can be found in U.S. Patent Application Publication No. US-2006-0229512-A1, U.S. Patent Application Publication No. US-2007-0173709-A1, U.S. Patent Application Publication No. US-2006-0253012-A1, and U.S. Patent Application Publication No. US-2007-0213611-A1.

In some embodiments, the interferent's equivalent glucose signal response (measured by the sensor) is 50 mg/dL or less. In certain embodiments, the interferent produces an equivalent glucose signal response of 40 mg/dL or less. In some embodiments, the interferent produces an equivalent glucose signal response of less than about 30, 20 or 10 mg/dL. In one exemplary embodiment, the interference domain is configured to substantially block acetaminophen passage therethrough, wherein the equivalent glucose signal response of the acetaminophen is less than about 30 mg/dL.

In alternative embodiments, the interference domain is configured to substantially block a therapeutic dose of acetaminophen. The term "therapeutic dose" as used herein is a broad term, and is to be given its ordinary and customary meaning to a person of ordinary skill in the art (and is not to be limited to a special or customized meaning), and refers without limitation to the quantity of any substance required to effect the cure of a disease, to relieve pain, or that will correct the manifestations of a deficiency of a particular factor in the diet, such as the effective dose used with therapeutically applied compounds, such as drugs. For example, a therapeutic dose of acetaminophen can be an amount of acetaminophen required to relieve headache pain or reduce a fever. As a further example, 1,000 mg of acetaminophen taken orally, such as by swallowing two 500 mg tablets of acetaminophen, is the therapeutic dose frequently taken for headaches. In some embodiments, the interference membrane is configured to block a therapeutic dose of acetaminophen, wherein the equivalent glucose signal response of the acetaminophen is less than about 60 mg/dL. In one embodiment, the interference membrane is configured to block a therapeutic dose of acetaminophen, wherein the equivalent glucose signal response of the acetaminophen is less than about 40 mg/dL. In another embodiment, the interference membrane is configured to block a therapeutic dose of acetaminophen, wherein the equivalent glucose signal response of the acetaminophen is less than about 30 mg/dL.

In some alternative embodiments, additional polymers, such as NAFION®, can be used in combination with cellulosic derivatives to provide equivalent and/or enhanced function of the interference domain. As one example, a layer of a 5 wt. % NAFION® casting solution was applied over a previously applied (e.g., and cured) layer of 8 wt. % cellulose acetate, e.g., by dip coating at least one layer of cellulose acetate and subsequently dip coating at least one layer NAFION® onto a needle-type sensor. Any number of coatings or layers formed in any order may be suitable for forming the interference domain.

In some alternative embodiments, other polymer types that can be utilized as a base material for the interference domain include polyurethanes, polymers having pendant ionic groups, and polymers having controlled pore size, for example. In one such alternative embodiment, the interference domain includes a thin, hydrophobic membrane that is non-swellable and restricts diffusion of high molecular weight species. The interference domain is permeable to relatively low molecular weight substances, such as hydrogen peroxide, but restricts the passage of higher molecular weight substances, including glucose and ascorbic acid. Other systems and methods for reducing or eliminating interference species that can be applied to the membrane system are described in U.S. Pat. No. 7,074,307, U.S. Patent Application Publication No. US-2005-0176136-A1, U.S. Pat. No. 7,081,195, and U.S. Patent Application Publication No. US-2005-0143635-A1. In some alternative embodiments, a distinct interference domain is not included.

In some embodiments, the interference domain is deposited either directly onto the electroactive surfaces of the sensor or onto the distal surface of the electrode domain, for a domain thickness of from about 0.05 microns to about 20 microns, or from about 0.05, 0.1, 0.15, 0.2, 0.25, 0.3, 0.35, 0.4, 0.45, 0.5, 1, 1.5, 2, 2.5, 3, or 3.5 microns to about 4, 5, 6, 7, 8, 9, 10, 11, 12, 13, 14, 15, 16, 17, 18, 19, or 19.5 microns, or from about 1, 1.5 or 2 microns to about 2.5 or 3 microns. Thicker membranes can also be desirable in certain embodiments, but thinner membranes may be used because they have a lower impact on the rate of diffusion of hydrogen peroxide from the enzyme membrane to the electroactive surface(s).

In general, the membrane systems of some embodiments can be formed and/or deposited on the exposed electroactive surfaces (e.g., one or more of the working and reference electrodes) using known thin film techniques (for example, casting, spray coating, drawing down, electro-depositing, dip coating, and the like), however casting or other known application techniques can also be utilized. The interference domain may be deposited by spray or dip coating. In one exemplary embodiment of a needle-type (transcutaneous) sensor such as described herein, the interference domain is formed by dip coating the sensor into an interference domain solution using an insertion rate of from about 0.5 inch/min to about 60 inches/min, or about 1 inch/min, a dwell time of from about 0 minute to about 2 minutes, or about 1 minute, and a withdrawal rate of from about 0.5 inch/minute to about 60 inches/minute, or about 1 inch/minute, and curing (drying) the domain from about 1 minute to about 30 minutes, or from about 3 minutes to about 15 minutes (and can be accomplished at room temperature or under vacuum (e.g., 20 to 30 mmHg)). In one exemplary embodiment including cellulose acetate butyrate interference domain, a 3-minute cure (i.e., dry) time is sometimes between each layer applied. In another exemplary embodiment employing a cellulose acetate interference domain, a 15 minute cure (i.e., dry) time is used between each layer applied.

In some embodiments, the dip process can be repeated at least one time and up to 10 times or more. In other embodiments, only one dip is performed. The number of repeated dip processes used depends upon the cellulosic derivative(s) used, their concentration, conditions during deposition (e.g., dipping) and the desired thickness (e.g., sufficient thickness to provide functional blocking of certain interferents), and the like. In some embodiments, 1 to 3 microns may be used for the interference domain thickness; however, values outside of these can be acceptable or even desirable in certain embodiments, for example, depending upon viscosity and surface tension, as is appreciated by one skilled in the art. In one exemplary embodiment, an interference domain is formed from three layers of cellulose acetate butyrate. In another exemplary embodiment, an interference domain is formed from 10 layers of cellulose acetate. In another embodiment, an interference domain is formed from 1 layer of a blend of cellulose acetate and cellulose acetate butyrate. In alternative embodiments, the interference domain can be formed using any known method and combination of cellulose acetate and cellulose acetate butyrate, as will be appreciated by one skilled in the art. In some embodiments, the electroactive surface can be cleaned, smoothed or otherwise treated prior to application of the interference domain. In some embodiments, the interference domain of some embodiments can be useful as a bioprotective or biocompatible domain, namely, a domain that interfaces with host tissue when implanted in an animal (e.g., a human) due to its stability and biocompatibility. In still other embodiments, other portions of the membrane system, such as but not limited to the enzyme domain and/or the resistance domain can be configured for interference blocking. In still other embodiments, an interference domain can be located either more distally or proximally to the electroactive surface than other membrane domains. For example, an interference domain can be located more distal to the electroactive surface than an enzyme domain or a resistance domain, in some embodiments.

In certain embodiments, the membrane system further includes an enzyme domain 606 disposed more distally from the electroactive surfaces than the interference domain; however other configurations can be desirable. In certain embodiments, the enzyme domain provides an enzyme to catalyze the reaction of the analyte and its co-reactant, as described in more detail below. In the some embodiments of a glucose sensor, the enzyme domain includes glucose oxidase (GOX); however other oxidases, for example, galactose oxidase or uricase oxidase, can also be used. In some embodiments, the enzyme domain is configured and arranged for detection of at least one of albumin, alkaline phosphatase, alanine transaminase, aspartate aminotransferase, bilirubin, blood urea nitrogen, calcium, $CO_2$, chloride, creatinine, glucose, gamma-glutamyl transpeptidase, hematocrit, lactate, lactate dehydrogenase, magnesium, oxygen, pH, phosphorus, potassium, sodium, total protein, uric acid, a metabolic marker, a drug, various minerals, various metabolites, and/or the like. In a further embodiment, the sensor is configured and arranged to detect two or more of albumin, alkaline phosphatase, alanine transaminase, aspartate aminotransferase, bilirubin, blood urea nitrogen, calcium, $CO_2$, chloride, creatinine, glucose, gamma-glutamyl transpeptidase, hematocrit, lactate, lactate dehydrogenase, magnesium, oxygen, pH, phosphorus, potassium, sodium, total protein, uric acid, a metabolic marker, a drug, various minerals, various metabolites, and/or the like.

For an enzyme-based electrochemical glucose sensor to perform well, the sensor's response may be limited by neither enzyme activity nor co-reactant concentration. Because enzymes, including glucose oxidase, are subject to deactivation as a function of time even in ambient conditions, this behavior is compensated for in forming the enzyme domain. In some embodiments, the enzyme domain is constructed of aqueous dispersions of colloidal polyurethane polymers including the enzyme. However, in alternative embodiments the enzyme domain is constructed from an oxygen enhancing material, for example, silicone, or fluorocarbon, in order to provide a supply of excess oxygen during transient ischemia. The enzyme may be immobilized within the domain. See, e.g., U.S. Patent Application Publication No. US-2005-0054909-A1. In some embodiments, the enzyme domain is deposited onto the interference domain for a domain thickness of from about 0.05 micron to about 20 microns, or from about 0.05, 0.1, 0.15, 0.2, 0.25, 0.3, 0.35, 0.4, 0.45, 0.5, 1, 1.5, 2, 2.5, 3, or 3.5 microns to about 4, 5, 6, 7, 8, 9, 10, 11, 12, 13, 14, 15, 16, 17, 18, 19, or 19.5 microns, or from about 2, 2.5 or 3 microns to about 3.5, 4, 4.5, or 5 microns. However in some embodiments, the enzyme domain can be deposited directly onto the electroactive surfaces. The enzyme domain may be deposited by spray or dip coating. In one embodiment of needle-type (transcutaneous) sensor such as described herein, the enzyme domain is formed by dip coating the interference domain coated sensor into an enzyme domain solution and curing the domain for from about 15 to about 30 minutes at a temperature of from about 40° C. to about 55° C. (and can be accomplished under vacuum (e.g., 20 to 30 mmHg)). In embodiments wherein dip coating is used to deposit the enzyme domain at room temperature to provide a functional coating, the insertion rate used may be from about 0.25 inch per minute to about 3 inches per minute, with a dwell time of from about 0.5 minutes to about 2 minutes, and a withdrawal rate of from about 0.25 inch per minute to about 2 inches per minute. However, values outside of those set forth above can be acceptable or even desirable in certain embodiments, for example, depending upon viscosity and surface tension, as is appreciated by one skilled in the art. In one embodiment, the enzyme domain is formed by dip coating two times (namely, forming two layers) in an enzyme domain solution and curing at 50° C. under vacuum for 20 minutes. However, in some embodiments, the enzyme domain can be formed by dip coating and/or spray coating one or more layers at a predetermined concentration of the coating solution, insertion rate, dwell time, withdrawal rate, and/or desired thickness.

Enzymatic analyte sensors are dependent upon the kinetics of the enzymes that they comprise. As is understood by one skilled in the art, in order to calculate the concentration of one reactant/analyte (e.g., using a defined amount of enzyme) all other reactants/co-reactants are present in excess. However, in the body, this is often not the case; sometimes the analyte is in excess. Accordingly, in some embodiments, the sensor membrane is configured and arranged to restrict diffusion of the analyte to the enzyme domain, such that the analyte can be measured accurately. In some embodiments, the membrane system includes a resistance domain 608 disposed more distal from the electroactive surfaces than the enzyme domain. Although the following description is directed to a resistance domain for a glucose sensor, the resistance domain can be modified for other analytes and co-reactants as well.

With respect to glucose sensors, there exists a molar excess of glucose relative to the amount of oxygen in blood; that is, for every free oxygen molecule in extracellular fluid, there are typically more than 100 glucose molecules present (see Updike et al., Diabetes Care 5:207-21 (1982)). However, an immobilized enzyme-based glucose sensor employing oxygen as co-reactant may be supplied with oxygen in non-rate-limiting excess in order for the sensor to respond linearly to changes in glucose concentration, while not responding to changes in oxygen concentration. Specifically, when a glucose-monitoring reaction is oxygen limited, linearity is not achieved above minimal concentrations of glucose. Without a semipermeable membrane situated over the enzyme domain to control the flux of glucose and oxygen, a linear response to glucose levels can be obtained only for glucose concentrations of up to about 40 mg/dL. However, in a clinical setting, a linear response to glucose levels is desirable up to at least about 400 mg/dL.

The resistance domain includes a semipermeable membrane that controls the flux of oxygen and glucose to the underlying enzyme domain, thereby rendering oxygen in a non-rate-limiting excess. As a result, the upper limit of linearity of glucose measurement is extended to a much higher value than that which is achieved without the resistance domain. In one embodiment, the resistance domain exhibits an oxygen to glucose permeability ratio of from about 50:1 or less to about 400:1 or more, or about 200:1. As a result, one-dimensional reactant diffusion is adequate to provide excess oxygen at all reasonable glucose and oxygen concentrations found in the subcutaneous matrix (See Rhodes et al., Anal. Chem., 66:1520-1529 (1994)).

In alternative embodiments, a lower ratio of oxygen-to-glucose can be sufficient to provide excess oxygen by using a high oxygen solubility domain (for example, a silicone or fluorocarbon-based material or domain) to enhance the supply/transport of oxygen to the enzyme domain. If more oxygen is supplied to the enzyme, then more glucose can also be supplied to the enzyme without creating an oxygen rate-limiting excess. In alternative embodiments, the resistance domain is formed from a silicone composition, such as is described in U.S. Patent Application Publication No. US-2005-0090607-A1.

In one embodiment, the resistance domain includes a polyurethane membrane with both hydrophilic and hydrophobic regions to control the diffusion of glucose and oxygen to an analyte sensor, the membrane being fabricated easily and reproducibly from commercially available materials. A suitable hydrophobic polymer component is a polyurethane, or polyetherurethaneurea. Polyurethane is a polymer produced by the condensation reaction of a diisocyanate and a difunctional hydroxyl-containing material. A polyurethaneurea is a polymer produced by the condensation reaction of a diisocyanate and a difunctional amine-containing material. Diisocyanates that may be used include, but are not limited to, aliphatic diisocyanates containing from about 4 to about 8 methylene units. Diisocyanates containing cycloaliphatic moieties can also be useful in the preparation of the polymer and copolymer components of the membranes of some embodiments. The material that forms the basis of the hydrophobic matrix of the resistance domain can be any of those known in the art as appropriate for use as membranes in sensor devices and as having sufficient permeability to allow relevant compounds to pass through it, for example, to allow an oxygen molecule to pass through the membrane from the sample under examination in order to reach the active enzyme or electrochemical electrodes. Examples of materials which can be used to make non-polyurethane type membranes include vinyl polymers, polyethers, polyesters, polyamides, inorganic polymers such as polysiloxanes and polycarbosiloxanes, natural polymers such as cellulosic and protein based materials, and mixtures or combinations thereof.

In one embodiment, the hydrophilic polymer component is polyethylene oxide. For example, one useful hydrophobic-hydrophilic copolymer component is a polyurethane polymer that includes about 20% hydrophilic polyethylene oxide. The polyethylene oxide portions of the copolymer are thermodynamically driven to separate from the hydrophobic portions of the copolymer and the hydrophobic polymer component. The 20% polyethylene oxide-based soft segment portion of the copolymer used to form the final blend affects the water pick-up and subsequent glucose permeability of the membrane.

In some embodiments, the resistance domain is formed from a silicone polymer modified to allow analyte (e.g., glucose) transport.

In some embodiments, the resistance domain is formed from a silicone polymer/hydrophobic-hydrophilic polymer blend. In one embodiment, The hydrophobic-hydrophilic polymer for use in the blend may be any suitable hydrophobic-hydrophilic polymer, including but not limited to components such as polyvinylpyrrolidone (PVP), polyhydroxyethyl methacrylate, polyvinylalcohol, polyacrylic acid, polyethers such as polyethylene glycol or polypropylene oxide, and copolymers thereof, including, for example, di-block, tri-block, alternating, random, comb, star, dendritic, and graft copolymers (block copolymers are discussed in U.S. Pat. No. 4,803,243 and U.S. Pat. No. 4,686,044). In one embodiment, the hydrophobic-hydrophilic polymer is a copolymer of poly(ethylene oxide) (PEO) and poly(propylene oxide) (PPO). Suitable such polymers include, but are not limited to, PEO-PPO diblock copolymers, PPO-PEO-PPO triblock copolymers, PEO-PPO-PEO triblock copolymers, alternating block copolymers of PEO-PPO, random copolymers of ethylene oxide and propylene oxide, and blends thereof. In some embodiments, the copolymers may be optionally substituted with hydroxy substituents. Commercially available examples of PEO and PPO copolymers include the PLURONIC® brand of polymers available from BASF®. In one embodiment, PLURONIC® F-127 is used. Other PLURONIC® polymers include PPO-PEO-PPO triblock copolymers (e.g., PLURONIC® R products). Other suitable commercial polymers include, but are not limited to, SYNPERONICS® products available from UNIQEMA®. U.S. Patent Application Publication No. US-2007-0244379-A1 describes systems and methods suitable for the resistance and/or other domains of the membrane system.

In some embodiments, the resistance domain is deposited onto the enzyme domain to yield a domain thickness of from about 0.05 microns to about 20 microns, or from about 0.05, 0.1, 0.15, 0.2, 0.25, 0.3, 0.35, 0.4, 0.45, 0.5, 1, 1.5, 2, 2.5, 3, or 3.5 microns to about 4, 5, 6, 7, 8, 9, 10, 11, 12, 13, 14, 15, 16, 17, 18, 19, or 19.5 microns, or from about 2, 2.5 or 3 microns to about 3.5, 4, 4.5, or 5 microns. The resistance domain may be deposited onto the enzyme domain by vapor deposition, spray coating, or dip coating. In one embodiment, spray coating is the preferred deposition technique. The spraying process atomizes and mists the solution, and therefore most or all of the solvent is evaporated prior to the coating material settling on the underlying domain, thereby minimizing contact of the solvent with the enzyme.

In another embodiment, physical vapor deposition (e.g., ultrasonic vapor deposition) is used for coating one or more of the membrane domain(s) onto the electrodes, wherein the vapor deposition apparatus and process include an ultrasonic nozzle that produces a mist of micro-droplets in a vacuum chamber. In these embodiments, the micro-droplets move turbulently within the vacuum chamber, isotropically impacting and adhering to the surface of the substrate. Advantageously, vapor deposition as described above can be implemented to provide high production throughput of membrane deposition processes (e.g., at least about 20 to about 200 or more electrodes per chamber), greater consistency of the membrane on each sensor, and increased uniformity of sensor performance, for example, as described below.

In some embodiments, depositing the resistance domain (for example, using one of the techniques described above) includes formation of a membrane system that substantially blocks or resists ascorbate (a known electrochemical interferent in hydrogen peroxide-measuring glucose sensors). While not wishing to be bound by theory, it is believed that during the process of depositing the resistance domain, a structural morphology is formed that is characterized in that ascorbate does not substantially permeate therethrough.

In one embodiment, the resistance domain is deposited on the enzyme domain by spray coating a solution of from about 1 wt. % to about 5 wt. % polymer and from about 95 wt. % to about 99 wt. % solvent. In spraying a solution of resistance domain material, including a solvent, onto the enzyme domain, it is desirable to mitigate or substantially reduce any contact with enzyme of any solvent in the spray solution that can deactivate the underlying enzyme of the enzyme domain. Tetrahydrofuran (THF) is one solvent that minimally or negligibly affects the enzyme of the enzyme domain upon spraying. Other solvents can also be suitable for use, as is appreciated by one skilled in the art.

Although a variety of spraying or deposition techniques can be used, spraying the resistance domain material and rotating the sensor at least one time by 180° can typically provide adequate coverage by the resistance domain. Spraying the resistance domain material and rotating the sensor at least two times by 120° provides even greater coverage (one layer of 360° coverage), thereby ensuring resistivity to glucose, such as is described in more detail above.

In some embodiment, the resistance domain is spray coated and subsequently cured for a time of from about 15 minutes to about 90 minutes at a temperature of from about 40° C. to about 60° C. (and can be accomplished under vacuum (e.g., from 20 to 30 mmHg)). A cure time of up to about 90 minutes or more can be advantageous to ensure complete drying of the resistance domain.

In one embodiment, the resistance domain is formed by spray coating at least six layers (namely, rotating the sensor seventeen times by 120° for at least six layers of 360° coverage) and curing at 50° C. under vacuum for 60 minutes. However, the resistance domain can be formed by dip coating or spray coating any layer or plurality of layers, depending upon the concentration of the solution, insertion rate, dwell time, withdrawal rate, and/or the desired thickness of the resulting film. Additionally, curing in a convention oven can also be employed.

In certain embodiments, a variable frequency microwave oven can be used to cure the membrane domains/layers. In general, microwave ovens directly excite the rotational mode of solvents. Consequently, microwave ovens cure coatings from the inside out rather than from the outside in as with conventional convection ovens. This direct rotational mode excitation is responsible for the typically observed "fast" curing within a microwave oven. In contrast to conventional microwave ovens, which rely upon a fixed frequency of emission that can cause arcing of dielectric (metallic) substrates if placed within a conventional microwave oven, Variable Frequency Microwave (VFM) ovens emit thousands of frequencies within 100 milliseconds, which substantially eliminates arcing of dielectric substrates. Consequently, the membrane domains/layers can be cured even after deposition on metallic electrodes as described herein. While not wishing to be bound by theory, it is believe that VFM curing can increase the rate and completeness of solvent evaporation from a liquid membrane solution applied to a sensor, as compared to the rate and completeness of solvent evaporation observed for curing in conventional convection ovens. In certain embodiments, VFM is can be used together with convection oven curing to further accelerate cure time. In some sensor applications wherein the membrane is cured prior to application on the electrode (see, for example, U.S. Patent Application Publication No. US-2005-0245799-A1, conventional microwave ovens (e.g., fixed frequency microwave ovens) can be used to cure the membrane layer.

A variety of therapeutic (bioactive) agents can be used with the analyte sensor system of some embodiments. In some embodiments, the therapeutic agent is an anticoagulant. In some embodiments, an anticoagulant is included in the analyte sensor system to prevent coagulation within or on the sensor (e.g., within or on the catheter or within or on the sensor). In some embodiments, the therapeutic agent is an antimicrobial, such as but not limited to an antibiotic or antifungal compound. In some embodiments, the therapeutic agent is an antiseptic and/or disinfectant. Therapeutic agents can be used alone or in combination of two or more of them. The therapeutic agents can be dispersed throughout the material of the sensor (and/or catheter). In some embodiments, the membrane system of some embodiments includes a therapeutic agent, which is incorporated into at least a portion of the membrane system, or which is incorporated into the device and adapted to diffuse through the membrane. There are a variety of systems and methods by which the therapeutic agent is incorporated into the membrane. In some embodiments, the therapeutic agent is incorporated at the time of manufacture of the membrane system. For example, the therapeutic agent can be blended prior to curing the membrane system, or subsequent to membrane system manufacture, for example, by coating, imbibing, solvent-casting, or sorption of the bioactive agent into the membrane system. Although the therapeutic agent may be incorporated into the membrane system, in some embodiments the therapeutic agent can be administered concurrently with, prior to, or after insertion of the device intravascularly, for example, by oral administration, or locally, for example, by subcutaneous injection near the implantation site. A combination of therapeutic agent incorporated in the membrane system and therapeutic agent administration locally and/or systemically can be used in certain embodiments.

As a non-limiting example, in some embodiments, the analyte sensor 100 is a continuous electrochemical analyte sensor configured to provide at least one working electrode and at least one reference electrode, which are configured to measure a signal associated with a concentration of the analyte in the host, such as described in more detail below. The output signal is typically a raw data stream that is used to provide a useful value of the measured analyte concentration in a host to the patient or doctor, for example. However, the analyte sensors of some embodiments comprise at least one additional working electrode configured to measure at least one additional signal, as discussed elsewhere herein. For example, in some embodiments, the additional signal is associated with the baseline and/or sensitivity of the analyte sensor, thereby enabling monitoring of baseline and/or sensitivity changes that may occur over time.

In general, electrochemical continuous analyte sensors define a relationship between sensor-generated measurements (for example, current in pA, nA, or digital counts after A/D conversion) and a reference measurement (for example, glucose concentration mg/dL or mmol/L) that are meaningful to a user (for example, patient or doctor). For example, in the case of an implantable diffusion-based glucose oxidase electrochemical glucose sensor, the sensing mechanism generally depends on phenomena that are linear with glucose concentration, for example: (1) diffusion of glucose through a membrane system (for example, biointerface membrane and membrane system) situated between implantation site and/or the electrode surface, (2) an enzymatic reaction within the membrane system, and (3) diffusion of the $H_2O_2$ to the sensor. Because of this linearity, calibration of the sensor can be understood by solving an equation:

$$y=mx+b$$

wherein y represents the sensor signal (e.g., counts), x represents the estimated glucose concentration (e.g., mg/dL), m represents the sensor sensitivity to glucose (e.g., counts/mg/dL), and b represents the baseline signal (e.g., counts). When both sensitivity m and baseline (background) b change over time in vivo, calibration has generally requires at least two independent, matched data pairs $(x_1, y_1; x_2, y_2)$ to solve for m and b and thus allow glucose estimation when only the sensor signal, y is available. Matched data pairs can be created by matching reference data (for example, one or more reference glucose data points from a blood glucose meter, or the like) with substantially time corresponding sensor data (for example, one or more glucose sensor data points) to provide one or more matched data pairs, such as described in co-pending U.S. Patent Application Publication No. US-2005-0027463-A1. In some implantable glucose sensors, such as described in more detail in U.S. Pat. No. 6,329,161 to Heller et al., the sensing layer utilizes immobilized mediators (e.g., redox compounds) to electrically connect the enzyme to the working electrode, rather than using a diffusional mediator. In some implantable glucose sensors, such as described in more detail in U.S. Pat. No. 4,703,756, the system has two oxygen sensors situated in an oxygen-permeable housing, one sensor being unaltered and the other contacting glucose oxidase allowing for differential measurement of oxygen content in body fluids or tissues indicative of glucose levels. A variety of systems and methods of measuring glucose in a host are known, all of which may benefit from some of all of the embodiments to provide a sensor having a signal-to-noise ratio that is not substantially affected by non-constant noise.

Advantageously, continuous analyte monitoring is enabled. For example, when the analyte is glucose, continuous glucose monitoring enables tight glucose control, which can lead to reduced morbidity and mortality among diabetic hosts. In some embodiments, the medical staff is not unduly burdened by additional patient interaction requirements. Advantageously, there is no net sample (e.g., blood) loss for the host, which is a critical feature in some clinical settings. For example, in a neonatal intensive care unit, the host is extremely small and loss of even a few milliliters of blood can be life threatening. Furthermore, returning the body fluid sample to the host, instead of delivering to a waste container greatly reduces the accumulation of biohazardous waste that requires special disposal procedures. The integrated sensor system components, as well as their use in conjunction with an indwelling analyte sensor, are discussed in greater detail below.

A variety of known sensor configurations can be employed with the sensor systems described herein, such as U.S. Pat. No. 5,711,861 to Ward et al., U.S. Pat. No. 6,642,015 to Vachon et al., U.S. Pat. No. 6,654,625 to Say et al., U.S. Pat. No. 6,565,509 to Say et al., U.S. Pat. No. 6,514,718 to Heller, U.S. Pat. No. 6,465,066 to Essenpreis et al., U.S. Pat. No. 6,214,185 to Offenbacher et al., U.S. Pat. No. 5,310,469 to Cunningham et al., and U.S. Pat. No. 5,683,562 to Shaffer et al., U.S. Pat. No. 6,579,690 to Bonnecaze et al., U.S. Pat. No. 6,484,046 to Say et al., U.S. Pat. No. 6,512,939 to Colvin et al., U.S. Pat. No. 6,424,847 to Mastrototaro et al., U.S. Pat. No. 6,424,847 to Mastrototaro et al, U.S. Patent Application Publication No. US-2006-0020187-A1 to Brister et al., U.S. Patent Application Publication No. US-2007-0027370-A1 to Brauker et al., U.S. Patent Application Publication No. US-2005-0143635-A1 to Kamath et al., U.S. Patent Application Publication No. US-2007-0027385-A1 to Brister et al., U.S. Patent Application Publication No. US-2007-0213611-A1 to Simpson et al., U.S. Patent Application Publication No. US-2008-0083617-A1 to Simpson et al., U.S. Patent Application Publication No. US-2008-0119703-A1 to Brister et al., U.S. Patent Application Publication No. US-2008-0108942-A1 to Brister et al., and U.S. Patent Application Publication No. US-2009-0018424-A1 Kamath et al., for example. The above-referenced patents and publications are not inclusive of all applicable analyte sensors; in general, it should be understood that the disclosed embodiments are applicable to a variety of analyte sensor configurations.

In some embodiments, the dual-electrode sensor includes electronics (e.g., a processor module, processing memory) that are operably connected to the first and second working electrodes and are configured to provide the first and second signals to generate analyte concentration data substantially without signal contribution due to non-analyte-related noise. For example, the sensor electronics process and/or analyze the signals from the first and second working electrodes and calculate the portion of the first electrode signal that is due to analyte concentration only. The portion of the first electrode signal that is not due to the analyte concentration can be considered to be background, such as but not limited to noise. Accordingly, in one embodiment of a dual-electrode sensor system configured for fluid communication with a host's circulatory system (e.g., via a vascular access device) the system comprising electronics operably connected to the first and second working electrodes; the electronics are configured to process the first and second signals to generate analyte concentration data substantially without signal contribution due to noise.

In certain embodiments, the sensor electronics (e.g., electronic components) are operably connected to the first and second working electrodes. The electronics are configured to calculate at least one analyte sensor data point. For example, the electronics can include a potentiostat, A/D converter, RAM, ROM, transmitter, and the like. In some embodiments, the potentiostat converts the raw data (e.g., raw counts) collected from the sensor to a value familiar to the host and/or medical personnel. For example, the raw counts from a glucose sensor can be converted to milligrams of glucose per deciliter of glucose (e.g., mg/dL). In some embodiments, the electronics are operably connected to the first and second working electrodes and are configured to process the first and second signals to generate a glucose concentration substantially without signal contribution due to non-glucose noise artifacts. The sensor electronics determine the signals from glucose and non-glucose related signal with an overlapping measuring potential (e.g., from a first working electrode) and then non-glucose related signal with an overlapping measuring potential (e.g., from a second electrode). The sensor electronics then use these data to determine a substantially glucose-only concentration, such as but not limited to subtracting the second electrode's signal from the first electrode's signal, to give a signal (e.g., data) representative of substantially glucose-only concentration, for example. In general, the sensor electronics may perform additional operations, such as but not limited to data smoothing and noise analysis.

In certain embodiments, the dual-electrode sensor includes electronics (e.g., a processor module, processing memory) that are operably connected to the first and second working electrodes and are configured to provide the first and second signals to generate an analyte concentration data substantially without signal contribution due to non-analyte-related noise. For example, the sensor electronics process and/or analyze the signals from the first and second working electrodes and calculate the portion of the first electrode signal that is due to analyte concentration only. The portion of the first electrode signal that is not due to the analyte concentration can be considered to be background, such as but not limited to noise. Accordingly, in one embodiment of a dual-electrode sensor system configured for fluid communication with a host's circulatory system (e.g., via a vascular access device) the system comprising electronics operably connected to the first and second working electrodes; the electronics are configured to process the first and second signals to generate analyte concentration data substantially without signal contribution due to noise.

In some embodiments, the dual-electrode analyte sensor includes a reference sensor/system, as described elsewhere therein, whereby reference data can be provided for calibration (e.g., internal to the system), without the use of an external (e.g., separate from the system) analyte-measuring device. In an exemplary embodiment, the dual-electrode sensor is a glucose sensor and external glucose data points (e.g., from a hand-held glucose meter or a YSI device) are not required for calibration of a dual-electrode glucose sensor system that includes a reference sensor. In some embodiments, the reference sensor is configured to be disposed within the same local environment as the dual-electrode analyte sensor, such that the reference sensor and the dual-electrode analyte sensor can be simultaneously exposed to a sample. In some embodiments, the reference sensor/system can be disposed remotely from the dual-electrode sensor. In these embodiments, the electronics module is configured to process the reference data with the first and second signals to generate analyte concentration data substantially without signal contribution due to noise. In some embodiments, the electronics module is configured to calibrate the dual-electrode analyte sensor data using the reference sensor data, as described elsewhere herein.

In some embodiments, the electronics module is configured to determine a scaling factor (k) as described in the section entitled "Calibration Systems and Methods." Briefly, a scaling factor defines a relationship between the enzymatic portion of the membrane and the non-enzymatic portion of the membrane. Accordingly, in some embodiments, the electronics module, also referred to as the processor module herein, is configured to calibrate the analyte sensor data using the scaling factor, such that the calibrated sensor data does not include inaccuracies that can arise due to small differences between the plus- and minus-enzyme portions of the membrane at the first and second working electrodes, respectively.

In some embodiments, the system is configured to calibrate the continuous dual-electrode analyte sensor using a reference fluid (e.g., 602a), as described in the section entitled "integrated sensor system." In some embodiments, the system is configured to calibrate the sensor using single-point calibration, in other embodiments, the system is configured to calibrate the sensor without a reference data point provided by an external analyte monitor (e.g., SMBG, YSI), as described elsewhere herein. In some embodiments, the system includes a reference sensor configured to generate a signal associated with a reference analyte in the sample (e.g., internal to the system), wherein the continuous analyte sensor is further configured to generate a third signal associated with the reference analyte, and wherein the system is configured to calibrate the continuous analyte sensor using the reference signal and the third signal. In some embodiments, the reference sensor comprises an optical sensing apparatus, such as but not limited to an optical $O_2$ sensor. In some embodiments, the continuous analyte sensor is a glucose sensor. In other embodiments, a substantial portion of the continuous analyte sensor has a diameter of less than about 0.008 inches, as is described elsewhere herein.

In some further embodiments, the continuous analyte sensor further comprises a bioinert material or a bioactive agent incorporated therein or thereon. Applicable bioactive agent include but are not limited to vitamin K antagonists, heparin group anticoagulants, platelet aggregation inhibitors, enzymes, direct thrombin inhibitors, Dabigatran, Defibrotide, Dermatan sulfate, Fondaparinux, and Rivaroxaban.

As a non-limiting example, in some embodiments, a method for continuously detecting an analyte in the host in vivo using a dual-electrode analyte sensor is provided. In some embodiments, a vascular access device (e.g., a catheter) is inserted into the host's circulatory system, such as into a vein or artery. The sensor is contacted with a sample of the circulatory system, such as a sample of blood withdrawn into the catheter. A first signal is generated by the sensor, wherein the first signal is associated with associated with the analyte and non-analyte related electroactive compounds having a first oxidation/reduction potential in a sample of the circulatory system of the host. In certain embodiments, the analyte sensor is configured to detect glucose. A second signal is also generated, wherein the second signal is associated with noise of the analyte sensor, wherein the noise comprises signal contribution due to non-analyte related electroactive species with an oxidation/reduction potential that substantially overlaps with the first oxidation/reduction potential in the sample. The first and second signals are processed to provide a processed signal substantially without a signal component associated with noise. In some embodiments, the first and second signals are processed to provide a scaling factor, which can then be used to calibrate the first signal. In some embodiments, a reference sensor is also contacted with the sample, and a third signal associated with a reference analyte generated. In some embodiments, the reference sensor is an optical detection apparatus, such as but not limited to an optical $O_2$ sensor. In this embodiment, the first and second signals can be calibrated using the third and/or reference signal. In some embodiments, the processing step comprises evaluating steady-state information and transient information, wherein the first and second signals each comprise steady-state and transient information. In some further embodiments, the evaluating step includes evaluating at least one of sensitivity information and baseline information, wherein the steady-state information comprises the sensitivity and baseline information.

Example

Test sensors were designed and fabricated with selection of certain materials, processing, and structure that improve fatigue life, and yet also improve comfort for the user. During the fabrication process, an elongated conductive body is first built by inserting/slip fitting a rod or wire into a tube formed of a conductive material, the combination of which forms an initial structure of an elongated conductive body. The resulting elongated conductive body is then passed through a series of dies to draw down the diameter of the elongated conductive body from a large diameter to a small diameter. With each pass through the die, the cross-sectional profile of the elongated conductive body is compressed, and the diameter associated therewith is reduced. Between passes through the die, an annealing step is performed to cause changes in the mechanical and structural properties of the elongated conductive body, and to relieve internal stresses, refine the structure by making it more homogeneous, and improve general cold working properties. It has been found that drawing down the diameter of the elongated conductive body through large numbers of dies in small incremental steps, instead of through one or a few number of large incremental step(s), can result in certain mechanical and structural properties that improve fatigue life. It has also been found that performing the annealing on the elongated conductive body in between drawing passes also improves fatigue life and provided additional comfort for the user. Afterwards, a polyurethane and a silver/silver chloride layer are coated onto the elongated conductive body, followed by deposition of a membrane (with an electrode, enzyme, and resistance layer).

Figure 14:
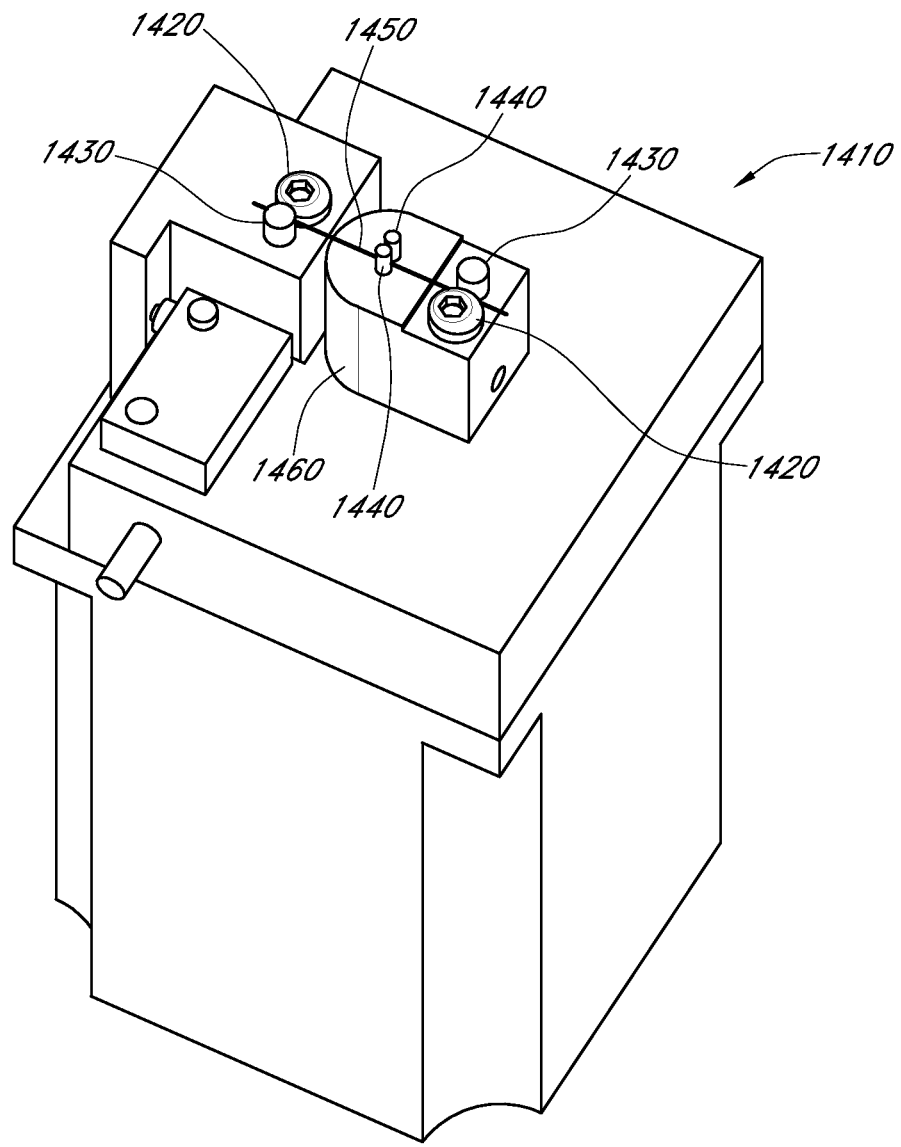
FIG. 14 is a perspective-view schematic illustrating a fatigue measurement device 1410.

The fabricated test sensors were then tested with a fatigue measurement device 1410 to determine test sensor fatigue lives under conditions that better models subcutaneous conditions than other conventional models. As illustrated in FIG. 14, the fatigue life measurement device 1410 includes clamp members 1420, holding members 1440, and fixtures 1430 used to hold and support the test sensor 1450. The fatigue life measurement device 1410 also includes a rotator 1460 that rotates about 45 degrees in each direction for a total of about 90 degrees per cycle. The radius of the holding members 1440 are about 0.031 inches. During testing, the rotator 1460 rotates back and forth at a constant rate, thereby causing the sensor 1450 to bend back at forth at a degree corresponding to the radius of the holding members 1440.

FIG. 15 illustrates a table summarizing the results of the performance of test sensors with conventional sensors, with respect to fatigue life. As shown, the test sensors using the fabrication techniques described above were able to achieve substantially longer fatigue lives than conventional sensors. Indeed the average fatigue life of the test sensors was about 61 cycles, as compared to the average fatigue life of the conventional sensors which was about 13.87 cycles. Accordingly, the fabrication methods described herein were able to extend sensor fatigue life by a factor over four. Indeed, sensors built in accordance with the embodiments described herein can achieve a fatigue life of greater than 20 cycles, greater than 40 cycles, greater than 60 cycles, or greater than 65 cycles.

While various embodiments of the invention have been described above, it should be understood that they have been presented by way of example only, and not by way of limitation. Likewise, the various diagrams may depict an example architectural or other configuration for the disclosure, which is done to aid in understanding the features and functionality that can be included in the disclosure. The disclosure is not restricted to the illustrated example architectures or configurations, but can be implemented using a variety of alternative architectures and configurations. Additionally, although the disclosure is described above in terms of various exemplary embodiments and implementations, it should be understood that the various features and functionality described in one or more of the individual embodiments are not limited in their applicability to the particular embodiment with which they are described. They instead can be applied, alone or in some combination, to one or more of the other embodiments of the disclosure, whether or not such embodiments are described, and whether or not such features are presented as being a part of a described embodiment. Thus the breadth and scope of the present disclosure should not be limited by any of the above-described exemplary embodiments.

It will be appreciated that, for clarity purposes, the above description has described embodiments with reference to different functional units. However, it will be apparent that any suitable distribution of functionality between different functional units may be used without detracting from the invention. For example, functionality illustrated to be performed by separate computing devices may be performed by the same computing device. Likewise, functionality illustrated to be performed by a single computing device may be distributed amongst several computing devices. Hence, references to specific functional units are only to be seen as references to suitable means for providing the described functionality, rather than indicative of a strict logical or physical structure or organization.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A continuous analyte sensor configured for in vivo use, the continuous analyte sensor comprising:
an elongated conductive body comprising a working electrode, wherein the elongated conductive body has a Young's modulus of from about 170 GPa to about 220 GPa and a yield strength from about 800 MPa to about 3,000 MPa; and
a membrane covering at least a portion of the working electrode, wherein the membrane comprises an enzyme layer.

2. The continuous analyte sensor of claim 1, wherein the elongated conductive body comprises an elongated core, an insulating layer covering at least a portion of the elongated core, a conductive layer comprising a reference electrode or a counter electrode and covering at least a portion of the insulating layer, and a membrane covering at least a portion the working electrode.

3. The continuous analyte sensor of claim 2, wherein the elongated core comprises an elongated body and a layer of conductive material covering at least a portion of the elongated body.

4. The continuous analyte sensor of claim 3, wherein the elongated body comprises at least one material selected from the group consisting of stainless steel, titanium, tantalum, and a polymer.

5. The continuous analyte sensor of claim 3, wherein the layer of conductive material covering at least a portion of the elongated body comprises a conductive material selected from the group consisting of platinum, platinum-iridium, gold, palladium, iridium, alloys thereof, graphite, carbon, and a conductive polymer.

6. The continuous analyte sensor of claim 2, wherein the conductive layer comprising the reference electrode or the counter electrode comprises a silver-containing material.

7. The continuous analyte sensor of claim 6, wherein the silver-containing material has a particle size associated with a maximum particle dimension that is less than about 100 microns.

8. The continuous analyte sensor of claim 7, wherein the silver-containing material has a particle shape that is substantially spherical.

9. The continuous analyte sensor of claim 2, wherein the insulating layer comprises at least one polymer selected from the group consisting of polyurethane and polyimide.

10. The continuous analyte sensor of claim 2, wherein a ratio of a thickness of the conductive layer to a thickness of insulating layer is from about 1:5 to about 1:1.

11. The continuous analyte sensor of claim 2 wherein the conductive material is a silver-containing material.

12. The continuous analyte sensor of claim 1, wherein the membrane comprises a polymer having a Shore hardness of from about 70 A to about 55 D.

13. The continuous analyte sensor of claim 1, having an ultimate tensile strength of from about 80 kPsi to about 500 kPsi.

14. The continuous analyte sensor of claim 1, having an ultimate tensile strength of from about 150 kPsi to about 280 kPsi.

15. The continuous analyte sensor of claim 1, having a fatigue life of at least 1,000 cycles of flexing of from about 28° to about 110° at a bend radius of about 0.125-inches.

16. The continuous analyte sensor of claim 1, which is configured for multi-axis bending.

17. The continuous analyte sensor of claim 16, wherein the multi-axis bending is associated with flexing in at least three directions.

18. The continuous analyte sensor of claim 1, wherein the elongated conductive body has a diameter of from about 50 microns to about 250 microns.

19. The continuous analyte sensor of claim 1, wherein the sensor has a cross-sectional radius of from about 5 microns to about 200 microns.

20. The continuous analyte sensor of claim 1, having a fatigue life of at least 20 cycles of flexing of from about 45° to about −45° at a bend radius of about 0.031-inches.

21. The continuous analyte sensor of claim 1, having a fatigue life of at least 40 cycles of flexing of from about 45° to about −45° at a bend radius of about 0.031-inches.

22. The continuous analyte sensor of claim 1, having a fatigue life of at least 50 cycles of flexing of from about 45° to about −45° at a bend radius of about 0.031-inches.

23. The continuous analyte sensor of claim 1, having a fatigue life of at least 60 cycles of flexing of from about 45° to about −45° at a bend radius of about 0.031-inches.

24. The continuous analyte sensor of claim 1, having a fatigue life of at least 65 cycles of flexing of from about 45° to about −45° at a bend radius of about 0.031-inches.

* * * * *

UNITED STATES PATENT AND TRADEMARK OFFICE
CERTIFICATE OF CORRECTION

PATENT NO. : 9,131,885 B2
APPLICATION NO. : 12/829318
DATED : September 15, 2015
INVENTOR(S) : Peter C. Simpson et al.

It is certified that error appears in the above-identified patent and that said Letters Patent is hereby corrected as shown below:

On the title page

In column 2 (page 1, item 56) at line 13, Under Other Publications, change "pdf/FWW" to --pdf/FWM--.

In the specification

In column 18 at line 42, Change "ibuprophen," to --ibuprofen,--.

In column 18 at line 48, Change "andrenostenedione;" to --androstenedione;--.

In column 18 at line 50, Change "biotimidase;" to --biotinidase;--.

In column 18 at line 64, Change "diptheria/tetanus" to --diphtheria/tetanus--.

In column 19 at line 4, Change "perioxidase;" to --peroxidase;--.

In column 19 at line 10, Change "phenyloin;" to --phenytoin;--.

In column 19 at line 18, Change "duodenalisa," to --duodenalis,--.

In column 19 at line 25, Change "Trepenoma pallidium," to --Treponema pallidum,--.

In column 19 at line 26, Change "stomatis" to --stomatitis--.

In column 19 at line 47, Change "(barbituates," to --(barbiturates,--.

In column 31 at line 46, Change "1060B)" to --106B)--.

In column 39 at line 7, After "like" insert --.--.

In column 43 at line 35, Change "Bellafonte," to --Bellefonte,--.

In column 45 at line 37, Change "and or" to --and/or--.

In column 47 at line 29, Change "and or" to --and/or--.

In column 65 at line 36, Change "that that" to --that--.

In column 84 at line 59, Change "at" to --and--.

Signed and Sealed this
Ninth Day of August, 2016

Michelle K. Lee
*Director of the United States Patent and Trademark Office*